US007090985B2

(12) United States Patent
Lynch et al.

(10) Patent No.: US 7,090,985 B2
(45) Date of Patent: Aug. 15, 2006

(54) METHODS FOR THE IDENTIFICATION OF AGENTS FOR THE TREATMENT OF SEIZURES, NEUROLOGICAL DISEASES, ENDOCRINOPATHIES AND HORMONAL DISEASES

(75) Inventors: Berkley Lynch, Cambridge, MA (US); Karl Nocka, Cambridge, MA (US); Bruno Fuks, Brussels (BE)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 10/308,163

(22) Filed: Dec. 3, 2002

(65) Prior Publication Data

US 2004/0106147 A1 Jun. 3, 2004

(51) Int. Cl.
*G01N 33/53* (2006.01)
*C12P 21/06* (2006.01)

(52) U.S. Cl. ...................... 435/7.1; 435/69.1
(58) Field of Classification Search .............. 435/4; 530/300, 350
See application file for complete search history.

(56) References Cited

U.S. PATENT DOCUMENTS

2002/0142383 A1 10/2002 Merkulov et al.
2003/0009024 A1 1/2003 Curtis

OTHER PUBLICATIONS

Genbank Accession O94841, May 1, 1999, KIAA0736 human SV2 in DNA Res., 5:277-286, 1998, 100% identical to SEQ ID No. 2.*
Lynch et al., PNAS, 101(26):9861-66, Jun. 29, 2004.*
Differding et al., (EP01/01992) published as WO01/62726, Aug. 30, 2001.*
Choh et al., PNAS, 77(6):3211-14, 1980.*
Miyata et al., Br. J. of Haematology, 88:156-65, 1994.*
Skolnick et al., TIBTECH., 18(1):34-39, 2000.*
Janz, R et al. SVOP, an evolutionarily conserved synaptic vesicle protein, suggests novel transport functions of synaptic vesicles. J Neurosci. 1998; 18(22):9269-9281.
Janz, R et al. SV2A and SV2B function as redundant Ca2+ regulators in neurotransmitter release. Neuron. 1999; 24(4):1003-1016.
Janz, R. Knockout mice and SV2 synaptic-vesicle proteins. University of Texas Health Science Center at Houston Neuroscience Research Center Newsletter. 2001; 7(3):1,4-5.

Margineanu, DG et al. Levetiracetam: Mehanisms of action. In: Antiepileptic Drugs, 5ht Editiion. Levy,RH et al. eds. 2002; Lippincott Williams & Wilkins, Philadelphia, PA. pp. 419-427.
Noyer, M et al. The novel antiepileptic drug levetiracetam (ucb L059) appears to act via a specific binding site in CNS membranes. Eur J Pharmacol. 1995; 286(2)137-146.
Pyle, RA et al. Phosphorylation of synaptic vesicle protein 2 modulates binding to synaptotagmin. J Biol Chem. 2000; 275(22):17195-17200.
Schivell, AE et al. Isoform-specific, calcium-regulated interaction of synaptic vesicle proteins SV2 and synaptotagmin. J Biol Chem. 1996; 271(44):27770-27775.
Son, Y-J et al. The synaptic vesicle protein SV2 is complexed with an alpha5- containing laminin on the nerve terminal surface. J Biol Chem. 2000; 275(1):451-460.
Xu, T et al. SV2 modulates the size of the readily releasable pool of secretory vesicles. Nat Cell Biol. 2001; 3(8):691-698.
Bajjalieh SM, et al. SV2, a brain synaptic vesicle protein homologous to bacterial transporters. Science 1992; 257(5074):1271-1273.
Bajjalieh SM, et al. Brain contains two forms of synaptic vesicle protein 2. Proc Natl Acad Sci (USA). 1993; 90(6):2150-2154.
Bajjalieh SM, et al. Differential expression of synaptic vesicle protein 2 (SV2) isoforms. J Neurosci. 1994 ; 14(9):5223-5235.
Buckley, K et al. Identification of a transmembrane glycoprotein specific for secretory vesicles of neural and endocrine cells. J. Cell Biol. 1985; 100(4):1284-1294.
Crowder, KM et al. Abnormal neurotransmission in mice lacking synaptic vesicle protein 2A (SV2A). Proc Natl Acad Sci (USA). 1999; 96(26):15268-15273.
Feany, MB et al. The synaptic vesicle protein SV2 is a novel type of transmembrane transporter. Cell. 1992; 70(5):861-867.
Hayashi, M et al. Syntaptic vesicle protein SV2B, but not SV2A, is predominantly expressed and associated with microvesicles in rat pinealocytes. Adv Exp Med Biol. 1999; 460:91-93.

* cited by examiner

*Primary Examiner*—Sharon Turner
(74) *Attorney, Agent, or Firm*—Morgan Lewis & Bockius LLP

(57) ABSTRACT

The present invention is drawn to methods of characterization of the properties and functions of SV2 proteins. The invention further includes methods of identifying compounds or agents which modulate the activity of SV2 proteins. Included in these methods is the identification of compounds or agents which modulate the binding of levetiracetam SV2 proteins, including SV2A.

24 Claims, 16 Drawing Sheets

A

A  B

[³H]Levetiracetam  [³H]ucb 30889

SEQUENCE LISTING

```
<160> NUMBER OF SEQ ID NOS: 16

<210> SEQ ID NO 1
<211> LENGTH: 2229
<212> TYPE: DNA
<213> ORGANISM: Homo sapiens
<220> FEATURE:
<221> NAME/KEY: CDS
<222> LOCATION: (1)..(2229)
<223> OTHER INFORMATION:

<400> SEQUENCE: 1 atg gaa gag ggc ttc cga gac cgg gca gct ttc atc cgt ggg gcc aaa      48
Met Glu Glu Gly Phe Arg Asp Arg Ala Ala Phe Ile Arg Gly Ala Lys
1               5                   10                  15
```

```
                                                        -continued gac att gct aag gaa gtc aaa aag cat gcg gcc aag aag gtg gtg aag        96
Asp Ile Ala Lys Glu Val Lys Lys His Ala Ala Lys Lys Val Val Lys
         20                  25                  30 ggc ctg gac aga gtc cag gac gaa tat tcc cga aga tcg tac tcc cgc       144
Gly Leu Asp Arg Val Gln Asp Glu Tyr Ser Arg Arg Ser Tyr Ser Arg
     35                  40                  45 ttt gag gag gag gat gat gat gac ttc cct gct ccc agt gat ggt           192
Phe Glu Glu Glu Asp Asp Asp Asp Phe Pro Ala Pro Ser Asp Gly
 50                  55                  60 tat tac cga gga gaa ggg acc cag gat gag gag gaa ggt ggt gca tcc       240
Tyr Tyr Arg Gly Glu Gly Thr Gln Asp Glu Glu Glu Gly Gly Ala Ser
 65                  70                  75                  80 agt gat gct act gag ggc cat gac gag gat gat gag atc tat gaa ggg       288
Ser Asp Ala Thr Glu Gly His Asp Glu Asp Asp Glu Ile Tyr Glu Gly
             85                  90                  95 gaa tat cag ggc att ccc cgg gca gag tct ggg ggc aaa ggc gag cgg       336
Glu Tyr Gln Gly Ile Pro Arg Ala Glu Ser Gly Gly Lys Gly Glu Arg
             100                 105                 110 atg gca gat ggg gcg ccc ctg gct gga gta agg ggg ggc ttg agt gat       384
Met Ala Asp Gly Ala Pro Leu Ala Gly Val Arg Gly Gly Leu Ser Asp
         115                 120                 125 ggg gag ggt ccc cct ggg ggc cgg ggg gag gca caa cga cgg aaa gaa       432
Gly Glu Gly Pro Pro Gly Gly Arg Gly Glu Ala Gln Arg Arg Lys Glu
 130                 135                 140 cga gaa gaa ctg gcc caa cag tat gaa gcc atc cta cgg gag tgt ggc       480
Arg Glu Glu Leu Ala Gln Gln Tyr Glu Ala Ile Leu Arg Glu Cys Gly
 145                 150                 155                 160 cac ggc cgc ttc cag tgg aca ctg tat ttt gtg ctt ggt ctg gcg ctg       528
His Gly Arg Phe Gln Trp Thr Leu Tyr Phe Val Leu Gly Leu Ala Leu
             165                 170                 175 atg gct gac ggt gtg gag gtc ttt gtg gtg ggc ttc gtg ctg ccc agc       576
Met Ala Asp Gly Val Glu Val Phe Val Val Gly Phe Val Leu Pro Ser
         180                 185                 190 gct gag aaa gac atg tgc ctg tcc gac tcc aac aaa ggc atg cta ggc       624
Ala Glu Lys Asp Met Cys Leu Ser Asp Ser Asn Lys Gly Met Leu Gly
         195                 200                 205 ctc atc gtc tac ctg ggc atg atg gtg gga gcc ttc ctc tgg gga ggt       672
Leu Ile Val Tyr Leu Gly Met Met Val Gly Ala Phe Leu Trp Gly Gly
 210                 215                 220 ctg gct gac cgg ctg ggt cgg agg cag tgt ctg ctc atc tcg ctc tca       720
Leu Ala Asp Arg Leu Gly Arg Arg Gln Cys Leu Leu Ile Ser Leu Ser
 225                 230                 235                 240 gtc aac agc gtc ttc gcc ttc ttc tca tct ttt gtc cag ggt tac ggc       768
Val Asn Ser Val Phe Ala Phe Phe Ser Ser Phe Val Gln Gly Tyr Gly
             245                 250                 255 act ttc ctc ttc tgc cgc cta ctt tct ggg gtt ggg att gga ggg tcc       816
Thr Phe Leu Phe Cys Arg Leu Leu Ser Gly Val Gly Ile Gly Gly Ser
         260                 265                 270 atc ccc att gtc ttc tcc tat ttc tcc gag ttt ctg gcc cag gag aaa       864
Ile Pro Ile Val Phe Ser Tyr Phe Ser Glu Phe Leu Ala Gln Glu Lys
         275                 280                 285 cga ggg gag cat ttg agc tgg ctc tgc atg ttt tgg atg att ggt ggc       912
Arg Gly Glu His Leu Ser Trp Leu Cys Met Phe Trp Met Ile Gly Gly
 290                 295                 300 gtg tac gca gct gct atg gcc tgg gcc atc atc ccc cac tat ggg tgg       960
Val Tyr Ala Ala Ala Met Ala Trp Ala Ile Ile Pro His Tyr Gly Trp
 305                 310                 315                 320 agt ttt cag atg ggt tct gcc tac cag ttc cac agc tgg agg gtc ttc      1008
Ser Phe Gln Met Gly Ser Ala Tyr Gln Phe His Ser Trp Arg Val Phe
             325                 330                 335
```

```
gtc ctc gtc tgc gcc ttt cct tct gtg ttt gcc att ggg gct ctg acc      1056
Val Leu Val Cys Ala Phe Pro Ser Val Phe Ala Ile Gly Ala Leu Thr
            340                 345                 350 acg cag cct gag agc ccc cgt ttc ttc cta gag aat gga aag cat gat      1104
Thr Gln Pro Glu Ser Pro Arg Phe Phe Leu Glu Asn Gly Lys His Asp
                355                 360                 365 gag gcc tgg atg gtg ctg aag cag gtc cat gat acc aac atg cga gcc      1152
Glu Ala Trp Met Val Leu Lys Gln Val His Asp Thr Asn Met Arg Ala
370                 375                 380 aaa gga cat cct gag cga gtg ttc tca gta acc cac att aag acg att      1200
Lys Gly His Pro Glu Arg Val Phe Ser Val Thr His Ile Lys Thr Ile
385                 390                 395                 400 cat cag gag gat gaa ttg att gag atc cag tcg gac aca ggg acc tgg      1248
His Gln Glu Asp Glu Leu Ile Glu Ile Gln Ser Asp Thr Gly Thr Trp
                405                 410                 415 tac cag cgc tgg ggg gtc cgg gcc ttg agc cta ggg ggg cag gtt tgg      1296
Tyr Gln Arg Trp Gly Val Arg Ala Leu Ser Leu Gly Gly Gln Val Trp
                420                 425                 430 ggg aat ttt ctc tcc tgt ttt ggt ccc gaa tat cgg cgc atc act ctg      1344
Gly Asn Phe Leu Ser Cys Phe Gly Pro Glu Tyr Arg Arg Ile Thr Leu
            435                 440                 445 atg atg atg ggt gtg tgg ttc acc atg tca ttc agc tac tat ggc ctg      1392
Met Met Met Gly Val Trp Phe Thr Met Ser Phe Ser Tyr Tyr Gly Leu
450                 455                 460 acc gtc tgg ttt cct gac atg atc cgc cat ctc cag gca gtg gac tac      1440
Thr Val Trp Phe Pro Asp Met Ile Arg His Leu Gln Ala Val Asp Tyr
465                 470                 475                 480 gca tcc cgc acc aaa gtg ttc ccc ggg gag cgc gta gag cat gta act      1488
Ala Ser Arg Thr Lys Val Phe Pro Gly Glu Arg Val Glu His Val Thr
                485                 490                 495 ttt aac ttc acg ttg gag aat cag atc cac cga ggc ggg cag tac ttc      1536
Phe Asn Phe Thr Leu Glu Asn Gln Ile His Arg Gly Gly Gln Tyr Phe
                500                 505                 510 aat gac aag ttc att ggg ctg cgg ctc aag tca gtg tcc ttt gag gat      1584
Asn Asp Lys Phe Ile Gly Leu Arg Leu Lys Ser Val Ser Phe Glu Asp
            515                 520                 525 tcc ctg ttt gaa gag tgt tat ttt gag gat gtc aca tcc agc aac acg      1632
Ser Leu Phe Glu Glu Cys Tyr Phe Glu Asp Val Thr Ser Ser Asn Thr
            530                 535                 540 ttt ttc cgc aac tgc aca ttc atc aac act gtg ttc tat aac act gac      1680
Phe Phe Arg Asn Cys Thr Phe Ile Asn Thr Val Phe Tyr Asn Thr Asp
545                 550                 555                 560 ctg ttc gag tac aag ttt gtg aac agc cgt ctg ata aac agt aca ttc      1728
Leu Phe Glu Tyr Lys Phe Val Asn Ser Arg Leu Ile Asn Ser Thr Phe
                565                 570                 575 ctg cac aac aag gag ggc tgc ccg cta gac gtg aca ggg acg ggc gaa      1776
Leu His Asn Lys Glu Gly Cys Pro Leu Asp Val Thr Gly Thr Gly Glu
                580                 585                 590 ggt gcc tac atg gta tac ttt gtg agc ttc ctg ggg aca ctg gca gtg      1824
Gly Ala Tyr Met Val Tyr Phe Val Ser Phe Leu Gly Thr Leu Ala Val
            595                 600                 605 ctt cct ggg aat atc gtg tct gcc ctg ctc atg gac aag atc ggc agg      1872
Leu Pro Gly Asn Ile Val Ser Ala Leu Leu Met Asp Lys Ile Gly Arg
610                 615                 620 ctc aga atg ctt gct ggc tcc agc gtg atg tcc tgt gtc tcc tgc ttc      1920
Leu Arg Met Leu Ala Gly Ser Ser Val Met Ser Cys Val Ser Cys Phe
625                 630                 635                 640 ttc ctg tct ttt ggg aac agt gag tcg gcc atg atc gct ctg ctc tgc      1968
Phe Leu Ser Phe Gly Asn Ser Glu Ser Ala Met Ile Ala Leu Leu Cys
                645                 650                 655
```

```
ctt ttt ggc ggg gtc agc att gca tcc tgg aat gcg ctg gac gtg ttg      2016
Leu Phe Gly Gly Val Ser Ile Ala Ser Trp Asn Ala Leu Asp Val Leu
        660                 665                 670 act gtt gaa ctc tac ccc tca gac aag agg acc aca gct ttt ggc ttc      2064
Thr Val Glu Leu Tyr Pro Ser Asp Lys Arg Thr Thr Ala Phe Gly Phe
            675                 680                 685 ctg aat gcc ctg tgt aag ctg gca gct gtg ctg ggg atc agc atc ttc      2112
Leu Asn Ala Leu Cys Lys Leu Ala Ala Val Leu Gly Ile Ser Ile Phe
    690                 695                 700 aca tcc ttc gtg gga atc acc aag gct gca ccc atc ctc ttt gcc tca      2160
Thr Ser Phe Val Gly Ile Thr Lys Ala Ala Pro Ile Leu Phe Ala Ser
705                 710                 715                 720 gct gcc ctt gcc ctt ggc agc tct ctg gcc ctg aag ctg cct gag acc      2208
Ala Ala Leu Ala Leu Gly Ser Ser Leu Ala Leu Lys Leu Pro Glu Thr
                725                 730                 735 cgg ggg cag gtg ctg cag tga                                          2229
Arg Gly Gln Val Leu Gln
            740

<210> SEQ ID NO 2
<211> LENGTH: 742
<212> TYPE: PRT
<213> ORGANISM: Homo sapiens

<400> SEQUENCE: 2

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Asp Phe Pro Ala Pro Ser Asp Gly
    50                  55                  60

Tyr Tyr Arg Gly Glu Gly Thr Gln Asp Glu Glu Gly Gly Ala Ser
65                  70                  75                  80

Ser Asp Ala Thr Glu Gly His Asp Glu Asp Glu Ile Tyr Glu Gly
                85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Leu Ser Asp
        115                 120                 125

Gly Glu Gly Pro Pro Gly Gly Arg Gly Glu Ala Gln Arg Arg Lys Glu
    130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Phe Ser Ser Phe Val Gln Gly Tyr Gly
```

-continued

```
                245                 250                 255
Thr Phe Leu Phe Cys Arg Leu Leu Ser Gly Val Gly Ile Gly Gly Ser
                260                 265                 270
Ile Pro Ile Val Phe Ser Tyr Phe Ser Glu Phe Leu Ala Gln Glu Lys
                275                 280                 285
Arg Gly Glu His Leu Ser Trp Leu Cys Met Phe Trp Met Ile Gly Gly
                290                 295                 300
Val Tyr Ala Ala Ala Met Ala Trp Ala Ile Ile Pro His Tyr Gly Trp
305                 310                 315                 320
Ser Phe Gln Met Gly Ser Ala Tyr Gln Phe His Ser Trp Arg Val Phe
                325                 330                 335
Val Leu Val Cys Ala Phe Pro Ser Val Phe Ala Ile Gly Ala Leu Thr
                340                 345                 350
Thr Gln Pro Glu Ser Pro Arg Phe Phe Leu Glu Asn Gly Lys His Asp
                355                 360                 365
Glu Ala Trp Met Val Leu Lys Gln Val His Asp Thr Asn Met Arg Ala
                370                 375                 380
Lys Gly His Pro Glu Arg Val Phe Ser Val Thr His Ile Lys Thr Ile
385                 390                 395                 400
His Gln Glu Asp Glu Leu Ile Glu Ile Gln Ser Asp Thr Gly Thr Trp
                405                 410                 415
Tyr Gln Arg Trp Gly Val Arg Ala Leu Ser Leu Gly Gly Gln Val Trp
                420                 425                 430
Gly Asn Phe Leu Ser Cys Phe Gly Pro Glu Tyr Arg Arg Ile Thr Leu
                435                 440                 445
Met Met Met Gly Val Trp Phe Thr Met Ser Phe Ser Tyr Tyr Gly Leu
                450                 455                 460
Thr Val Trp Phe Pro Asp Met Ile Arg His Leu Gln Ala Val Asp Tyr
465                 470                 475                 480
Ala Ser Arg Thr Lys Val Phe Pro Gly Glu Arg Val Glu His Val Thr
                485                 490                 495
Phe Asn Phe Thr Leu Glu Asn Gln Ile His Arg Gly Gly Gln Tyr Phe
                500                 505                 510
Asn Asp Lys Phe Ile Gly Leu Arg Leu Lys Ser Val Ser Phe Glu Asp
                515                 520                 525
Ser Leu Phe Glu Glu Cys Tyr Phe Glu Asp Val Thr Ser Ser Asn Thr
                530                 535                 540
Phe Phe Arg Asn Cys Thr Phe Ile Asn Thr Val Phe Tyr Asn Thr Asp
545                 550                 555                 560
Leu Phe Glu Tyr Lys Phe Val Asn Ser Arg Leu Ile Asn Ser Thr Phe
                565                 570                 575
Leu His Asn Lys Glu Gly Cys Pro Leu Asp Val Thr Gly Thr Gly Glu
                580                 585                 590
Gly Ala Tyr Met Val Tyr Phe Val Ser Phe Leu Gly Thr Leu Ala Val
                595                 600                 605
Leu Pro Gly Asn Ile Val Ser Ala Leu Leu Met Asp Lys Ile Gly Arg
                610                 615                 620
Leu Arg Met Leu Ala Gly Ser Ser Val Met Ser Cys Val Ser Cys Phe
625                 630                 635                 640
Phe Leu Ser Phe Gly Asn Ser Glu Ser Ala Met Ile Ala Leu Leu Cys
                645                 650                 655
Leu Phe Gly Gly Val Ser Ile Ala Ser Trp Asn Ala Leu Asp Val Leu
                660                 665                 670
```

```
Thr Val Glu Leu Tyr Pro Ser Asp Lys Arg Thr Thr Ala Phe Gly Phe
            675                 680                 685

Leu Asn Ala Leu Cys Lys Leu Ala Val Leu Gly Ile Ser Ile Phe
        690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 3
<211> LENGTH: 2052
<212> TYPE: DNA
<213> ORGANISM: Homo sapiens
<220> FEATURE:
<221> NAME/KEY: CDS
<222> LOCATION: (1)..(2052)
<223> OTHER INFORMATION:

<400> SEQUENCE: 3 atg gat gac tac aag tat cag gac aat tat ggg ggc tat gct ccc agt     48
Met Asp Asp Tyr Lys Tyr Gln Asp Asn Tyr Gly Gly Tyr Ala Pro Ser
1               5                   10                  15 gat ggc tat tac cgc ggc aat gag tcc aac cca gaa gaa gat gca cag     96
Asp Gly Tyr Tyr Arg Gly Asn Glu Ser Asn Pro Glu Glu Asp Ala Gln
            20                  25                  30 agt gat gtc acc gaa ggc cat gat gag gaa gac gag atc tat gag ggc    144
Ser Asp Val Thr Glu Gly His Asp Glu Glu Asp Glu Ile Tyr Glu Gly
        35                  40                  45 gag tac cag ggt atc cct cac cca gat gat gtc aag gcc aag cag gcc    192
Glu Tyr Gln Gly Ile Pro His Pro Asp Asp Val Lys Ala Lys Gln Ala
    50                  55                  60 aag atg gcg ccc tcc aga atg gac agc ctt cgg ggc cag aca gac ctg    240
Lys Met Ala Pro Ser Arg Met Asp Ser Leu Arg Gly Gln Thr Asp Leu
65              70                  75                  80 atg gct gag agg ctg gaa gat gag gag cag ttg gcc cac cag tac gag    288
Met Ala Glu Arg Leu Glu Asp Glu Glu Gln Leu Ala His Gln Tyr Glu
                85                  90                  95 acc atc atg gat gag tgt ggc cat ggc cgc ttc cag tgg atc ctc ttt    336
Thr Ile Met Asp Glu Cys Gly His Gly Arg Phe Gln Trp Ile Leu Phe
            100                 105                 110 ttc gtc ttg ggt ttg gcc ctg atg gcc gat ggg gtg gaa gtg ttc gtg    384
Phe Val Leu Gly Leu Ala Leu Met Ala Asp Gly Val Glu Val Phe Val
        115                 120                 125 gtg agt ttt gcc ctg ccc agt gca gag aag gac atg tgt ctg tcc agt    432
Val Ser Phe Ala Leu Pro Ser Ala Glu Lys Asp Met Cys Leu Ser Ser
    130                 135                 140 tcc aaa aaa gga atg cta ggg atg ata gtc tac ttg gga atg atg gcg    480
Ser Lys Lys Gly Met Leu Gly Met Ile Val Tyr Leu Gly Met Met Ala
145                 150                 155                 160 ggc gcc ttc atc ctg gga ggc ctg gct gat aag ctg gga agg aag cga    528
Gly Ala Phe Ile Leu Gly Gly Leu Ala Asp Lys Leu Gly Arg Lys Arg
                165                 170                 175 gtc ctc agc atg tct ctg gcc gtc aat gcc tcc ttc gcc tcc ctc tct    576
Val Leu Ser Met Ser Leu Ala Val Asn Ala Ser Phe Ala Ser Leu Ser
            180                 185                 190 tcc ttc gtg cag gga tat gga gcc ttc ctc ttc tgc cga ctc atc tca    624
Ser Phe Val Gln Gly Tyr Gly Ala Phe Leu Phe Cys Arg Leu Ile Ser
        195                 200                 205
```

-continued

```
ggc atc ggt att ggg ggt gct cta ccg att gtt ttt gcc tat ttt tct      672
Gly Ile Gly Ile Gly Gly Ala Leu Pro Ile Val Phe Ala Tyr Phe Ser
210             215                 220 gaa ttc ttg tct cgg gag aag cga gga gaa cac ctc agt tgg ctg ggc      720
Glu Phe Leu Ser Arg Glu Lys Arg Gly Glu His Leu Ser Trp Leu Gly
225             230                 235                 240 atc ttc tgg atg act ggg ggc ctg tac gca tct gcc atg gcc tgg agc      768
Ile Phe Trp Met Thr Gly Gly Leu Tyr Ala Ser Ala Met Ala Trp Ser
                245                 250                 255 atc atc cca cac tat ggc tgg ggc ttc agc atg ggg acc aat tac cac      816
Ile Ile Pro His Tyr Gly Trp Gly Phe Ser Met Gly Thr Asn Tyr His
            260                 265                 270 ttc cat agc tgg aga gtg ttt gtc atc gtc tgt gct ctg ccc tgc acc      864
Phe His Ser Trp Arg Val Phe Val Ile Val Cys Ala Leu Pro Cys Thr
        275                 280                 285 gtg tcc atg gtg gcc ctg aag ttc atg cca gag agc cca agg ttt ctg      912
Val Ser Met Val Ala Leu Lys Phe Met Pro Glu Ser Pro Arg Phe Leu
    290                 295                 300 cta gag atg ggc aaa cat gat gaa gcc tgg atg att ctc aag caa gtc      960
Leu Glu Met Gly Lys His Asp Glu Ala Trp Met Ile Leu Lys Gln Val
305                 310                 315                 320 cat gac acc aac atg aga gct aag ggg acc cca gag aaa gtg ttc acg     1008
His Asp Thr Asn Met Arg Ala Lys Gly Thr Pro Glu Lys Val Phe Thr
                325                 330                 335 gtt tcc aac atc aaa act ccc aag caa atg gat gaa ttc att gag atc     1056
Val Ser Asn Ile Lys Thr Pro Lys Gln Met Asp Glu Phe Ile Glu Ile
                340                 345                 350 caa agt tca aca gga acc tgg tac cag cgc tgg ctg gtc aga ttc aag     1104
Gln Ser Ser Thr Gly Thr Trp Tyr Gln Arg Trp Leu Val Arg Phe Lys
            355                 360                 365 acc att ttc aag cag gtc tgg gat aat gcc ctg tac tgt gtg atg ggg     1152
Thr Ile Phe Lys Gln Val Trp Asp Asn Ala Leu Tyr Cys Val Met Gly
        370                 375                 380 ccc tac aga atg aat aca ctg att ctg gcc gtg gtt tgg ttt gcc atg     1200
Pro Tyr Arg Met Asn Thr Leu Ile Leu Ala Val Val Trp Phe Ala Met
385                 390                 395                 400 gca ttc agt tac tat gga ctg aca gtt tgg ttt cct gat atg atc cgc     1248
Ala Phe Ser Tyr Tyr Gly Leu Thr Val Trp Phe Pro Asp Met Ile Arg
                405                 410                 415 tat ttt caa gat gaa gaa tac aag tct aaa atg aag gtg ttt ttt ggt     1296
Tyr Phe Gln Asp Glu Glu Tyr Lys Ser Lys Met Lys Val Phe Phe Gly
                420                 425                 430 gag cat gtg tac ggc gcc aca atc aac ttc acg atg gaa aat cag atc     1344
Glu His Val Tyr Gly Ala Thr Ile Asn Phe Thr Met Glu Asn Gln Ile
            435                 440                 445 cac caa cat ggg aaa ctt gtg aat gat aag ttc aca aga atg tac ttt     1392
His Gln His Gly Lys Leu Val Asn Asp Lys Phe Thr Arg Met Tyr Phe
        450                 455                 460 aaa cat gta ctc ttt gag gac aca ttc ttt gac gag tgt tat ttt gaa     1440
Lys His Val Leu Phe Glu Asp Thr Phe Phe Asp Glu Cys Tyr Phe Glu
465                 470                 475                 480 gac gta aca tca aca gat acc tac ttc aaa aat tgt acc att gaa tca     1488
Asp Val Thr Ser Thr Asp Thr Tyr Phe Lys Asn Cys Thr Ile Glu Ser
                485                 490                 495 acc atc ttt tac aac aca gac ctc tac gag cac aag ttc atc aac tgt     1536
Thr Ile Phe Tyr Asn Thr Asp Leu Tyr Glu His Lys Phe Ile Asn Cys
                500                 505                 510 cgg ttt atc aac tcc acc ttc ctg gag cag aag gag ggc tgc cac atg     1584
Arg Phe Ile Asn Ser Thr Phe Leu Glu Gln Lys Glu Gly Cys His Met
```

-continued

```
                515                 520                 525
gac ttg gag caa gat aat gac ttc ctg att tac ctc gtc agc ttc ctg      1632
Asp Leu Glu Gln Asp Asn Asp Phe Leu Ile Tyr Leu Val Ser Phe Leu
        530                 535                 540 ggc agc ctg tct gtc tta ccc ggg aac atc att tct gcc ctg ctc atg      1680
Gly Ser Leu Ser Val Leu Pro Gly Asn Ile Ile Ser Ala Leu Leu Met
545                 550                 555                 560 gat aga att gga agg ctc aag atg att ggt ggc tcc atg cta atc tct      1728
Asp Arg Ile Gly Arg Leu Lys Met Ile Gly Gly Ser Met Leu Ile Ser
                565                 570                 575 gca gtc tgc tgc ttc ttc ctg ttt ttt ggc aac agt gag tct gca atg      1776
Ala Val Cys Cys Phe Phe Leu Phe Phe Gly Asn Ser Glu Ser Ala Met
            580                 585                 590 atc ggc tgg cag tgc ctg ttc tgt ggg aca agc att gca gcc tgg aat      1824
Ile Gly Trp Gln Cys Leu Phe Cys Gly Thr Ser Ile Ala Ala Trp Asn
        595                 600                 605 gct ctg gat gtg atc aca gtg gag ctg tat ccc acc aac cag aga gca      1872
Ala Leu Asp Val Ile Thr Val Glu Leu Tyr Pro Thr Asn Gln Arg Ala
    610                 615                 620 aca gcc ttc ggc att ctc aat gga tta tgc aaa ttt ggc gcc atc ctg      1920
Thr Ala Phe Gly Ile Leu Asn Gly Leu Cys Lys Phe Gly Ala Ile Leu
625                 630                 635                 640 gga aac acc atc ttt gct tct ttt gtt ggg ata acc aaa gtg gtc ccc      1968
Gly Asn Thr Ile Phe Ala Ser Phe Val Gly Ile Thr Lys Val Val Pro
                645                 650                 655 atc ctt ctg gct gct gct tct ctg gtt ggg ggt ggc ctg att gcc ctt      2016
Ile Leu Leu Ala Ala Ala Ser Leu Val Gly Gly Gly Leu Ile Ala Leu
            660                 665                 670 cga ctg cca gag act cga gaa cag gtc ctg atg tga                      2052
Arg Leu Pro Glu Thr Arg Glu Gln Val Leu Met
        675                 680

<210> SEQ ID NO 4
<211> LENGTH: 683
<212> TYPE: PRT
<213> ORGANISM: Homo sapiens

<400> SEQUENCE: 4

Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Glu Leu Ala His Gln Tyr Glu
                85                  90                  95

Thr Ile Met Asp Glu Cys Gly His Gly Arg Phe Gln Trp Ile Leu Phe
                100                 105                 110

Phe Val Leu Gly Leu Ala Leu Met Ala Asp Gly Val Glu Val Phe Val
            115                 120                 125

Val Ser Phe Ala Leu Pro Ser Ala Glu Lys Asp Met Cys Leu Ser Ser
        130                 135                 140

Ser Lys Lys Gly Met Leu Gly Met Ile Val Tyr Leu Gly Met Met Ala
145                 150                 155                 160
```

-continued

```
Gly Ala Phe Ile Leu Gly Gly Leu Ala Asp Lys Leu Gly Arg Lys Arg
                165                 170                 175
Val Leu Ser Met Ser Leu Ala Val Asn Ala Ser Phe Ala Ser Leu Ser
            180                 185                 190
Ser Phe Val Gln Gly Tyr Gly Ala Phe Leu Phe Cys Arg Leu Ile Ser
        195                 200                 205
Gly Ile Gly Ile Gly Gly Ala Leu Pro Ile Val Phe Ala Tyr Phe Ser
    210                 215                 220
Glu Phe Leu Ser Arg Glu Lys Arg Gly Glu His Leu Ser Trp Leu Gly
225                 230                 235                 240
Ile Phe Trp Met Thr Gly Gly Leu Tyr Ala Ser Ala Met Ala Trp Ser
                245                 250                 255
Ile Ile Pro His Tyr Gly Trp Gly Phe Ser Met Gly Thr Asn Tyr His
            260                 265                 270
Phe His Ser Trp Arg Val Phe Val Ile Val Cys Ala Leu Pro Cys Thr
        275                 280                 285
Val Ser Met Val Ala Leu Lys Phe Met Pro Glu Ser Pro Arg Phe Leu
    290                 295                 300
Leu Glu Met Gly Lys His Asp Glu Ala Trp Met Ile Leu Lys Gln Val
305                 310                 315                 320
His Asp Thr Asn Met Arg Ala Lys Gly Thr Pro Glu Lys Val Phe Thr
                325                 330                 335
Val Ser Asn Ile Lys Thr Pro Lys Gln Met Asp Glu Phe Ile Glu Ile
            340                 345                 350
Gln Ser Ser Thr Gly Thr Trp Tyr Gln Arg Trp Leu Val Arg Phe Lys
        355                 360                 365
Thr Ile Phe Lys Gln Val Trp Asp Asn Ala Leu Tyr Cys Val Met Gly
    370                 375                 380
Pro Tyr Arg Met Asn Thr Leu Ile Leu Ala Val Val Trp Phe Ala Met
385                 390                 395                 400
Ala Phe Ser Tyr Tyr Gly Leu Thr Val Trp Phe Pro Asp Met Ile Arg
                405                 410                 415
Tyr Phe Gln Asp Glu Glu Tyr Lys Ser Lys Met Lys Val Phe Phe Gly
            420                 425                 430
Glu His Val Tyr Gly Ala Thr Ile Asn Phe Thr Met Glu Asn Gln Ile
        435                 440                 445
His Gln His Gly Lys Leu Val Asn Asp Lys Phe Thr Arg Met Tyr Phe
    450                 455                 460
Lys His Val Leu Phe Glu Asp Thr Phe Phe Asp Glu Cys Tyr Phe Glu
465                 470                 475                 480
Asp Val Thr Ser Thr Asp Thr Tyr Phe Lys Asn Cys Thr Ile Glu Ser
                485                 490                 495
Thr Ile Phe Tyr Asn Thr Asp Leu Tyr Glu His Lys Phe Ile Asn Cys
            500                 505                 510
Arg Phe Ile Asn Ser Thr Phe Leu Glu Gln Lys Glu Gly Cys His Met
        515                 520                 525
Asp Leu Glu Gln Asp Asn Asp Phe Leu Ile Tyr Leu Val Ser Phe Leu
    530                 535                 540
Gly Ser Leu Ser Val Leu Pro Gly Asn Ile Ile Ser Ala Leu Leu Met
545                 550                 555                 560
Asp Arg Ile Gly Arg Leu Lys Met Ile Gly Gly Ser Met Leu Ile Ser
                565                 570                 575
```

-continued

```
Ala Val Cys Cys Phe Phe Leu Phe Phe Gly Asn Ser Glu Ser Ala Met
            580                 585                 590
Ile Gly Trp Gln Cys Leu Phe Cys Gly Thr Ser Ile Ala Ala Trp Asn
        595                 600                 605
Ala Leu Asp Val Ile Thr Val Glu Leu Tyr Pro Thr Asn Gln Arg Ala
    610                 615                 620
Thr Ala Phe Gly Ile Leu Asn Gly Leu Cys Lys Phe Gly Ala Ile Leu
625                 630                 635                 640
Gly Asn Thr Ile Phe Ala Ser Phe Val Gly Ile Thr Lys Val Val Pro
                645                 650                 655
Ile Leu Leu Ala Ala Ser Leu Val Gly Gly Leu Ile Ala Leu
            660                 665                 670
Arg Leu Pro Glu Thr Arg Glu Gln Val Leu Met
        675                 680
```

<210> SEQ ID NO 5
<211> LENGTH: 2184
<212> TYPE: DNA
<213> ORGANISM: Homo sapiens
<220> FEATURE:
<221> NAME/KEY: CDS
<222> LOCATION: (1)..(2184)
<223> OTHER INFORMATION:

<400> SEQUENCE: 5

```
atg gaa gac tct tac aag gat agg act tca ctg atg aag ggt gcc aag      48
Met Glu Asp Ser Tyr Lys Asp Arg Thr Ser Leu Met Lys Gly Ala Lys
1               5                   10                  15 gac att gcc aga gag gtg aag aaa caa aca gta aag aag gtg aat caa      96
Asp Ile Ala Arg Glu Val Lys Lys Gln Thr Val Lys Lys Val Asn Gln
            20                  25                  30 gct gtg gac cga gcc cag gat gaa tac acc cag agg tcc tac agt cgg     144
Ala Val Asp Arg Ala Gln Asp Glu Tyr Thr Gln Arg Ser Tyr Ser Arg
        35                  40                  45 ttc caa gat gaa gaa gat gat gat gac tac tac ccg gct gga gaa acc     192
Phe Gln Asp Glu Glu Asp Asp Asp Asp Tyr Tyr Pro Ala Gly Glu Thr
    50                  55                  60 tat aat ggt gag gcc aac gat gac gaa ggc tca agt gaa gcc act gag     240
Tyr Asn Gly Glu Ala Asn Asp Asp Glu Gly Ser Ser Glu Ala Thr Glu
65                  70                  75                  80 ggg cat gat gaa gat gat gag atc tat gag ggg gag tat cag ggc atc     288
Gly His Asp Glu Asp Asp Glu Ile Tyr Glu Gly Glu Tyr Gln Gly Ile
                85                  90                  95 ccc agt atg aac caa gcg aag gac agc atc gtg tca gtg ggg cag ccc     336
Pro Ser Met Asn Gln Ala Lys Asp Ser Ile Val Ser Val Gly Gln Pro
            100                 105                 110 aag ggc gat gag tac aag gac cga cgg gag ctg gaa tca gaa agg aga     384
Lys Gly Asp Glu Tyr Lys Asp Arg Arg Glu Leu Glu Ser Glu Arg Arg
        115                 120                 125 gct gac gag gaa gag tta gcc cag cag tat gag ctg ata atc caa gaa     432
Ala Asp Glu Glu Glu Leu Ala Gln Gln Tyr Glu Leu Ile Ile Gln Glu
    130                 135                 140 tgc ggt cat ggt cgt ttt cag tgg gcc ctt ttc ttc gtc ctg ggc atg     480
Cys Gly His Gly Arg Phe Gln Trp Ala Leu Phe Phe Val Leu Gly Met
145                 150                 155                 160 gct ctt atg gca gac ggt gta gag gtg ttt gtc gtt ggc ttc gtg tta     528
Ala Leu Met Ala Asp Gly Val Glu Val Phe Val Val Gly Phe Val Leu
                165                 170                 175 ccc agt gct gag aca gac ctc tgc atc cca aat tca gga tct gga tgg     576
Pro Ser Ala Glu Thr Asp Leu Cys Ile Pro Asn Ser Gly Ser Gly Trp
```

-continued

|  |  |  |  |
|---|---|---|---|
| cta ggc agc ata gtg tac ctc ggg atg atg gtg ggg gcg ttc ttc tgg<br>Leu Gly Ser Ile Val Tyr Leu Gly Met Met Val Gly Ala Phe Phe Trp<br>     195                       200                       205 | 624 |
| gga gga ctg gca gac aaa gtg gga agg aaa cag tct ctt ctg att tgc<br>Gly Gly Leu Ala Asp Lys Val Gly Arg Lys Gln Ser Leu Leu Ile Cys<br>210                       215                       220 | 672 |
| atg tct gtc aac gga ttc ttt gcc ttc ctt tct tca ttt gtc caa ggt<br>Met Ser Val Asn Gly Phe Phe Ala Phe Leu Ser Ser Phe Val Gln Gly<br>225                 230                     235                 240 | 720 |
| tat ggc ttc ttt ctc ttc tgt cgc tta ctt tct gga ttc ggg att gga<br>Tyr Gly Phe Phe Leu Phe Cys Arg Leu Leu Ser Gly Phe Gly Ile Gly<br>                 245                     250                     255 | 768 |
| gga gcc ata ccc act gtg ttc tcg tac ttt gct gaa gtc ctg gcc cgg<br>Gly Ala Ile Pro Thr Val Phe Ser Tyr Phe Ala Glu Val Leu Ala Arg<br>              260                     265                     270 | 816 |
| gaa aag cgg ggc gaa cac ttg agc tgg ctc tgc atg ttc tgg atg atc<br>Glu Lys Arg Gly Glu His Leu Ser Trp Leu Cys Met Phe Trp Met Ile<br>            275                     280                     285 | 864 |
| ggt ggc atc tac gcc tct gcc atg gcc tgg gcc atc atc ccg cac tac<br>Gly Gly Ile Tyr Ala Ser Ala Met Ala Trp Ala Ile Ile Pro His Tyr<br>290                       295                       300 | 912 |
| ggg tgg agc ttc agc atg gga tcg gcc tac cag ttt cac agt tgg cgt<br>Gly Trp Ser Phe Ser Met Gly Ser Ala Tyr Gln Phe His Ser Trp Arg<br>305                 310                     315                 320 | 960 |
| gtg ttt gtc atc gtc tgt gca ctc ccc tgt gtc tcc tcc gtg gtg gcc<br>Val Phe Val Ile Val Cys Ala Leu Pro Cys Val Ser Ser Val Val Ala<br>                 325                     330                     335 | 1008 |
| ctc aca ttc atg cct gaa agc cca cga ttc ttg ttg gag gtt gga aaa<br>Leu Thr Phe Met Pro Glu Ser Pro Arg Phe Leu Leu Glu Val Gly Lys<br>              340                     345                     350 | 1056 |
| cat gat gaa gct tgg atg att ctg aag tta att cat gac acc aac atg<br>His Asp Glu Ala Trp Met Ile Leu Lys Leu Ile His Asp Thr Asn Met<br>            355                     360                     365 | 1104 |
| aga gcc cgg ggt cag cct gag aag gtc ttc acg gta aac aaa ata aaa<br>Arg Ala Arg Gly Gln Pro Glu Lys Val Phe Thr Val Asn Lys Ile Lys<br>370                       375                       380 | 1152 |
| act cct aaa caa ata gat gag ctg att gaa att gag agt gac aca gga<br>Thr Pro Lys Gln Ile Asp Glu Leu Ile Glu Ile Glu Ser Asp Thr Gly<br>385                       390                     395                 400 | 1200 |
| aca tgg tat agg agg tgt ttt gtt cgg atc cgc acc gag ctg tac gga<br>Thr Trp Tyr Arg Arg Cys Phe Val Arg Ile Arg Thr Glu Leu Tyr Gly<br>                 405                     410                     415 | 1248 |
| att tgg ttg act ttt atg aga tgt ttc aac tac cca gtc agg gat aat<br>Ile Trp Leu Thr Phe Met Arg Cys Phe Asn Tyr Pro Val Arg Asp Asn<br>            420                     425                     430 | 1296 |
| aca ata aag ctt aca att gtt tgg ttc acc ctg tcc ttt ggg tac tat<br>Thr Ile Lys Leu Thr Ile Val Trp Phe Thr Leu Ser Phe Gly Tyr Tyr<br>            435                     440                     445 | 1344 |
| gga tta tcc gtt tgg ttc cct gat gtc att aaa cct ctg cag tcc gat<br>Gly Leu Ser Val Trp Phe Pro Asp Val Ile Lys Pro Leu Gln Ser Asp<br>450                       455                       460 | 1392 |
| gaa tat gca ttg cta acc aga aat gtg gag aga gat aaa tat gca aat<br>Glu Tyr Ala Leu Leu Thr Arg Asn Val Glu Arg Asp Lys Tyr Ala Asn<br>465                       470                     475                 480 | 1440 |
| ttc act att aac ttt aca atg gaa aat cag att cat act gga atg gaa<br>Phe Thr Ile Asn Phe Thr Met Glu Asn Gln Ile His Thr Gly Met Glu<br>                 485                     490                     495 | 1488 |
| tac gac aat ggc aga ttc ata ggg gtc aag ttc aaa tct gta act ttc | 1536 |

-continued

```
                Tyr Asp Asn Gly Arg Phe Ile Gly Val Lys Phe Lys Ser Val Thr Phe
                            500                 505                 510 aaa gac tct gtt ttt aag tcc tgc acc ttt gag gat gta act tca gtg            1584
Lys Asp Ser Val Phe Lys Ser Cys Thr Phe Glu Asp Val Thr Ser Val
            515                 520                 525 aac acc tac ttc aag aac tgc aca ttt att gac act gtt ttt gac aac            1632
Asn Thr Tyr Phe Lys Asn Cys Thr Phe Ile Asp Thr Val Phe Asp Asn
            530                 535                 540 aca gat ttt gag cca tat aaa ttc att gac agt gaa ttt aaa aac tgc            1680
Thr Asp Phe Glu Pro Tyr Lys Phe Ile Asp Ser Glu Phe Lys Asn Cys
545                 550                 555                 560 tcg ttt ttt cac aac aag acg gga tgt cag att acc ttt gat gat gac            1728
Ser Phe Phe His Asn Lys Thr Gly Cys Gln Ile Thr Phe Asp Asp Asp
                565                 570                 575 tat agt gcc tac tgg att tat ttt gtc aac ttt ctg ggg aca ttg gca            1776
Tyr Ser Ala Tyr Trp Ile Tyr Phe Val Asn Phe Leu Gly Thr Leu Ala
            580                 585                 590 gta ttg cca ggg aac att gtg tct gct ctg ctg atg gac aga att ggg            1824
Val Leu Pro Gly Asn Ile Val Ser Ala Leu Leu Met Asp Arg Ile Gly
            595                 600                 605 cgc tta aca atg cta ggt ggc tct atg gtg ctt tcg ggg atc agc tgt            1872
Arg Leu Thr Met Leu Gly Gly Ser Met Val Leu Ser Gly Ile Ser Cys
            610                 615                 620 ttc ttc ctt tgg ttc ggc acc agt gaa tcc atg atg ata ggc atg ctg            1920
Phe Phe Leu Trp Phe Gly Thr Ser Glu Ser Met Met Ile Gly Met Leu
625                 630                 635                 640 tgt ctg tac aat gga ttg acc atc tca gcc tgg aac tct ctt gac gtg            1968
Cys Leu Tyr Asn Gly Leu Thr Ile Ser Ala Trp Asn Ser Leu Asp Val
                645                 650                 655 gtc act gtg gaa ctg tac ccc aca gac cgg agg gca aca ggc ttt ggc            2016
Val Thr Val Glu Leu Tyr Pro Thr Asp Arg Arg Ala Thr Gly Phe Gly
            660                 665                 670 ttc tta aat gcg cta tgc aag gca gca gcc gtc ctg gga aac tta ata            2064
Phe Leu Asn Ala Leu Cys Lys Ala Ala Ala Val Leu Gly Asn Leu Ile
            675                 680                 685 ttt ggc tct ctg gtc agc atc acc aaa tca atc ccc atc ctg ctg gct            2112
Phe Gly Ser Leu Val Ser Ile Thr Lys Ser Ile Pro Ile Leu Leu Ala
            690                 695                 700 tct act gtg ctc gtg tgt gga gga ctc gtt ggg ctg tgc ctg cct gac            2160
Ser Thr Val Leu Val Cys Gly Gly Leu Val Gly Leu Cys Leu Pro Asp
705                 710                 715                 720 aca cga acc cag gtt ctg atg taa                                            2184
Thr Arg Thr Gln Val Leu Met
                725
```

<210> SEQ ID NO 6
<211> LENGTH: 727
<212> TYPE: PRT
<213> ORGANISM: Homo sapiens

<400> SEQUENCE: 6

```
Met Glu Asp Ser Tyr Lys Asp Arg Thr Ser Leu Met Lys Gly Ala Lys
1               5                   10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Tyr Tyr Pro Ala Gly Glu Thr
    50                  55                  60
```

-continued

```
Tyr Asn Gly Glu Ala Asn Asp Asp Glu Gly Ser Ser Glu Ala Thr Glu
 65                  70                  75                  80

Gly His Asp Glu Asp Asp Glu Ile Tyr Glu Gly Tyr Gln Gly Ile
                 85                  90                  95

Pro Ser Met Asn Gln Ala Lys Asp Ser Ile Val Ser Val Gly Gln Pro
                100                 105                 110

Lys Gly Asp Glu Tyr Lys Asp Arg Arg Glu Leu Glu Ser Glu Arg Arg
                115                 120                 125

Ala Asp Glu Glu Glu Leu Ala Gln Gln Tyr Glu Leu Ile Ile Gln Glu
            130                 135                 140

Cys Gly His Gly Arg Phe Gln Trp Ala Leu Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Gly Ser Gly Trp
                180                 185                 190

Leu Gly Ser Ile Val Tyr Leu Gly Met Met Val Gly Ala Phe Phe Trp
            195                 200                 205

Gly Gly Leu Ala Asp Lys Val Gly Arg Lys Gln Ser Leu Leu Ile Cys
210                 215                 220

Met Ser Val Asn Gly Phe Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
                260                 265                 270

Glu Lys Arg Gly Glu His Leu Ser Trp Leu Cys Met Phe Trp Met Ile
            275                 280                 285

Gly Gly Ile Tyr Ala Ser Ala Met Ala Trp Ala Ile Ile Pro His Tyr
            290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
            355                 360                 365

Arg Ala Arg Gly Gln Pro Glu Lys Val Phe Thr Val Asn Lys Ile Lys
            370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
                420                 425                 430

Thr Ile Lys Leu Thr Ile Val Trp Phe Thr Leu Ser Phe Gly Tyr Tyr
            435                 440                 445

Gly Leu Ser Val Trp Phe Pro Asp Val Ile Lys Pro Leu Gln Ser Asp
450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
```

```
                       485                 490                 495
Tyr Asp Asn Gly Arg Phe Ile Gly Val Lys Phe Lys Ser Val Thr Phe
                500                 505                 510

Lys Asp Ser Val Phe Lys Ser Cys Thr Phe Glu Asp Val Thr Ser Val
            515                 520                 525

Asn Thr Tyr Phe Lys Asn Cys Thr Phe Ile Asp Thr Val Phe Asp Asn
        530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp
                565                 570                 575

Tyr Ser Ala Tyr Trp Ile Tyr Phe Val Asn Phe Leu Gly Thr Leu Ala
                580                 585                 590

Val Leu Pro Gly Asn Ile Val Ser Ala Leu Leu Met Asp Arg Ile Gly
            595                 600                 605

Arg Leu Thr Met Leu Gly Gly Ser Met Val Leu Ser Gly Ile Ser Cys
        610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
                660                 665                 670

Phe Leu Asn Ala Leu Cys Lys Ala Ala Val Leu Gly Asn Leu Ile
                675                 680                 685

Phe Gly Ser Leu Val Ser Ile Thr Lys Ser Ile Pro Ile Leu Leu Ala
        690                 695                 700

Ser Thr Val Leu Val Cys Gly Gly Leu Val Gly Leu Cys Leu Pro Asp
705                 710                 715                 720

Thr Arg Thr Gln Val Leu Met
                725

<210> SEQ ID NO 7
<211> LENGTH: 1647
<212> TYPE: DNA
<213> ORGANISM: Homo sapiens
<220> FEATURE:
<221> NAME/KEY: CDS
<222> LOCATION: (1)..(1647)
<223> OTHER INFORMATION:

<400> SEQUENCE: 7 atg gag gag gac tta ttc cag cta agg cag ctg ccg gtt gtg aaa ttc       48
Met Glu Glu Asp Leu Phe Gln Leu Arg Gln Leu Pro Val Val Lys Phe
1               5                  10                  15 cgt cgc aca ggc gag agt gca agg tca gag gac gac acg gct tca gga       96
Arg Arg Thr Gly Glu Ser Ala Arg Ser Glu Asp Asp Thr Ala Ser Gly
            20                  25                  30 gag cat gaa gtc cag att gaa ggg gtc cac gtg ggc cta gag gct gtg      144
Glu His Glu Val Gln Ile Glu Gly Val His Val Gly Leu Glu Ala Val
        35                  40                  45 gag ctg gat gat ggg gca gct gtg ccc aag gag ttt gcc aat ccc act      192
Glu Leu Asp Asp Gly Ala Ala Val Pro Lys Glu Phe Ala Asn Pro Thr
    50                  55                  60 gat gat act ttc atg gtg gaa gat gca gtg gaa gcc att ggc ttt gga      240
Asp Asp Thr Phe Met Val Glu Asp Ala Val Glu Ala Ile Gly Phe Gly
65                  70                  75                  80
```

-continued

| | | |
|---|---|---|
| aaa ttt cag tgg aag ctg tct gtt ctc act ggc ttg gct tgg atg gct<br>Lys Phe Gln Trp Lys Leu Ser Val Leu Thr Gly Leu Ala Trp Met Ala<br>                85                        90                        95 | 288 |
| gat gcc atg gag atg atg atc ctc agc atc ctg gca cca cag ctg cat<br>Asp Ala Met Glu Met Met Ile Leu Ser Ile Leu Ala Pro Gln Leu His<br>                   100                      105                      110 | 336 |
| tgc gag tgg agg ctc cca agc tgg cag gtg gca ttg ctg acc tcg gtg<br>Cys Glu Trp Arg Leu Pro Ser Trp Gln Val Ala Leu Leu Thr Ser Val<br>               115                     120                      125 | 384 |
| gtc ttt gta ggc atg atg tcc agc tcc acg ctc tgg gga aat atc tca<br>Val Phe Val Gly Met Met Ser Ser Ser Thr Leu Trp Gly Asn Ile Ser<br>130                       135                      140 | 432 |
| gac cag tac ggc agg aaa aca ggg ctg aag atc agc gtg ctg tgg act<br>Asp Gln Tyr Gly Arg Lys Thr Gly Leu Lys Ile Ser Val Leu Trp Thr<br>145                      150                      155                  160 | 480 |
| ctg tac tat ggc atc ctt agt gca ttt gcg ccc gtg tat agc tgg atc<br>Leu Tyr Tyr Gly Ile Leu Ser Ala Phe Ala Pro Val Tyr Ser Trp Ile<br>                   165                      170                      175 | 528 |
| ctg gtg ctc cgg ggc ctg gtg ggc ttc ggg atc gga gga gtt ccc cag<br>Leu Val Leu Arg Gly Leu Val Gly Phe Gly Ile Gly Gly Val Pro Gln<br>                   180                      185                      190 | 576 |
| tcg gtg acg ctg tat gcc gag ttc ctt ccc atg aaa gcc aga gct aaa<br>Ser Val Thr Leu Tyr Ala Glu Phe Leu Pro Met Lys Ala Arg Ala Lys<br>                   195                      200                      205 | 624 |
| tgt att ttg ctg att gag gta ttc tgg gcc atc ggg aca gtg ttc gag<br>Cys Ile Leu Leu Ile Glu Val Phe Trp Ala Ile Gly Thr Val Phe Glu<br>                 210                      215                      220 | 672 |
| gtc gtc ctg gct gtg ttc gtg atg ccc agc ctg ggc tgg cgt tgg ctg<br>Val Val Leu Ala Val Phe Val Met Pro Ser Leu Gly Trp Arg Trp Leu<br>225                      230                      235                  240 | 720 |
| ctc atc ctc tca gct gtc ccg ctc ctc ttt gcc gtg ctg tgt ttc<br>Leu Ile Leu Ser Ala Val Pro Leu Leu Phe Ala Val Leu Cys Phe<br>                   245                      250                      255 | 768 |
| tgg ctg cct gaa agt gca agg tat gat gtg ctg tca ggg aac cag gaa<br>Trp Leu Pro Glu Ser Ala Arg Tyr Asp Val Leu Ser Gly Asn Gln Glu<br>                   260                      265                      270 | 816 |
| aag gca atc gcc acc tta aag agg ata gca act gaa aac gga gct ccc<br>Lys Ala Ile Ala Thr Leu Lys Arg Ile Ala Thr Glu Asn Gly Ala Pro<br>               275                      280                      285 | 864 |
| atg ccg ctg ggg aaa ctc atc atc tcc aga cag gaa gac cga ggc aaa<br>Met Pro Leu Gly Lys Leu Ile Ile Ser Arg Gln Glu Asp Arg Gly Lys<br>             290                      295                      300 | 912 |
| atg agg gac ctt ttc aca ccc cat ttt aga tgg aca act ttg ctg ctg<br>Met Arg Asp Leu Phe Thr Pro His Phe Arg Trp Thr Thr Leu Leu Leu<br>305                      310                      315                  320 | 960 |
| tgg ttt ata tgg ttt tcc aat gca ttc tct tac tac ggg tta gtt cta<br>Trp Phe Ile Trp Phe Ser Asn Ala Phe Ser Tyr Tyr Gly Leu Val Leu<br>                   325                      330                      335 | 1008 |
| ctc acc aca gaa ctc ttc cag gca gga gat gtc tgc ggc atc tcc agt<br>Leu Thr Thr Glu Leu Phe Gln Ala Gly Asp Val Cys Gly Ile Ser Ser<br>                   340                      345                      350 | 1056 |
| cgg aag aag gct gta gag gca aaa tgc agc ctg gcc tgc gag tac ctg<br>Arg Lys Lys Ala Val Glu Ala Lys Cys Ser Leu Ala Cys Glu Tyr Leu<br>             355                      360                      365 | 1104 |
| agt gag gag gat tac atg gac ttg ctg tgg acc acc ctc tct gag ttt<br>Ser Glu Glu Asp Tyr Met Asp Leu Leu Trp Thr Thr Leu Ser Glu Phe<br>             370                      375                      380 | 1152 |
| cca ggt gtc ctt gtg act ctg tgg att att gac cgc ctg ggg cgc aag<br>Pro Gly Val Leu Val Thr Leu Trp Ile Ile Asp Arg Leu Gly Arg Lys<br>385                      390                      395                  400 | 1200 |

-continued

```
aag acc atg gcc ctg tgc ttt gtc atc ttc tcc ttc tgc agc ctc ctg    1248
Lys Thr Met Ala Leu Cys Phe Val Ile Phe Ser Phe Cys Ser Leu Leu
            405                 410                 415 ctg ttt atc tgt gtt gga aga aat gtg ctc act ctg tta ctc ttc att    1296
Leu Phe Ile Cys Val Gly Arg Asn Val Leu Thr Leu Leu Leu Phe Ile
        420                 425                 430 gca aga gcg ttt att tct gga ggc ttt caa gcg gca tat gtt tac aca    1344
Ala Arg Ala Phe Ile Ser Gly Gly Phe Gln Ala Ala Tyr Val Tyr Thr
    435                 440                 445 cct gag gtc tac ccc acg gca acg cgg gcc ctc ggc ctg ggc acc tgc    1392
Pro Glu Val Tyr Pro Thr Ala Thr Arg Ala Leu Gly Leu Gly Thr Cys
450                 455                 460 agc ggc atg gca aga gtg ggt gct ctc atc act ccg ttc atc gcc cag    1440
Ser Gly Met Ala Arg Val Gly Ala Leu Ile Thr Pro Phe Ile Ala Gln
465                 470                 475                 480 gtg atg ctg gaa tcc tct gtg tac ctg act ctg gca gtt tac agt ggc    1488
Val Met Leu Glu Ser Ser Val Tyr Leu Thr Leu Ala Val Tyr Ser Gly
                485                 490                 495 tgc tgc ctc ctg gct gcc ctg gcc tcc tgc ttt ttg ccc att gag acc    1536
Cys Cys Leu Leu Ala Ala Leu Ala Ser Cys Phe Leu Pro Ile Glu Thr
            500                 505                 510 aaa ggc cga gga ctg cag gag tcc agc cac cgg gag tgg ggc cag gag    1584
Lys Gly Arg Gly Leu Gln Glu Ser Ser His Arg Glu Trp Gly Gln Glu
        515                 520                 525 atg gtc ggc cga gga atg cac ggt gca ggt gtt acc agg tcg aac tct    1632
Met Val Gly Arg Gly Met His Gly Ala Gly Val Thr Arg Ser Asn Ser
    530                 535                 540 ggc tct cag gaa tag                                                1647
Gly Ser Gln Glu
545
```

<210> SEQ ID NO 8
<211> LENGTH: 548
<212> TYPE: PRT
<213> ORGANISM: Homo sapiens

<400> SEQUENCE: 8

```
Met Glu Glu Asp Leu Phe Gln Leu Arg Gln Leu Pro Val Val Lys Phe
1               5                   10                  15

Arg Arg Thr Gly Glu Ser Ala Arg Ser Glu Asp Asp Thr Ala Ser Gly
            20                  25                  30

Glu His Glu Val Gln Ile Glu Gly Val His Val Gly Leu Glu Ala Val
        35                  40                  45

Glu Leu Asp Asp Gly Ala Ala Val Pro Lys Glu Phe Ala Asn Pro Thr
    50                  55                  60

Asp Asp Thr Phe Met Val Glu Asp Ala Val Glu Ala Ile Gly Phe Gly
65                  70                  75                  80

Lys Phe Gln Trp Lys Leu Ser Val Leu Thr Gly Leu Ala Trp Met Ala
                85                  90                  95

Asp Ala Met Glu Met Met Ile Leu Ser Ile Leu Ala Pro Gln Leu His
            100                 105                 110

Cys Glu Trp Arg Leu Pro Ser Trp Gln Val Ala Leu Leu Thr Ser Val
        115                 120                 125

Val Phe Val Gly Met Met Ser Ser Ser Thr Leu Trp Gly Asn Ile Ser
    130                 135                 140

Asp Gln Tyr Gly Arg Lys Thr Gly Leu Lys Ile Ser Val Leu Trp Thr
145                 150                 155                 160
```

```
Leu Tyr Tyr Gly Ile Leu Ser Ala Phe Ala Pro Val Tyr Ser Trp Ile
                165                 170                 175

Leu Val Leu Arg Gly Leu Val Gly Phe Gly Ile Gly Gly Val Pro Gln
            180                 185                 190

Ser Val Thr Leu Tyr Ala Glu Phe Leu Pro Met Lys Ala Arg Ala Lys
        195                 200                 205

Cys Ile Leu Leu Ile Glu Val Phe Trp Ala Ile Gly Thr Val Phe Glu
210                 215                 220

Val Val Leu Ala Val Phe Val Met Pro Ser Leu Gly Trp Arg Trp Leu
225                 230                 235                 240

Leu Ile Leu Ser Ala Val Pro Leu Leu Phe Ala Val Leu Cys Phe
                245                 250                 255

Trp Leu Pro Glu Ser Ala Arg Tyr Asp Val Leu Ser Gly Asn Gln Glu
            260                 265                 270

Lys Ala Ile Ala Thr Leu Lys Arg Ile Ala Thr Glu Asn Gly Ala Pro
        275                 280                 285

Met Pro Leu Gly Lys Leu Ile Ile Ser Arg Gln Glu Asp Arg Gly Lys
290                 295                 300

Met Arg Asp Leu Phe Thr Pro His Phe Arg Trp Thr Thr Leu Leu Leu
305                 310                 315                 320

Trp Phe Ile Trp Phe Ser Asn Ala Phe Ser Tyr Tyr Gly Leu Val Leu
                325                 330                 335

Leu Thr Thr Glu Leu Phe Gln Ala Gly Asp Val Cys Gly Ile Ser Ser
            340                 345                 350

Arg Lys Lys Ala Val Glu Ala Lys Cys Ser Leu Ala Cys Glu Tyr Leu
        355                 360                 365

Ser Glu Glu Asp Tyr Met Asp Leu Leu Trp Thr Thr Leu Ser Glu Phe
370                 375                 380

Pro Gly Val Leu Val Thr Leu Trp Ile Ile Asp Arg Leu Gly Arg Lys
385                 390                 395                 400

Lys Thr Met Ala Leu Cys Phe Val Ile Phe Ser Phe Cys Ser Leu Leu
                405                 410                 415

Leu Phe Ile Cys Val Gly Arg Asn Val Leu Thr Leu Leu Leu Phe Ile
            420                 425                 430

Ala Arg Ala Phe Ile Ser Gly Gly Phe Gln Ala Ala Tyr Val Tyr Thr
        435                 440                 445

Pro Glu Val Tyr Pro Thr Ala Thr Arg Ala Leu Gly Leu Gly Thr Cys
450                 455                 460

Ser Gly Met Ala Arg Val Gly Ala Leu Ile Thr Pro Phe Ile Ala Gln
465                 470                 475                 480

Val Met Leu Glu Ser Ser Val Tyr Leu Thr Leu Ala Val Tyr Ser Gly
                485                 490                 495

Cys Cys Leu Leu Ala Ala Leu Ala Ser Cys Phe Leu Pro Ile Glu Thr
            500                 505                 510

Lys Gly Arg Gly Leu Gln Glu Ser Ser His Arg Glu Trp Gly Gln Glu
        515                 520                 525

Met Val Gly Arg Gly Met His Gly Ala Gly Val Thr Arg Ser Asn Ser
530                 535                 540

Gly Ser Gln Glu
545

<210> SEQ ID NO 9
<211> LENGTH: 3844
<212> TYPE: DNA
```

<213> ORGANISM: Rattus norvegicus
<220> FEATURE:
<221> NAME/KEY: CDS
<222> LOCATION: (400)..(2628)
<223> OTHER INFORMATION:

<400> SEQUENCE: 9

| | |
|---|---|
| cctcagccct gtggctggac ccctccctc acccggggac tccctgaccc ggggaaccaa | 60 |
| gctcaggtct ccagagcctc ccagaagaaa aataggcagc cctccctgaa atatcttggc | 120 |
| tcctcagttt atcctttcca acctggctcc cccttcccag ttcccctccc tactccctgt | 180 |
| ctccctcccc aactcaccct actgaactgg gtgcagagca aagccctttt cgcccttttc | 240 |
| cccatctgga cttctctggc cagttcctct tagtccgatc ccaaagacac tggaacacat | 300 |
| ttctaaaggg tcttcttgat ccctccaatt cattgagcaa agggctgaaa agaagcaga | 360 |
| gagtaaggta gagccagtga ctcgccccca agccccatc atg gaa gaa ggc ttt | 414 |
|                                                                                             Met Glu Glu Gly Phe<br>                                                                                            1               5 | |
| cga gac cga gca gcg ttc atc cgt ggg gcc aaa gac att gcc aag gaa<br>Arg Asp Arg Ala Ala Phe Ile Arg Gly Ala Lys Asp Ile Ala Lys Glu<br>                  10                      15                      20 | 462 |
| gtt aag aag cac gcg gcc aag aag gtg gtg aag ggt ctc gac aga gtc<br>Val Lys Lys His Ala Ala Lys Lys Val Val Lys Gly Leu Asp Arg Val<br> 25                        30                      35 | 510 |
| cag gat gaa tat tcc cga agg tcc tac tcc cgc ttt gag gag gag gag<br>Gln Asp Glu Tyr Ser Arg Arg Ser Tyr Ser Arg Phe Glu Glu Glu Glu<br>        40                      45                      50 | 558 |
| gat gat gat gac ttc cct gcc cct gct gac ggc tat tac cgc gga gaa<br>Asp Asp Asp Asp Phe Pro Ala Pro Ala Asp Gly Tyr Tyr Arg Gly Glu<br>55                        60                      65 | 606 |
| ggg gcc cag gat gag gag gaa ggt ggc gct tcc agt gat gcc act gag<br>Gly Ala Gln Asp Glu Glu Gly Gly Ala Ser Ser Asp Ala Thr Glu<br>70                     75                      80                      85 | 654 |
| ggc cac gat gag gat gat gag atc tac gag gga gaa tat cag ggc atc<br>Gly His Asp Glu Asp Asp Glu Ile Tyr Glu Gly Glu Tyr Gln Gly Ile<br>           90                      95                      100 | 702 |
| ccc cgg gca gag tct ggg ggc aaa ggc gaa cgg atg gca gat ggg gca<br>Pro Arg Ala Glu Ser Gly Gly Lys Gly Glu Arg Met Ala Asp Gly Ala<br>        105                      110                      115 | 750 |
| ccc ctg gct gga gtg aga ggg ggc tta agt gat ggg gag ggt ccc cct<br>Pro Leu Ala Gly Val Arg Gly Gly Leu Ser Asp Gly Glu Gly Pro Pro<br>120                     125                      130 | 798 |
| ggg ggt cgc ggg gag gcg cag cgg cgt aaa gat cgg gaa gaa ttg gct<br>Gly Gly Arg Gly Glu Ala Gln Arg Arg Lys Asp Arg Glu Glu Leu Ala<br>135                     140                      145 | 846 |
| cag cag tat gag acc atc ctc cgg gag tgc ggc cat ggt cgc ttc cag<br>Gln Gln Tyr Glu Thr Ile Leu Arg Glu Cys Gly His Gly Arg Phe Gln<br>150                     155                      160                      165 | 894 |
| tgg aca ctc tac ttc gtg ctg ggt ctg gcg ctg atg gcc gat ggt gta<br>Trp Thr Leu Tyr Phe Val Leu Gly Leu Ala Leu Met Ala Asp Gly Val<br>                  170                      175                      180 | 942 |
| gag gtc ttt gtg gtg ggc ttt gtg ctg ccc agt gct gag aaa gat atg<br>Glu Val Phe Val Val Gly Phe Val Leu Pro Ser Ala Glu Lys Asp Met<br>              185                      190                      195 | 990 |
| tgc ctg tcg gac tcc aac aaa ggc atg cta ggc ctc att gtg tac ctg<br>Cys Leu Ser Asp Ser Asn Lys Gly Met Leu Gly Leu Ile Val Tyr Leu<br>200                     205                      210 | 1038 |
| ggc atg atg gtg ggg gcc ttc ctc tgg gga ggc ctg gct gat cgg ctg<br>Gly Met Met Val Gly Ala Phe Leu Trp Gly Gly Leu Ala Asp Arg Leu<br>        215                      220                      225 | 1086 |

-continued

| | | |
|---|---|---|
| ggt cgg aga cag tgt ctg ctc atc tcg ctc tca gtc aac agc gtc ttc<br>Gly Arg Arg Gln Cys Leu Leu Ile Ser Leu Ser Val Asn Ser Val Phe<br>230                    235                     240                    245 | 1134 |
| gct ttc ttc tca tcc ttc gtc cag ggt tat ggc acc ttc ctt ttc tgc<br>Ala Phe Phe Ser Ser Phe Val Gln Gly Tyr Gly Thr Phe Leu Phe Cys<br>                    250                     255                     260 | 1182 |
| cgc ctc ctt tct ggg gtt ggg att ggt ggt tcc atc ccc att gtc ttc<br>Arg Leu Leu Ser Gly Val Gly Ile Gly Gly Ser Ile Pro Ile Val Phe<br>             265                    270                     275 | 1230 |
| tcc tat ttt tcg gag ttt ctg gcc cag gag aaa cgt ggg gag cat ttg<br>Ser Tyr Phe Ser Glu Phe Leu Ala Gln Glu Lys Arg Gly Glu His Leu<br>                   280                     285                    290 | 1278 |
| agc tgg ctc tgt atg ttc tgg atg att ggt ggc gtg tat gca gct gca<br>Ser Trp Leu Cys Met Phe Trp Met Ile Gly Gly Val Tyr Ala Ala Ala<br>295                    300                     305 | 1326 |
| atg gcc tgg gcc atc atc ccc cac tat ggg tgg agt ttc cag atg ggc<br>Met Ala Trp Ala Ile Ile Pro His Tyr Gly Trp Ser Phe Gln Met Gly<br>310                      315                     320                    325 | 1374 |
| tct gct tac cag ttc cac agc tgg agg gtc ttt gtc ctc gtc ttt gcc<br>Ser Ala Tyr Gln Phe His Ser Trp Arg Val Phe Val Leu Val Phe Ala<br>                   330                     335                    340 | 1422 |
| ttt ccc tct gtg ttt gcc atc ggg gct ctg act acg cag ccg gag agt<br>Phe Pro Ser Val Phe Ala Ile Gly Ala Leu Thr Thr Gln Pro Glu Ser<br>             345                    350                     355 | 1470 |
| ccc cgc ttc ttc tta gag aat ggg aag cac gat gag gcc tgg atg gtg<br>Pro Arg Phe Phe Leu Glu Asn Gly Lys His Asp Glu Ala Trp Met Val<br>                   360                     365                    370 | 1518 |
| ctg aag cag gtt cat gac acc aac atg cga gcc aag ggc cat cct gag<br>Leu Lys Gln Val His Asp Thr Asn Met Arg Ala Lys Gly His Pro Glu<br>375                    380                    385 | 1566 |
| cga gtc ttc tca gta acc cac att aaa acg att cat cag gag gat gaa<br>Arg Val Phe Ser Val Thr His Ile Lys Thr Ile His Gln Glu Asp Glu<br>390                    395                    400                    405 | 1614 |
| ttg att gag atc cag tca gac aca gga acc tgg tac cag cgc tgg gga<br>Leu Ile Glu Ile Gln Ser Asp Thr Gly Thr Trp Tyr Gln Arg Trp Gly<br>                   410                     415                    420 | 1662 |
| gtg cgg gct ttg agc ctg ggg ggt cag gtt tgg ggg aac ttc ctc tcc<br>Val Arg Ala Leu Ser Leu Gly Gly Gln Val Trp Gly Asn Phe Leu Ser<br>             425                    430                     435 | 1710 |
| tgc ttc agt cca gag tac cgg cgc atc act ctg atg atg atg ggg gta<br>Cys Phe Ser Pro Glu Tyr Arg Arg Ile Thr Leu Met Met Met Gly Val<br>                   440                     445                    450 | 1758 |
| tgg ttc acc atg tcc ttc agc tac tac ggt ttg act gtc tgg ttt ccc<br>Trp Phe Thr Met Ser Phe Ser Tyr Tyr Gly Leu Thr Val Trp Phe Pro<br>455                    460                    465 | 1806 |
| gac atg atc cgc cat ctc cag gct gtg gac tat gca gcc cga acc aaa<br>Asp Met Ile Arg His Leu Gln Ala Val Asp Tyr Ala Ala Arg Thr Lys<br>470                    475                    480                    485 | 1854 |
| gtg ttc cca ggg gag cgc gtg gag cac gtg aca ttt aac ttc aca ctg<br>Val Phe Pro Gly Glu Arg Val Glu His Val Thr Phe Asn Phe Thr Leu<br>                   490                     495                    500 | 1902 |
| gag aat cag atc cac cga ggg gga cag tac ttc aat gac aag ttc atc<br>Glu Asn Gln Ile His Arg Gly Gly Gln Tyr Phe Asn Asp Lys Phe Ile<br>             505                    510                     515 | 1950 |
| ggg ctg cgt ctg aag tca gtg tcc ttt gag gat tcc ctg ttt gag gaa<br>Gly Leu Arg Leu Lys Ser Val Ser Phe Glu Asp Ser Leu Phe Glu Glu<br>                   520                     525                    530 | 1998 |
| tgt tac ttt gaa gat gtc aca tcc agc aac aca ttc ttc cgc aac tgc<br>Cys Tyr Phe Glu Asp Val Thr Ser Ser Asn Thr Phe Phe Arg Asn Cys | 2046 |

-continued

|     | 535 |     |     |     | 540 |     |     |     | 545 |     |     |      |
| --- | --- | --- | --- | --- | --- | --- | --- | --- | --- | --- | --- | ---- |
| aca | ttc | atc | aac | acc | gtg | ttc | tac | aac | acg | gac | ctg | ttt gag tac aag | 2094 |
| Thr | Phe | Ile | Asn | Thr | Val | Phe | Tyr | Asn | Thr | Asp | Leu | Phe Glu Tyr Lys |
| 550 |     |     |     |     | 555 |     |     |     | 560 |     |     | 565 |

```
aca ttc atc aac acc gtg ttc tac aac acg gac ctg ttt gag tac aag      2094
Thr Phe Ile Asn Thr Val Phe Tyr Asn Thr Asp Leu Phe Glu Tyr Lys
550                 555                 560                 565 ttc gtg aac agc cgc ctg gtg aac agc aca ttc ctg cac aat aag gaa      2142
Phe Val Asn Ser Arg Leu Val Asn Ser Thr Phe Leu His Asn Lys Glu
                570                 575                 580 ggt tgc cca cta gat gtg aca ggg acg ggc gaa ggt gcc tac atg gtg      2190
Gly Cys Pro Leu Asp Val Thr Gly Thr Gly Glu Gly Ala Tyr Met Val
            585                 590                 595 tac ttt gtc agc ttc ttg ggg aca ctg gct gtg ctc cct gga aat att      2238
Tyr Phe Val Ser Phe Leu Gly Thr Leu Ala Val Leu Pro Gly Asn Ile
        600                 605                 610 gtg tct gct ctg ctc atg gac aag att ggc agg ctc aga atg ctt gct      2286
Val Ser Ala Leu Leu Met Asp Lys Ile Gly Arg Leu Arg Met Leu Ala
    615                 620                 625 ggt tcc agt gtg ttg tcc tgt gtt tcc tgc ttc ttc ctg tct ttt ggg      2334
Gly Ser Ser Val Leu Ser Cys Val Ser Cys Phe Phe Leu Ser Phe Gly
630                 635                 640                 645 aac agt gag tca gcc atg atc gct ctg ctc tgc ctt ttt ggg gga gtc      2382
Asn Ser Glu Ser Ala Met Ile Ala Leu Leu Cys Leu Phe Gly Gly Val
                650                 655                 660 agt att gca tcc tgg aac gcg ctg gac gtg ctg act gtt gaa ctc tac      2430
Ser Ile Ala Ser Trp Asn Ala Leu Asp Val Leu Thr Val Glu Leu Tyr
            665                 670                 675 cct tcc gac aag agg acg acg gcc ttc ggc ttc ctg aat gcc ctg tgt      2478
Pro Ser Asp Lys Arg Thr Thr Ala Phe Gly Phe Leu Asn Ala Leu Cys
        680                 685                 690 aag ctg gca gct gta ctg ggc atc agc atc ttc acg tcc ttt gtg gga      2526
Lys Leu Ala Ala Val Leu Gly Ile Ser Ile Phe Thr Ser Phe Val Gly
    695                 700                 705 atc acc aag gcc gct ccc atc ctc ttc gcc tca gct gcg ctt gcc ctt      2574
Ile Thr Lys Ala Ala Pro Ile Leu Phe Ala Ser Ala Ala Leu Ala Leu
710                 715                 720                 725 ggt agc tct ctg gct ctg aag ctg cct gag acc cgg gga cag gtg ctg      2622
Gly Ser Ser Leu Ala Leu Lys Leu Pro Glu Thr Arg Gly Gln Val Leu
                730                 735                 740 cag tga gggatgggg agtgtctcag gggctttagg gatggcaggc acactgtgac       2678
Gln caataatttc ttttatccct accctgccct gctgtcctgg tcctactccg tgtttggtgt   2738
cttagctgtg tgcctgtgtg catgtgtgtg accctgacgg gcaggggcta cggggagggt   2798 cccttttgtcc catgtttggg aggagggact ccccacctgc tgccaccctc aactttgcac  2858
aaggagaagg ctgagctgca tccttctctc cctcagtgtt agcaggggtg gggacgactg   2918
tttctctgct ccaggtgttc cagaatttct gcctttccca tcattccctc cgcctaggcc   2978
ctggtgaacc acaggtatgg agttatagtg ggggctgagg cttggaccaa agaacttct    3038 tgagtgggag cctcccaagg atgctgggga gtagcaataa accttagcct ccgttttcac   3098
ctcaattcag ctacaagtg tgaagcctgg attttatgga attagttttc tgattccttat   3158 ttatatgtaa gttctgaggc agcttagctg gactgtgtgt ggatgtatac atacactcat   3218
atgtgtgtgt gtgtgcgccg cgtgcgtgtg cgtgtgtgta tgtgtgccat ggggtagggg   3278
taccactata ctgttcaatt ataagccaag agtagtagtt tcagtgagca cacacacaac   3338
actgtttttc tatcgtaact cccagaatct tgtacctgtg ttggggctgc aggcagaagt   3398
ccttggtcag gctgggtgta gccctgcaat cttggggac ctgagggcac ctgacaagga    3458
```

-continued

```
ctttctcctt cctctagaga ggttctaccc actagccaca gccctcccat ctgacctgtc    3518
cacacaggca gtgtatcaga ggaaagaaag ggaaaataac caggcacaca tggtcaaacc    3578
agcaggtctg aaagcacaag aagctggggc aggggcagga agcagggtc catcccctaa     3638 cccttctcaa aaaggctggg tcgtgaggga cccctaatgc agggacctga agcctcagtt    3698
tccccatctt gccctccac agaacagcct ctgtaggtag agctgccccc cgtcctaccc     3758
tactcttgtg gctgctttct ttggtactct tcccactccc accgtagctg tgacgtgttg    3818 tagttttag ctgtttgtaa aatgtt                                          3844
```

<210> SEQ ID NO 10
<211> LENGTH: 742
<212> TYPE: PRT
<213> ORGANISM: Rattus norvegicus

<400> SEQUENCE: 10

```
Met Glu Glu Gly Phe Arg Asp Arg Ala Ala Phe Ile Arg Gly Ala Lys
  1               5                  10                  15

Asp Ile Ala Lys Glu Val Lys Lys His Ala Ala Lys Lys Val Val Lys
             20                  25                  30

Gly Leu Asp Arg Val Gln Asp Glu Tyr Ser Arg Arg Ser Tyr Ser Arg
         35                  40                  45

Phe Glu Glu Glu Asp Asp Asp Phe Pro Ala Pro Ala Asp Gly
     50                  55                  60

Tyr Tyr Arg Gly Glu Gly Ala Gln Asp Glu Glu Gly Gly Ala Ser
 65                  70                  75                  80

Ser Asp Ala Thr Glu Gly His Asp Glu Asp Asp Glu Ile Tyr Glu Gly
                 85                  90                  95

Glu Tyr Gln Gly Ile Pro Arg Ala Glu Ser Gly Gly Lys Gly Glu Arg
            100                 105                 110

Met Ala Asp Gly Ala Pro Leu Ala Gly Val Arg Gly Gly Leu Ser Asp
        115                 120                 125

Gly Glu Gly Pro Pro Gly Gly Arg Gly Glu Ala Gln Arg Arg Lys Asp
    130                 135                 140

Arg Glu Glu Leu Ala Gln Gln Tyr Glu Thr Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser
            180                 185                 190

Ala Glu Lys Asp Met Cys Leu Ser Asp Ser Asn Lys Gly Met Leu Gly
        195                 200                 205

Leu Ile Val Tyr Leu Gly Met Met Val Gly Ala Phe Leu Trp Gly Gly
    210                 215                 220

Leu Ala Asp Arg Leu Gly Arg Arg Gln Cys Leu Leu Ile Ser Leu Ser
225                 230                 235                 240

Val Asn Ser Val Phe Ala Phe Ser Ser Phe Val Gln Gly Tyr Gly
                245                 250                 255

Thr Phe Leu Phe Cys Arg Leu Leu Ser Gly Val Gly Ile Gly Gly Ser
            260                 265                 270

Ile Pro Ile Val Phe Ser Tyr Phe Ser Glu Phe Leu Ala Gln Glu Lys
        275                 280                 285

Arg Gly Glu His Leu Ser Trp Leu Cys Met Phe Trp Met Ile Gly Gly
    290                 295                 300
```

-continued

```
Val Tyr Ala Ala Ala Met Ala Trp Ala Ile Ile Pro His Tyr Gly Trp
305                 310                 315                 320

Ser Phe Gln Met Gly Ser Ala Tyr Gln Phe His Ser Trp Arg Val Phe
            325                 330                 335

Val Leu Val Phe Ala Phe Pro Ser Val Phe Ala Ile Gly Ala Leu Thr
        340                 345                 350

Thr Gln Pro Glu Ser Pro Arg Phe Phe Leu Glu Asn Gly Lys His Asp
    355                 360                 365

Glu Ala Trp Met Val Leu Lys Gln Val His Asp Thr Asn Met Arg Ala
370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Ser Pro Glu Tyr Arg Arg Ile Thr Leu
        435                 440                 445

Met Met Met Gly Val Trp Phe Thr Met Ser Phe Ser Tyr Tyr Gly Leu
450                 455                 460

Thr Val Trp Phe Pro Asp Met Ile Arg His Leu Gln Ala Val Asp Tyr
465                 470                 475                 480

Ala Ala Arg Thr Lys Val Phe Pro Gly Glu Arg Val Glu His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Val Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Leu Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
```

-continued

```
                    725                 730                 735
Arg Gly Gln Val Leu Gln
            740

<210> SEQ ID NO 11
<211> LENGTH: 2052
<212> TYPE: DNA
<213> ORGANISM: Rattus norvegicus
<220> FEATURE:
<221> NAME/KEY: CDS
<222> LOCATION: (1)..(2052)
<223> OTHER INFORMATION:

<400> SEQUENCE: 11 atg gat gac tac agg tat cgg gac aac tat gag ggc tat gcc cct aat      48
Met Asp Asp Tyr Arg Tyr Arg Asp Asn Tyr Glu Gly Tyr Ala Pro Asn
1               5                   10                  15 gat ggc tac tac cgg ggc aat gag cag aac ccg gaa gaa gat gca cag      96
Asp Gly Tyr Tyr Arg Gly Asn Glu Gln Asn Pro Glu Glu Asp Ala Gln
            20                  25                  30 agc gat gtt aca gaa ggc cac gat gaa gag gat gag atc tat gag ggc     144
Ser Asp Val Thr Glu Gly His Asp Glu Glu Asp Glu Ile Tyr Glu Gly
        35                  40                  45 gag tac caa ggc atc cct cat cca gat gat gtc aag tct aag cag act     192
Glu Tyr Gln Gly Ile Pro His Pro Asp Asp Val Lys Ser Lys Gln Thr
    50                  55                  60 aag atg gca ccg tcc aga gca gat ggc ctt cgg ggc cag gca gac ctg     240
Lys Met Ala Pro Ser Arg Ala Asp Gly Leu Arg Gly Gln Ala Asp Leu
65                  70                  75                  80 atg gct gag aga atg gaa gat gag gag cag ctc gct cac cag tac gag     288
Met Ala Glu Arg Met Glu Asp Glu Glu Gln Leu Ala His Gln Tyr Glu
                85                  90                  95 acc atc att gat gag tgt ggc cat ggg cgc ttc cag tgg acc ctc ttt     336
Thr Ile Ile Asp Glu Cys Gly His Gly Arg Phe Gln Trp Thr Leu Phe
            100                 105                 110 ttc gtc ttg gtc ttg gcc ttg atg gct gac gga gtg gaa gtg ttt gtg     384
Phe Val Leu Val Leu Ala Leu Met Ala Asp Gly Val Glu Val Phe Val
        115                 120                 125 gtg agc ttt gct ctg cca agt gca gag aaa gat atg tgt ctg tca agt     432
Val Ser Phe Ala Leu Pro Ser Ala Glu Lys Asp Met Cys Leu Ser Ser
    130                 135                 140 tcc aag aaa gga atg ctc ggg ctg att gtc tac cta gga atg atg gca     480
Ser Lys Lys Gly Met Leu Gly Leu Ile Val Tyr Leu Gly Met Met Ala
145                 150                 155                 160 gga gcc ttc atc ctg ggg ggc ctg gct gat aaa ctg gga agg aag aag     528
Gly Ala Phe Ile Leu Gly Gly Leu Ala Asp Lys Leu Gly Arg Lys Lys
                165                 170                 175 gtc ctc agc atg tcc ttg gct atc aat gct tcc ttt gcc tcc ctc tcc     576
Val Leu Ser Met Ser Leu Ala Ile Asn Ala Ser Phe Ala Ser Leu Ser
            180                 185                 190 tcc ttc gtg cag gga tat gga gct ttc ctc ttc tgc aga ctc atc tca     624
Ser Phe Val Gln Gly Tyr Gly Ala Phe Leu Phe Cys Arg Leu Ile Ser
        195                 200                 205 ggc ata ggt att ggg ggc tcc ctg cca att gtt ttt gcc tac ttt tct     672
Gly Ile Gly Ile Gly Gly Ser Leu Pro Ile Val Phe Ala Tyr Phe Ser
    210                 215                 220 gag ttc tta tca cgg gag aaa cgc ggt gag cat ctc agc tgg ctg ggt     720
Glu Phe Leu Ser Arg Glu Lys Arg Gly Glu His Leu Ser Trp Leu Gly
225                 230                 235                 240 atc ttc tgg atg act ggg ggc atc tac gca tct gcc atg gcc tgg agc     768
Ile Phe Trp Met Thr Gly Gly Ile Tyr Ala Ser Ala Met Ala Trp Ser
```

-continued

|  |  |  |  |  |  |  |  |  |  |  |  |  |  |  |  |
|---|---|---|---|---|---|---|---|---|---|---|---|---|---|---|---|
|  |  |  | 245 |  |  |  | 250 |  |  |  | 255 |  |  |  |  |
| atc | att | cca | cac | tat | ggc | tgg | ggc | ttc | agc | atg | gga | acc | aat | tat | cac | 816 |
| Ile | Ile | Pro | His | Tyr | Gly | Trp | Gly | Phe | Ser | Met | Gly | Thr | Asn | Tyr | His |  |
|  |  |  | 260 |  |  |  | 265 |  |  |  | 270 |  |  |  |  |  |
| ttc | cac | agc | tgg | aga | gtg | ttt | gtc | atc | gtc | tgt | gct | ctg | cct | gcc | act | 864 |
| Phe | His | Ser | Trp | Arg | Val | Phe | Val | Ile | Val | Cys | Ala | Leu | Pro | Ala | Thr |  |
|  |  | 275 |  |  |  |  | 280 |  |  |  |  | 285 |  |  |  |  |
| gtg | tcc | atg | gtg | gcc | ctg | aag | ttc | atg | cca | gaa | agc | ccc | agg | ttc | ctg | 912 |
| Val | Ser | Met | Val | Ala | Leu | Lys | Phe | Met | Pro | Glu | Ser | Pro | Arg | Phe | Leu |  |
|  | 290 |  |  |  |  | 295 |  |  |  |  | 300 |  |  |  |  |  |
| ctg | gag | atg | ggc | aag | cat | gat | gaa | gcc | tgg | atg | att | ctc | aag | caa | gtc | 960 |
| Leu | Glu | Met | Gly | Lys | His | Asp | Glu | Ala | Trp | Met | Ile | Leu | Lys | Gln | Val |  |
| 305 |  |  |  |  | 310 |  |  |  |  | 315 |  |  |  |  | 320 |  |
| cat | gac | acc | aac | atg | aga | gct | aag | ggg | acc | cct | gag | aag | gtg | ttc | acg | 1008 |
| His | Asp | Thr | Asn | Met | Arg | Ala | Lys | Gly | Thr | Pro | Glu | Lys | Val | Phe | Thr |  |
|  |  |  |  | 325 |  |  |  |  | 330 |  |  |  |  | 335 |  |  |
| gtt | tcc | cac | atc | aaa | act | ccc | aag | caa | atg | gat | gaa | ttc | att | gag | atc | 1056 |
| Val | Ser | His | Ile | Lys | Thr | Pro | Lys | Gln | Met | Asp | Glu | Phe | Ile | Glu | Ile |  |
|  |  |  | 340 |  |  |  | 345 |  |  |  | 350 |  |  |  |  |  |
| cag | agt | tca | aca | ggg | act | tgg | tac | cag | cgc | tgg | ttg | gtc | agg | ttc | atg | 1104 |
| Gln | Ser | Ser | Thr | Gly | Thr | Trp | Tyr | Gln | Arg | Trp | Leu | Val | Arg | Phe | Met |  |
|  |  | 355 |  |  |  |  | 360 |  |  |  |  | 365 |  |  |  |  |
| acc | att | ttc | aaa | cag | gtg | tgg | gat | aac | gcc | ttg | tac | tgt | gtg | atg | gga | 1152 |
| Thr | Ile | Phe | Lys | Gln | Val | Trp | Asp | Asn | Ala | Leu | Tyr | Cys | Val | Met | Gly |  |
|  | 370 |  |  |  |  | 375 |  |  |  |  | 380 |  |  |  |  |  |
| ccc | tac | aga | atg | aac | acc | ctg | att | ctg | gct | gtg | gtc | tgg | ttc | acc | atg | 1200 |
| Pro | Tyr | Arg | Met | Asn | Thr | Leu | Ile | Leu | Ala | Val | Val | Trp | Phe | Thr | Met |  |
| 385 |  |  |  |  | 390 |  |  |  |  | 395 |  |  |  |  | 400 |  |
| gcc | tta | agt | tac | tat | ggc | ctg | aca | gtg | tgg | ttc | ccc | gac | atg | atc | cgg | 1248 |
| Ala | Leu | Ser | Tyr | Tyr | Gly | Leu | Thr | Val | Trp | Phe | Pro | Asp | Met | Ile | Arg |  |
|  |  |  |  | 405 |  |  |  |  | 410 |  |  |  |  | 415 |  |  |
| tat | ttc | cag | gat | gaa | gaa | tat | aag | tct | aaa | atg | aag | gtg | ttt | ttt | ggt | 1296 |
| Tyr | Phe | Gln | Asp | Glu | Glu | Tyr | Lys | Ser | Lys | Met | Lys | Val | Phe | Phe | Gly |  |
|  |  |  | 420 |  |  |  | 425 |  |  |  | 430 |  |  |  |  |  |
| gag | cac | gtg | cat | ggc | gcc | aca | atc | aac | ttc | acc | atg | gaa | aac | cag | atc | 1344 |
| Glu | His | Val | His | Gly | Ala | Thr | Ile | Asn | Phe | Thr | Met | Glu | Asn | Gln | Ile |  |
|  |  | 435 |  |  |  |  | 440 |  |  |  |  | 445 |  |  |  |  |
| cac | caa | cat | ggg | aag | ctt | gtg | aac | gat | aag | ttc | ata | aag | atg | tac | ttt | 1392 |
| His | Gln | His | Gly | Lys | Leu | Val | Asn | Asp | Lys | Phe | Ile | Lys | Met | Tyr | Phe |  |
|  | 450 |  |  |  |  | 455 |  |  |  |  | 460 |  |  |  |  |  |
| aag | cat | gtc | ctc | ttt | gag | gac | aca | ttc | ttt | gac | aaa | tgc | tat | ttt | gaa | 1440 |
| Lys | His | Val | Leu | Phe | Glu | Asp | Thr | Phe | Phe | Asp | Lys | Cys | Tyr | Phe | Glu |  |
| 465 |  |  |  |  | 470 |  |  |  |  | 475 |  |  |  |  | 480 |  |
| gat | gtg | aca | tcc | aca | gat | act | tat | ttc | aag | aac | tgc | acc | att | gaa | tcg | 1488 |
| Asp | Val | Thr | Ser | Thr | Asp | Thr | Tyr | Phe | Lys | Asn | Cys | Thr | Ile | Glu | Ser |  |
|  |  |  |  | 485 |  |  |  |  | 490 |  |  |  |  | 495 |  |  |
| act | acc | ttc | tac | aac | aca | gac | ctc | tac | aaa | cac | aag | ttc | att | gac | tgt | 1536 |
| Thr | Thr | Phe | Tyr | Asn | Thr | Asp | Leu | Tyr | Lys | His | Lys | Phe | Ile | Asp | Cys |  |
|  |  |  |  | 500 |  |  |  |  | 505 |  |  |  |  | 510 |  |  |
| cgg | ttt | atc | aat | tcc | acc | ttt | ctg | gag | cag | aag | gag | ggc | tgc | cac | atg | 1584 |
| Arg | Phe | Ile | Asn | Ser | Thr | Phe | Leu | Glu | Gln | Lys | Glu | Gly | Cys | His | Met |  |
|  |  |  | 515 |  |  |  | 520 |  |  |  | 525 |  |  |  |  |  |
| gac | ttt | gaa | gag | gac | aat | gat | ttt | ctg | att | tac | ctc | gtc | agc | ttc | ctc | 1632 |
| Asp | Phe | Glu | Glu | Asp | Asn | Asp | Phe | Leu | Ile | Tyr | Leu | Val | Ser | Phe | Leu |  |
|  | 530 |  |  |  |  | 535 |  |  |  |  | 540 |  |  |  |  |  |
| ggc | agc | ctg | tct | gtc | ttg | cct | ggg | aac | ata | att | tct | gcc | ctg | ctc | atg | 1680 |
| Gly | Ser | Leu | Ser | Val | Leu | Pro | Gly | Asn | Ile | Ile | Ser | Ala | Leu | Leu | Met |  |
| 545 |  |  |  |  | 550 |  |  |  |  | 555 |  |  |  |  | 560 |  |
| gac | aga | atc | gga | aga | ctt | aag | atg | att | ggt | ggc | tcc | atg | ctc | atc | tct | 1728 |

```
Asp Arg Ile Gly Arg Leu Lys Met Ile Gly Gly Ser Met Leu Ile Ser
                565                 570                 575 gca gtc tgc tgc ttc ttc ctg ttt ttt ggc aac agc gag tct gcg atg       1776
Ala Val Cys Cys Phe Phe Leu Phe Phe Gly Asn Ser Glu Ser Ala Met
            580                 585                 590 atc ggc tgg caa tgc ctg ttc tgt ggg acc agc att gca gcc tgg aat       1824
Ile Gly Trp Gln Cys Leu Phe Cys Gly Thr Ser Ile Ala Ala Trp Asn
        595                 600                 605 gct ctg gat gtg atc aca gta gag ctg tat ccc acc aac cag agg gcc       1872
Ala Leu Asp Val Ile Thr Val Glu Leu Tyr Pro Thr Asn Gln Arg Ala
    610                 615                 620 act gcc ttc ggc atc ctc aat gga ctg tgc aaa ctt ggt gcc atc ctg       1920
Thr Ala Phe Gly Ile Leu Asn Gly Leu Cys Lys Leu Gly Ala Ile Leu
625                 630                 635                 640 gga aac act atc ttt gct tct ttt gtt ggg atc acc aaa gtg gtc ccc       1968
Gly Asn Thr Ile Phe Ala Ser Phe Val Gly Ile Thr Lys Val Val Pro
                645                 650                 655 atc ctt ctg gct gct gct tct ctg gtt gga ggt ggc ttg gtt gcc ctt       2016
Ile Leu Leu Ala Ala Ala Ser Leu Val Gly Gly Gly Leu Val Ala Leu
            660                 665                 670 cga ctg cca gag act cga gag cag gtc ctg atg tga                       2052
Arg Leu Pro Glu Thr Arg Glu Gln Val Leu Met
        675                 680
```

<210> SEQ ID NO 12
<211> LENGTH: 683
<212> TYPE: PRT
<213> ORGANISM: Rattus norvegicus

<400> SEQUENCE: 12

```
Met Asp Asp Tyr Arg Tyr Arg Asp Asn Tyr Glu Gly Tyr Ala Pro Asn
1               5                   10                  15

Asp Gly Tyr Tyr Arg Gly Asn Glu Gln Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ser Lys Gln Thr
    50                  55                  60

Lys Met Ala Pro Ser Arg Ala Asp Gly Leu Arg Gly Gln Ala Asp Leu
65                  70                  75                  80

Met Ala Glu Arg Met Glu Asp Glu Gln Leu Ala His Gln Tyr Glu
                85                  90                  95

Thr Ile Ile Asp Glu Cys Gly His Gly Arg Phe Gln Trp Thr Leu Phe
            100                 105                 110

Phe Val Leu Val Leu Ala Leu Met Ala Asp Gly Val Glu Val Phe Val
        115                 120                 125

Val Ser Phe Ala Leu Pro Ser Ala Glu Lys Asp Met Cys Leu Ser Ser
    130                 135                 140

Ser Lys Lys Gly Met Leu Gly Leu Ile Val Tyr Leu Gly Met Met Ala
145                 150                 155                 160

Gly Ala Phe Ile Leu Gly Gly Leu Ala Asp Lys Leu Gly Arg Lys Lys
                165                 170                 175

Val Leu Ser Met Ser Leu Ala Ile Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ser Leu Pro Ile Val Phe Ala Tyr Phe Ser
```

-continued

```
            210                 215                 220
Glu Phe Leu Ser Arg Glu Lys Arg Gly Glu His Leu Ser Trp Leu Gly
225                 230                 235                 240

Ile Phe Trp Met Thr Gly Gly Ile Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Ile Val Cys Ala Leu Pro Ala Thr
        275                 280                 285

Val Ser Met Val Ala Leu Lys Phe Met Pro Glu Ser Pro Arg Phe Leu
290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser His Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Met
        355                 360                 365

Thr Ile Phe Lys Gln Val Trp Asp Asn Ala Leu Tyr Cys Val Met Gly
370                 375                 380

Pro Tyr Arg Met Asn Thr Leu Ile Leu Ala Val Val Trp Phe Thr Met
385                 390                 395                 400

Ala Leu Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430

Glu His Val His Gly Ala Thr Ile Asn Phe Thr Met Glu Asn Gln Ile
        435                 440                 445

His Gln His Gly Lys Leu Val Asn Asp Lys Phe Ile Lys Met Tyr Phe
    450                 455                 460

Lys His Val Leu Phe Glu Asp Thr Phe Phe Asp Lys Cys Tyr Phe Glu
465                 470                 475                 480

Asp Val Thr Ser Thr Asp Thr Tyr Phe Lys Asn Cys Thr Ile Glu Ser
                485                 490                 495

Thr Thr Phe Tyr Asn Thr Asp Leu Tyr Lys His Lys Phe Ile Asp Cys
            500                 505                 510

Arg Phe Ile Asn Ser Thr Phe Leu Glu Gln Lys Glu Gly Cys His Met
        515                 520                 525

Asp Phe Glu Glu Asp Asn Asp Phe Leu Ile Tyr Leu Val Ser Phe Leu
530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Ser Met Leu Ile Ser
                565                 570                 575

Ala Val Cys Cys Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Leu Gly Ala Ile Leu
625                 630                 635                 640
```

-continued

```
Gly Asn Thr Ile Phe Ala Ser Phe Val Gly Ile Thr Lys Val Val Pro
            645                 650                 655

Ile Leu Leu Ala Ala Ala Ser Leu Val Gly Gly Gly Leu Val Ala Leu
            660                 665                 670

Arg Leu Pro Glu Thr Arg Glu Gln Val Leu Met
            675                 680

<210> SEQ ID NO 13
<211> LENGTH: 2622
<212> TYPE: DNA
<213> ORGANISM: Rattus norvegicus
<220> FEATURE:
<221> NAME/KEY: CDS
<222> LOCATION: (224)..(2407)
<223> OTHER INFORMATION:

<400> SEQUENCE: 13
gcgcgctgca ggaagagtgg cagaccgaag cggcctcggg ctgcaaacgg aggggcgctc       60
gcgcggcgac ggctgcaggg ctgacaccgc tcagggcagg ggggtcccag gcggctggaa      120
cgctctattc tgaactgtga gtggatgatg ctgttgcagc caagctgctg aacacactcc      180
gtggactctt ccctgctgtg ccttgcccat cggccgagat aaa atg gaa gac tcc       235
                                               Met Glu Asp Ser
                                                 1 tac aag gat agg act tca ctg atg aag ggc gcc aag gac att gcc aaa       283
Tyr Lys Asp Arg Thr Ser Leu Met Lys Gly Ala Lys Asp Ile Ala Lys
  5                  10                  15                  20 gag gtg aag aag caa aca gtg aag aag gtg aac cag gca gtg gac cgg       331
Glu Val Lys Lys Gln Thr Val Lys Lys Val Asn Gln Ala Val Asp Arg
                  25                  30                  35 gcc cag gat gaa tac acc cag cgg tcc tac agt cga ttc cag gat gaa       379
Ala Gln Asp Glu Tyr Thr Gln Arg Ser Tyr Ser Arg Phe Gln Asp Glu
              40                  45                  50 gat gat gat gat gac tac tac cca cct gga gaa acc tac agt ggg gag       427
Asp Asp Asp Asp Asp Tyr Tyr Pro Pro Gly Glu Thr Tyr Ser Gly Glu
          55                  60                  65 gcc aat gat gat gaa ggc tca agt gaa gcc act gag ggt cac gat gaa       475
Ala Asn Asp Asp Glu Gly Ser Ser Glu Ala Thr Glu Gly His Asp Glu
      70                  75                  80 gaa gac gag atc tat gaa ggg gaa tac cag ggc atc ccc agc acg aac       523
Glu Asp Glu Ile Tyr Glu Gly Glu Tyr Gln Gly Ile Pro Ser Thr Asn
 85                  90                  95                 100 caa ggg aag gac agc ata gtg tct gta gga caa ccc aaa gga gat gag       571
Gln Gly Lys Asp Ser Ile Val Ser Val Gly Gln Pro Lys Gly Asp Glu
                 105                 110                 115 tac aag gac cgc aga gag ctg gag tca gag agg agg gct gat gag gag       619
Tyr Lys Asp Arg Arg Glu Leu Glu Ser Glu Arg Arg Ala Asp Glu Glu
             120                 125                 130 gag ctc gcc cag cag tat gag ctg ata atc caa gag tgt ggc cat ggc       667
Glu Leu Ala Gln Gln Tyr Glu Leu Ile Ile Gln Glu Cys Gly His Gly
         135                 140                 145 cgt ttc cag tgg gcc ctt ttc ttc gtc ctg ggc atg gct ctc atg gca       715
Arg Phe Gln Trp Ala Leu Phe Phe Val Leu Gly Met Ala Leu Met Ala
     150                 155                 160 gac ggc gtg gag gtg ttt gtg gtg ggc ttt gtg tta ccc agt gca gag       763
Asp Gly Val Glu Val Phe Val Val Gly Phe Val Leu Pro Ser Ala Glu
165                 170                 175                 180 aca gac cta tgc ata ccg aat tca gga tct gga tgg cta ggc agc ata       811
Thr Asp Leu Cys Ile Pro Asn Ser Gly Ser Gly Trp Leu Gly Ser Ile
                 185                 190                 195
```

```
gtg tac ctc ggg atg atg gtg ggg gcg ttc ttc tgg gga gga ctg gca     859
Val Tyr Leu Gly Met Met Val Gly Ala Phe Phe Trp Gly Gly Leu Ala
        200                 205                 210 gac aaa gtg gga agg aag cag tct ctt ctg att tgc atg tcc gtc aac     907
Asp Lys Val Gly Arg Lys Gln Ser Leu Leu Ile Cys Met Ser Val Asn
            215                 220                 225 gga ttc ttt gcc ttc ctt tct tca ttt gtc caa ggt tac ggc ttc ttt     955
Gly Phe Phe Ala Phe Leu Ser Ser Phe Val Gln Gly Tyr Gly Phe Phe
    230                 235                 240 ctc ctc tgt cgt ttg ctt tca gga ttc ggg att gga ggc gcc att ccc    1003
Leu Leu Cys Arg Leu Leu Ser Gly Phe Gly Ile Gly Gly Ala Ile Pro
245                 250                 255                 260 act gtg ttc tcc tac ttt gct gaa gtc ctg gcc cgg gag aag cgc ggt    1051
Thr Val Phe Ser Tyr Phe Ala Glu Val Leu Ala Arg Glu Lys Arg Gly
                265                 270                 275 gag cac ctc agt tgg ctc tgc atg ttc tgg atg att ggc ggt atc tat    1099
Glu His Leu Ser Trp Leu Cys Met Phe Trp Met Ile Gly Gly Ile Tyr
            280                 285                 290 gct tca gcc atg gcc tgg gcc atc atc ccc cac tat ggg tgg agc ttc    1147
Ala Ser Ala Met Ala Trp Ala Ile Ile Pro His Tyr Gly Trp Ser Phe
    295                 300                 305 agc atg ggc tca gcc tac cag ttc cac agc tgg cgc gtc ttc gtc atc    1195
Ser Met Gly Ser Ala Tyr Gln Phe His Ser Trp Arg Val Phe Val Ile
310                 315                 320 gtc tgt gcc ctc ccg tgc gtc tcc tcg gtg gtg gcc ctc acc ttc atg    1243
Val Cys Ala Leu Pro Cys Val Ser Ser Val Val Ala Leu Thr Phe Met
325                 330                 335                 340 ccc gaa agc cct cgg ttc ttg ctg gag gta gga aaa cat gat gaa gcc    1291
Pro Glu Ser Pro Arg Phe Leu Leu Glu Val Gly Lys His Asp Glu Ala
                345                 350                 355 tgg atg att ctg aag cta att cat gat acc aac atg aga gcc cgg ggc    1339
Trp Met Ile Leu Lys Leu Ile His Asp Thr Asn Met Arg Ala Arg Gly
            360                 365                 370 cag cca gag aag gtc ttc acg gta aat aaa atc aag act ccc aag caa    1387
Gln Pro Glu Lys Val Phe Thr Val Asn Lys Ile Lys Thr Pro Lys Gln
    375                 380                 385 ata gat gag ctg att gag att gag agc gac aca gga acc tgg tac cgg    1435
Ile Asp Glu Leu Ile Glu Ile Glu Ser Asp Thr Gly Thr Trp Tyr Arg
390                 395                 400 agg tgt ttt gtt cgg atc cgc aca gaa ctg tac gga att tgg ttg act    1483
Arg Cys Phe Val Arg Ile Arg Thr Glu Leu Tyr Gly Ile Trp Leu Thr
405                 410                 415                 420 ttt atg aga tgc ttc aac tac ccg gtc agg gaa aac acc ata aag ctt    1531
Phe Met Arg Cys Phe Asn Tyr Pro Val Arg Glu Asn Thr Ile Lys Leu
                425                 430                 435 acg att gtt tgg ttc acc ctg tcc ttt ggg tac tat gga ctg tcc gtt    1579
Thr Ile Val Trp Phe Thr Leu Ser Phe Gly Tyr Tyr Gly Leu Ser Val
            440                 445                 450 tgg ttc cca gat gtc att aaa cac ctc cag tct gac gag tac gcc ctg    1627
Trp Phe Pro Asp Val Ile Lys His Leu Gln Ser Asp Glu Tyr Ala Leu
    455                 460                 465 ctg act cgg aat gtg cag aag gat aaa tat gca aac ttt agc att aac    1675
Leu Thr Arg Asn Val Gln Lys Asp Lys Tyr Ala Asn Phe Ser Ile Asn
470                 475                 480 ttc acc atg gaa aac cag gtc cac acc gga atg gaa tat gac aat ggc    1723
Phe Thr Met Glu Asn Gln Val His Thr Gly Met Glu Tyr Asp Asn Gly
485                 490                 495                 500 agg ttc ctc gga gtc aaa ttc aaa tcg gta acc ttc aag gat tca gtg    1771
Arg Phe Leu Gly Val Lys Phe Lys Ser Val Thr Phe Lys Asp Ser Val
```

-continued

```
                  505                 510                 515
ttt aag tcc tgc acc ttt gac gat gtg acc tca gtc aac acc tac ttc    1819
Phe Lys Ser Cys Thr Phe Asp Asp Val Thr Ser Val Asn Thr Tyr Phe
            520                 525                 530 aag aac tgc acg ttt att gat acc ctt ttt gag aac aca gat ttt gag    1867
Lys Asn Cys Thr Phe Ile Asp Thr Leu Phe Glu Asn Thr Asp Phe Glu
        535                 540                 545 ccc tat aaa ttc ata gac agc gag ttt caa aac tgc tcg ttt ctt cac    1915
Pro Tyr Lys Phe Ile Asp Ser Glu Phe Gln Asn Cys Ser Phe Leu His
    550                 555                 560 aat aag acg gga tgt cag att act ttt gac gac gac tac agt gcc tac    1963
Asn Lys Thr Gly Cys Gln Ile Thr Phe Asp Asp Asp Tyr Ser Ala Tyr
565                 570                 575                 580 tgg att tac ttt gtc aac ttt ctc ggg aca ttg gca gtg tta cca gga    2011
Trp Ile Tyr Phe Val Asn Phe Leu Gly Thr Leu Ala Val Leu Pro Gly
                585                 590                 595 aat atc gtg tct gct ctc ctg atg gac agg atc ggg cgc tta acg atg    2059
Asn Ile Val Ser Ala Leu Leu Met Asp Arg Ile Gly Arg Leu Thr Met
            600                 605                 610 cta ggt ggc tcc atg gtg ctc tcg ggg atc agc tgc ttc ttc ctg tgg    2107
Leu Gly Gly Ser Met Val Leu Ser Gly Ile Ser Cys Phe Phe Leu Trp
        615                 620                 625 ttt ggc acc agc gaa tcc atg atg ata ggc atg ctg tgc ttg tac aac    2155
Phe Gly Thr Ser Glu Ser Met Met Ile Gly Met Leu Cys Leu Tyr Asn
    630                 635                 640 gga ctg acc atc tca gcg tgg aac tct ctt gat gta gtc acg gtg gaa    2203
Gly Leu Thr Ile Ser Ala Trp Asn Ser Leu Asp Val Val Thr Val Glu
645                 650                 655                 660 cta tac ccc aca gac cgg aga gca acg ggc ttt ggc ttc ttg aac gca    2251
Leu Tyr Pro Thr Asp Arg Arg Ala Thr Gly Phe Gly Phe Leu Asn Ala
                665                 670                 675 ctc tgt aaa gca gcg gcc gtc ctg gga aac tta ata ttc ggc tcc ttg    2299
Leu Cys Lys Ala Ala Ala Val Leu Gly Asn Leu Ile Phe Gly Ser Leu
            680                 685                 690 gtc agc atc acc aaa gca atc cct atc ctg ctg gct tcc acc gtg ctc    2347
Val Ser Ile Thr Lys Ala Ile Pro Ile Leu Leu Ala Ser Thr Val Leu
        695                 700                 705 gtg tgt gga gga ctc gtg ggg ctg cgc ctg ccc gac aca aga acc cag    2395
Val Cys Gly Gly Leu Val Gly Leu Arg Leu Pro Asp Thr Arg Thr Gln
    710                 715                 720 gtt ctg atg tga caaaagccat tctcttctct caccatgggt cagccctatt        2447
Val Leu Met
725 gcctgactca aggcttcaga gttttatgt atagaaaggt ggccaagtat cagaactcaa   2507 acttttgctg tgacgtaaat gtagctgtgt attgtccccg ccagtgtgat ttgcagggtc  2567 ctcccccctcc ccgcgcctt gttatctttt cctaattgtg atgttcctgc ttccg       2622
```

<210> SEQ ID NO 14
<211> LENGTH: 727
<212> TYPE: PRT
(213) ORGANISM: Rattus norvegicus

<400> SEQUENCE: 14

```
Met Glu Asp Ser Tyr Lys Asp Arg Thr Ser Leu Met Lys Gly Ala Lys
1               5                   10                  15

Asp Ile Ala Lys Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
```

```
                35                  40                  45
Phe Gln Asp Glu Asp Asp Asp Asp Tyr Tyr Pro Pro Gly Glu Thr
        50                  55                  60
Tyr Ser Gly Glu Ala Asn Asp Asp Glu Gly Ser Ser Glu Ala Thr Glu
65                  70                  75                  80
Gly His Asp Glu Glu Asp Glu Ile Tyr Glu Gly Tyr Gln Gly Ile
                85                  90                  95
Pro Ser Thr Asn Gln Gly Lys Asp Ser Ile Val Ser Val Gly Gln Pro
                100                 105                 110
Lys Gly Asp Glu Tyr Lys Asp Arg Arg Glu Leu Glu Ser Glu Arg Arg
                115                 120                 125
Ala Asp Glu Glu Glu Leu Ala Gln Gln Tyr Glu Leu Ile Ile Gln Glu
    130                 135                 140
Cys Gly His Gly Arg Phe Gln Trp Ala Leu Phe Val Leu Gly Met
145                 150                 155                 160
Ala Leu Met Ala Asp Gly Val Glu Val Phe Val Val Gly Phe Val Leu
                165                 170                 175
Pro Ser Ala Glu Thr Asp Leu Cys Ile Pro Asn Ser Gly Ser Gly Trp
                180                 185                 190
Leu Gly Ser Ile Val Tyr Leu Gly Met Met Val Gly Ala Phe Phe Trp
                195                 200                 205
Gly Gly Leu Ala Asp Lys Val Gly Arg Lys Gln Ser Leu Leu Ile Cys
                210                 215                 220
Met Ser Val Asn Gly Phe Phe Ala Phe Leu Ser Ser Phe Val Gln Gly
225                 230                 235                 240
Tyr Gly Phe Phe Leu Leu Cys Arg Leu Leu Ser Gly Phe Gly Ile Gly
                245                 250                 255
Gly Ala Ile Pro Thr Val Phe Ser Tyr Phe Ala Glu Val Leu Ala Arg
                260                 265                 270
Glu Lys Arg Gly Glu His Leu Ser Trp Leu Cys Met Phe Trp Met Ile
                275                 280                 285
Gly Gly Ile Tyr Ala Ser Ala Met Ala Trp Ala Ile Ile Pro His Tyr
                290                 295                 300
Gly Trp Ser Phe Ser Met Gly Ser Ala Tyr Gln Phe His Ser Trp Arg
305                 310                 315                 320
Val Phe Val Ile Val Cys Ala Leu Pro Cys Val Ser Ser Val Val Ala
                325                 330                 335
Leu Thr Phe Met Pro Glu Ser Pro Arg Phe Leu Leu Glu Val Gly Lys
                340                 345                 350
His Asp Glu Ala Trp Met Ile Leu Lys Leu Ile His Asp Thr Asn Met
                355                 360                 365
Arg Ala Arg Gly Gln Pro Glu Lys Val Phe Thr Val Asn Lys Ile Lys
    370                 375                 380
Thr Pro Lys Gln Ile Asp Glu Leu Ile Glu Ile Glu Ser Asp Thr Gly
385                 390                 395                 400
Thr Trp Tyr Arg Arg Cys Phe Val Arg Ile Arg Thr Glu Leu Tyr Gly
                405                 410                 415
Ile Trp Leu Thr Phe Met Arg Cys Phe Asn Tyr Pro Val Arg Glu Asn
                420                 425                 430
Thr Ile Lys Leu Thr Ile Val Trp Phe Thr Leu Ser Phe Gly Tyr Tyr
                435                 440                 445
Gly Leu Ser Val Trp Phe Pro Asp Val Ile Lys His Leu Gln Ser Asp
    450                 455                 460
```

```
Glu Tyr Ala Leu Leu Thr Arg Asn Val Gln Lys Asp Lys Tyr Ala Asn
465                 470                 475                 480

Phe Ser Ile Asn Phe Thr Met Glu Asn Gln Val His Thr Gly Met Glu
            485                 490                 495

Tyr Asp Asn Gly Arg Phe Leu Gly Val Lys Phe Lys Ser Val Thr Phe
                500                 505                 510

Lys Asp Ser Val Phe Lys Ser Cys Thr Phe Asp Asp Val Thr Ser Val
            515                 520                 525

Asn Thr Tyr Phe Lys Asn Cys Thr Phe Ile Asp Thr Leu Phe Glu Asn
            530                 535                 540

Thr Asp Phe Glu Pro Tyr Lys Phe Ile Asp Ser Glu Phe Gln Asn Cys
545                 550                 555                 560

Ser Phe Leu His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
                580                 585                 590

Val Leu Pro Gly Asn Ile Val Ser Ala Leu Leu Met Asp Arg Ile Gly
                595                 600                 605

Arg Leu Thr Met Leu Gly Gly Ser Met Val Leu Ser Gly Ile Ser Cys
            610                 615                 620

Phe Phe Leu Trp Phe Gly Thr Ser Glu Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
                660                 665                 670

Phe Leu Asn Ala Leu Cys Lys Ala Ala Ala Val Leu Gly Asn Leu Ile
            675                 680                 685

Phe Gly Ser Leu Val Ser Ile Thr Lys Ala Ile Pro Ile Leu Leu Ala
            690                 695                 700

Ser Thr Val Leu Val Cys Gly Gly Leu Val Gly Leu Arg Leu Pro Asp
705                 710                 715                 720

Thr Arg Thr Gln Val Leu Met
                725

<210> SEQ ID NO 15
<211> LENGTH: 1647
<212> TYPE: DNA
<213> ORGANISM: Rattus norvegicus
<220> FEATURE:
<221> NAME/KEY: CDS
<222> LOCATION: (1)..(1647)
<223> OTHER INFORMATION:

<400> SEQUENCE: 15 atg gag gag gac ctg ttc cag ctc agg cag ttg ccg gtg gtg aaa ttc     48
Met Glu Glu Asp Leu Phe Gln Leu Arg Gln Leu Pro Val Val Lys Phe
1               5                   10                  15 cgc cgc aca gga gag agc gca cgg tca gag gac gac gcg gct tcc ggg     96
Arg Arg Thr Gly Glu Ser Ala Arg Ser Glu Asp Asp Ala Ala Ser Gly
            20                  25                  30 gaa cat gat gtt cag att gag ggg gtc cga gtg ggc cta gaa gct gtc    144
Glu His Asp Val Gln Ile Glu Gly Val Arg Val Gly Leu Glu Ala Val
        35                  40                  45 gag ctg gat gat gga gca gct gtc ccc aag gag ttt gcc aat ccc act    192
Glu Leu Asp Asp Gly Ala Ala Val Pro Lys Glu Phe Ala Asn Pro Thr
50                  55                  60
```

-continued

```
gat gac act ttc atg gtc gaa gat gcg gtg gaa gcc att ggg ttc gga      240
Asp Asp Thr Phe Met Val Glu Asp Ala Val Glu Ala Ile Gly Phe Gly
 65              70                  75                  80 aga ttc cag tgg aag ctc tct gtt ctc acc ggc ttg gct tgg atg gcg      288
Arg Phe Gln Trp Lys Leu Ser Val Leu Thr Gly Leu Ala Trp Met Ala
                 85                  90                  95 gac gcc atg gag atg atg att ctg agc atc ctg gcg cct cag ctg cac      336
Asp Ala Met Glu Met Met Ile Leu Ser Ile Leu Ala Pro Gln Leu His
            100                 105                 110 tgc gag tgg cga ctc ccc agc tgg cag gtg gcg ctg ctg act tcg gtg      384
Cys Glu Trp Arg Leu Pro Ser Trp Gln Val Ala Leu Leu Thr Ser Val
        115                 120                 125 gtc ttc att ggt atg atg tcc agt tct acg ctc tgg gga aac atc tcg      432
Val Phe Ile Gly Met Met Ser Ser Ser Thr Leu Trp Gly Asn Ile Ser
130                 135                 140 gat cag tat ggc agg aaa aca ggg ctg aag atc agt gtg ttc tgg acc      480
Asp Gln Tyr Gly Arg Lys Thr Gly Leu Lys Ile Ser Val Phe Trp Thr
145                 150                 155                 160 ctg tac tac ggc atc ctc agc gct ttc gcg cca gtg tat agc tgg atc      528
Leu Tyr Tyr Gly Ile Leu Ser Ala Phe Ala Pro Val Tyr Ser Trp Ile
                165                 170                 175 ctg gtg ctc cga ggc ctc gtg ggc ttt ggg att gga ggg gtg cct cag      576
Leu Val Leu Arg Gly Leu Val Gly Phe Gly Ile Gly Gly Val Pro Gln
            180                 185                 190 tcg gtg acc ctg tac gcc gag ttc ctc ccc atg aag gcc aga gcc aag      624
Ser Val Thr Leu Tyr Ala Glu Phe Leu Pro Met Lys Ala Arg Ala Lys
        195                 200                 205 tgc att ttg ctg att gag gtt ttc tgg gcc atc ggg acc gtg ttc gag      672
Cys Ile Leu Leu Ile Glu Val Phe Trp Ala Ile Gly Thr Val Phe Glu
210                 215                 220 gtg ctt ctg gct gtg ttt gtg atg ccc agc ctg ggc tgg cgc tgg ctg      720
Val Leu Leu Ala Val Phe Val Met Pro Ser Leu Gly Trp Arg Trp Leu
225                 230                 235                 240 ctg ctg ctg tcg gcc gct cca cta ctt gtc ttt gct gtt ctg tgt ttc      768
Leu Leu Leu Ser Ala Ala Pro Leu Leu Val Phe Ala Val Leu Cys Phe
                245                 250                 255 tgg ctg cca gag agt gct agg tac gat gtg ctg tct ggg aac cag gaa      816
Trp Leu Pro Glu Ser Ala Arg Tyr Asp Val Leu Ser Gly Asn Gln Glu
            260                 265                 270 aag gcg att gct acc tta aag cgg atc gca aca gaa aat gga gcc ccc      864
Lys Ala Ile Ala Thr Leu Lys Arg Ile Ala Thr Glu Asn Gly Ala Pro
        275                 280                 285 atg cct ctg ggg aag ctc atc atc tcc aga cag gaa gac cga ggc aaa      912
Met Pro Leu Gly Lys Leu Ile Ile Ser Arg Gln Glu Asp Arg Gly Lys
290                 295                 300 atg agg gac ctt ttc aca ccc cac ttt cgt tgg aca act ctg ctg ctg      960
Met Arg Asp Leu Phe Thr Pro His Phe Arg Trp Thr Thr Leu Leu Leu
305                 310                 315                 320 tgg ttt ata tgg ttc tcc aat gcc ttc tct tat tac ggc ttg gtt ctg     1008
Trp Phe Ile Trp Phe Ser Asn Ala Phe Ser Tyr Tyr Gly Leu Val Leu
                325                 330                 335 ctc acc aca gaa ctc ttc cag gcc gga gat gtt tgc agc atc tcc agc     1056
Leu Thr Thr Glu Leu Phe Gln Ala Gly Asp Val Cys Ser Ile Ser Ser
            340                 345                 350 cgg aag aag gcg gtg gaa gcc aaa tgc agc ctg gct tgt gag tac ctc     1104
Arg Lys Lys Ala Val Glu Ala Lys Cys Ser Leu Ala Cys Glu Tyr Leu
        355                 360                 365 agc aaa gag gat tac atg gac ctg ctg tgg acc acc ctg tct gag ttc     1152
Ser Lys Glu Asp Tyr Met Asp Leu Leu Trp Thr Thr Leu Ser Glu Phe
```

-continued

```
            370                 375                 380
cca ggt gtc ctt gtg act ctg tgg gtc atc gac cgc ctg ggc cgc aag      1200
Pro Gly Val Leu Val Thr Leu Trp Val Ile Asp Arg Leu Gly Arg Lys
385                 390                 395                 400 aag acc atg gct ctg tgt ttc gtc atc ttt tcc ctc tgc agc ctc ctg      1248
Lys Thr Met Ala Leu Cys Phe Val Ile Phe Ser Leu Cys Ser Leu Leu
            405                 410                 415 ctg ttc atc tgc att gga aga aat gtg cta acc ctc tta ctg ttc att      1296
Leu Phe Ile Cys Ile Gly Arg Asn Val Leu Thr Leu Leu Leu Phe Ile
            420                 425                 430 gca aga gcg ttt att tct gga ggc ttc caa gca gcc tac gtt tac acg      1344
Ala Arg Ala Phe Ile Ser Gly Gly Phe Gln Ala Ala Tyr Val Tyr Thr
            435                 440                 445 cct gag gtg tat cca acg gcg acg agg gcg ctg ggc ctg ggc acc tgc      1392
Pro Glu Val Tyr Pro Thr Ala Thr Arg Ala Leu Gly Leu Gly Thr Cys
            450                 455                 460 agc ggc atg gcg aga gtg ggc gcg ctc atc act cca ttc ata gct cag      1440
Ser Gly Met Ala Arg Val Gly Ala Leu Ile Thr Pro Phe Ile Ala Gln 465                 470                 475                 480 gtg atg ctg gaa tct tcc gtg tac ctg acc ctg gcc gtc tac agt ggc      1488
Val Met Leu Glu Ser Ser Val Tyr Leu Thr Leu Ala Val Tyr Ser Gly
            485                 490                 495 tgc tgc ctc ctt gct gcc ttg gcc tcc tgc ttt ctg ccc atc gag acc      1536
Cys Cys Leu Leu Ala Ala Leu Ala Ser Cys Phe Leu Pro Ile Glu Thr
            500                 505                 510 aaa ggc cga gca ctg cag gag tcc agc cac cgg gag tgg ggc cag gag      1584
Lys Gly Arg Ala Leu Gln Glu Ser Ser His Arg Glu Trp Gly Gln Glu
            515                 520                 525 atg gtt ggc cga ggg aca aac agc aca ggc gtc ccc agg tcg aac tct      1632
Met Val Gly Arg Gly Thr Asn Ser Thr Gly Val Pro Arg Ser Asn Ser
530                 535                 540 ggc tct cag gag tag                                                  1647
Gly Ser Gln Glu
545
```

<210> SEQ ID NO 16
<211> LENGTH: 548
<212> TYPE: PRT
<213> ORGANISM: Rattus norvegicus

<400> SEQUENCE: 16

```
Met Glu Glu Asp Leu Phe Gln Leu Arg Gln Leu Pro Val Val Lys Phe
1               5                   10                  15

Arg Arg Thr Gly Glu Ser Ala Arg Ser Glu Asp Ala Ala Ser Gly
            20                  25                  30

Glu His Asp Val Gln Ile Glu Gly Val Arg Val Gly Leu Glu Ala Val
        35                  40                  45

Glu Leu Asp Asp Gly Ala Ala Val Pro Lys Glu Phe Ala Asn Pro Thr
    50                  55                  60

Asp Asp Thr Phe Met Val Glu Asp Ala Val Glu Ala Ile Gly Phe Gly
65                  70                  75                  80

Arg Phe Gln Trp Lys Leu Ser Val Leu Thr Gly Leu Ala Trp Met Ala
                85                  90                  95

Asp Ala Met Glu Met Met Ile Leu Ser Ile Leu Ala Pro Gln Leu His
            100                 105                 110

Cys Glu Trp Arg Leu Pro Ser Trp Gln Val Ala Leu Leu Thr Ser Val
            115                 120                 125
```

-continued

```
Val Phe Ile Gly Met Met Ser Ser Thr Leu Trp Gly Asn Ile Ser
            130                 135                 140

Asp Gln Tyr Gly Arg Lys Thr Gly Leu Lys Ile Ser Val Phe Trp Thr
145                 150                 155                 160

Leu Tyr Tyr Gly Ile Leu Ser Ala Phe Ala Pro Val Tyr Ser Trp Ile
                165                 170                 175

Leu Val Leu Arg Gly Leu Val Gly Phe Gly Ile Gly Val Pro Gln
            180                 185                 190

Ser Val Thr Leu Tyr Ala Glu Phe Leu Pro Met Lys Ala Arg Ala Lys
                195                 200                 205

Cys Ile Leu Leu Ile Glu Val Phe Trp Ala Ile Gly Thr Val Phe Glu
210                 215                 220

Val Leu Leu Ala Val Phe Val Met Pro Ser Leu Gly Trp Arg Trp Leu
225                 230                 235                 240

Leu Leu Leu Ser Ala Ala Pro Leu Leu Val Phe Ala Val Leu Cys Phe
                245                 250                 255

Trp Leu Pro Glu Ser Ala Arg Tyr Asp Val Leu Ser Gly Asn Gln Glu
            260                 265                 270

Lys Ala Ile Ala Thr Leu Lys Arg Ile Ala Thr Glu Asn Gly Ala Pro
            275                 280                 285

Met Pro Leu Gly Lys Leu Ile Ile Ser Arg Gln Glu Asp Arg Gly Lys
            290                 295                 300

Met Arg Asp Leu Phe Thr Pro His Phe Arg Trp Thr Thr Leu Leu Leu
305                 310                 315                 320

Trp Phe Ile Trp Phe Ser Asn Ala Phe Ser Tyr Tyr Gly Leu Val Leu
                325                 330                 335

Leu Thr Thr Glu Leu Phe Gln Ala Gly Asp Val Cys Ser Ile Ser Ser
            340                 345                 350

Arg Lys Lys Ala Val Glu Ala Lys Cys Ser Leu Ala Cys Glu Tyr Leu
            355                 360                 365

Ser Lys Glu Asp Tyr Met Asp Leu Leu Trp Thr Thr Leu Ser Glu Phe
            370                 375                 380

Pro Gly Val Leu Val Thr Leu Trp Val Ile Asp Arg Leu Gly Arg Lys
385                 390                 395                 400

Lys Thr Met Ala Leu Cys Phe Val Ile Phe Ser Leu Cys Ser Leu Leu
                405                 410                 415

Leu Phe Ile Cys Ile Gly Arg Asn Val Leu Thr Leu Leu Phe Ile
            420                 425                 430

Ala Arg Ala Phe Ile Ser Gly Gly Phe Gln Ala Ala Tyr Val Tyr Thr
            435                 440                 445

Pro Glu Val Tyr Pro Thr Ala Thr Arg Ala Leu Gly Leu Gly Thr Cys
            450                 455                 460

Ser Gly Met Ala Arg Val Gly Ala Leu Ile Thr Pro Phe Ile Ala Gln
465                 470                 475                 480

Val Met Leu Glu Ser Ser Val Tyr Leu Thr Leu Ala Val Tyr Ser Gly
                485                 490                 495

Cys Cys Leu Leu Ala Ala Leu Ala Ser Cys Phe Leu Pro Ile Glu Thr
            500                 505                 510

Lys Gly Arg Ala Leu Gln Glu Ser Ser His Arg Glu Trp Gly Gln Glu
            515                 520                 525
```

```
Met Val Gly Arg Gly Thr Asn Ser Thr Gly Val Pro Arg Ser Asn Ser
    530                 535                 540
Gly Ser Gln Glu
545
```

METHODS FOR THE IDENTIFICATION OF AGENTS FOR THE TREATMENT OF SEIZURES, NEUROLOGICAL DISEASES, ENDOCRINOPATHIES AND HORMONAL DISEASES

FIELD OF THE INVENTION

The present invention is generally drawn to the field of drug discovery in neurological disorders, endocrinopathies and hormonal diseases.

BACKGROUND OF THE INVENTION

Neurological disorders afflict a substantial number of individuals and present an increasing economic challenge to health care systems since little is known regarding their causes, their diagnosis is often subjective, and many lack effective treatment. In general, brain activity is ultimately determined by the capacity of neurons to communicate at synapses. Specific neurotransmitter chemicals are packaged in presynaptic neurons into synaptic vesicles which fuse with the presynaptic membrane to release quanta of the neurotransmitter chemical that traverse the synaptic cleft to activate the corresponding receptor type resident in the post-synaptic membrane. Among these receptor types are the neuronal glutamate receptors (GluR's), δ-aminobutyric acid receptors (GABAR's), nicotinic acetylcholine receptors, serotonin receptors, dopamine receptors, and the like. Many neurological disorders are a result of improper conduction of electrical currents through synapses in various brain tissues. In epilepsy errant currents, hypothesized to be associated with improper function of synapses, cause various levels of seizures. Likewise, in several psychiatric diseases, movement disorders and neurodegenerative diseases the conduction currents become abberant, disorganized or reduced, thereby causing the disease condition. Accordingly, defects in synaptic vesicle functions will have an adverse effect upon neurotransmission in general and control of neurotransmitter release in particular.

Seizures, including epileptic seizures, result from a focal or generalized disturbance of cortical function, which may be due to various cerebral or systemic disorders, including, for example, cerebral edema, cerebral hypoxia, cerebral trauma, central nervous system (CNS) infections, congenital or developmental brain defects, expanding brain lesions, hyperpyrexia, metabolic disturbances and the use of convulsive or toxic drugs. It is only when seizures recur at sporadic intervals and over the course of years (or indefinitely) that epilepsy is diagnosed.

Epilepsy is classified etiologically as symptomatic or idiopathic with seizure manifestations that fall into three general categories: 1) generalized tonic-clonic, 2) absence or petiti mal, and 3) complex partial. Symptomatic classification indicates that a probable cause exists and a specific course of therapy to eliminate that cause may be tried, whereas idiopathic indicates that no obvious cause can be found and may be linked to unexplained genetic factors. Of the seizure categories, most persons have only one type of seizure, while about 30% have two or more types.

The risk of developing epilepsy is 1% from birth to age 20 yr. and 3% at age 75 yr. Idiopathic epilepsy generally begins between ages 2 and 14. Seizures before age 2 are usually caused by developmental defects, birth injuries, or a metabolic disease. Those beginning after age 25 may be secondary to cerebral trauma, tumors, or cerebrovascular disease, but 50% are of unknown etiology.

Due to the many interrelationships that exist between the nervous and endocrine systems, defects in synaptic vesicle function can also impact on endocrinological function. For instance, at least two glands secrete their hormones only in response to appropriate neurotransmitter release—the adrenal medulla and the posterior pituitary gland. Upon secretion, hormones are transported in the blood to cause physiologic actions at distant target tissues in the body. Obviously, endocrinopathies involving either hyper- or hyposecretion of hormones have pathological consequences. Examplary of these consequences are giantism and dwarfism, due to hyper- or hyposecretion of growth hormone, respectfully.

Levetiracetam

Levetiracetam (LEV; ucb L059; (S)-α-ethyl-oxo-pyrrolidine acetamide), the (S)-enantiomer of the ethyl analog of piracetam, was synthesized during a follow-up chemical program aimed at identifying a second-generation nootropic drug. In vivo results have demonstrated an unexpected potent ability of LEV to suppress seizures in the audiogenic-susceptible mouse, whereas piracetam was only weakly active. Although LEV is a molecule unrelated to established antiepileptic drugs (Margineanu et al., in Antiepileptic Drugs: 5th Edition, pp. 419–427. Lippincott, Philadelphia (2002)), extensive clinical trials have proven that adjunctive therapy with LEV (KEPPRA, UCB, S. A., Braine-l'Allend, Belgium) is both effective and well tolerated in controlling refractory partial seizures in adults.

Binding assays with LEV, performed on crude rat brain membranes, reveal the existence of a reversible, saturable and stereoselective specific binding site. Results obtained in rat hippocampal membranes suggest that LEV labels a single class of binding sites with modest affinity and with a high binding capacity. This binding site is identified as the Levetiracetam Binding Site (LBS). Similar results have been obtained in other brain regions (cortex, cerebellum and striatum), ucb L060, the (R)-enantiomer of levetiracetam, displays about 1000 times less affinity for these sites. The binding of LEV appears to be confined to membranes in the central nervous system since radiolabel studies could detect no specific binding in a range of peripheral tissues including heart, kidneys, spleen, pancreas, adrenals, lungs and liver. However, this could be due to a low density of LBS in these tissues compared to the central nervous system and indeed specific binding does occur in PC12 cells, a peripherally derived adrenal cell line. The most commonly used antiepileptic drugs carbamazepine, phenytoin, valproate, phenobarbital and clonazepam, as well as the convulsant agent t-butylbicyclophosphorothionate (TBPS), picrotoxin and bicuculline do not displace LEV binding. However, ethosuximide, pentobarbital, pentylenetetrazole and bemegride competed with LEV with pKi values comparable to active drug concentrations observed in vivo. Structurally related compounds, including piracetam and aniracetam, also displaced LEV binding. The levetiracetam analogues were also tested for their anticonvulsant activity in the audiogenic mouse model of epilepsy. A very good correlation ($r^2=0.84$) was observed between the affinity and the anticonvulsant activity (Noyer et al., Euro. J. Pharmacol. 286:137–146. (1995)). This high degree of correlation is strong support for a causative relationship between LBS binding and anticonvulsant activity of this class of compounds. Accordingly, binding of levetiracetam analogues to LBS is expected to result in modification of the function of the protein component(s) of the LBS in brain, leading to the desired therapeutic outcome of anticonvulsant activity.

The Synaptic Vesicle Protein 2 Family

The Synaptic Vesicle Protein 2 (SV2) family of synaptic vesicle proteins was first identified with a monoclonal antibody prepared against cholinergic vesicles from the electric organ of the marine ray *D. ommata* (Buckley et al., J. Cell Biol. 100:1284–1294. (1985)). Cloning of the individual family members labeled by the antibody resulted in the identification of three different isoforms, SV2A (Bajjalieh et al., Science. 257:1271–1273. (1992)), SV2B (Feany et al., Cell. 70(5):861–867. 1992) and SV2C (Janz and Sudhof, Neuroscience 94(4): 1279–1290. (1999)), all of which react with the original antibody. The overall homology between the three rat isoforms is approximately 60%, with SV2A and SV2C being more similar to each other than SV2B (Janz and Sudhof, Neuroscience 94(4): 1279–1290. (1999)).

The SV2 proteins are integral membrane proteins and have significant but low-level homology (20–30%) to the twelve transmembrane family of bacterial and fungal transporter proteins that transport sugar, citrate, and xenobiotics (Bajjalieh et al., Science. 257:1271–1273. (1992)). As putative members of the 12 TM superfamily, SV2 proteins display several unique features. They have relatively short free N- and C- termini and short loops connecting the Tm segments. Two notable exceptions, however, are the long cytoplasmic loop between transmembrane regions 6 and 7 and the intravesicular loop between transmembrane regions 7 and 8 (which contains 3 N-glycosylation sites). No close homologs of the SV2 proteins have yet been discovered in yeast or invertebrates, although a distantly related synaptic vesicle protein known as SVOP does have homologs in *Drosophila* and *C. elegans* (Janz et al., J. Neurosci. 18(22): 9269–9281. (1998)).

As a family, SV2 proteins are widely distributed in the brain and in endocrine cells. The three isoforms overlap significantly in their distribution, and can be found coexpressed in the same neuron, and even on the same synaptic vesicle. One isoform or another of the SV2 proteins seems to be present on all synaptic vesicles, and they are probably not limited to neurons that contain any specific neurotransmitters, although one study reports that cholinergic vesicles may not contain SV2 (Blumberg et al., J. Neurochem. 58(3):801–810 (1992)). SV2 proteins are therefore one of the most common proteins of synaptic vesicles, and have been implicated in the control of calcium-mediated exocytosis of synaptic vesicles. SV2 proteins have also been shown to be expressed in endocrine cells and, along with the additional synaptic vesicle membrane integral proteins p38 and p65, has been demonstrated to be present in endocrine dense core granule membranes (Lowe et al., J. Cell. Biol. 106(1):51–59(1988). SV2A, the most common SV2 isoform, is expressed ubiquitously throughout the brain and is present as well in secretory granules of endocrine cells. SV2B, while broadly distributed in the brain, is undetected in several brain structures, including the dentate gyrus of the hippocampus, the globus pallidus, reticular nuclei of the thalamus, and the reticular part of the substantia nigra (Bajjalich et al., 1994). By contrast, SV2C has quite a limited distribution and is found primarily the phylogenetically old regions such as the pallidum, the substantia nigra, the midbrain, the brainstem and the olfactory bulb. It is undetectable in the cerebral cortex and the hippocampus, and found at low levels in the cerebellar cortex (Janz and Sudhof, Neuroscience 94(4): 1279–1290. (1999)).

In addition to the SV2 protein, the synapse contains other unique regulatory proteins such as synapsin, synaptotagmin and CAPS, which may mediate vesicle fusion or budding. SV2A may be a $Ca^{2+}$ regulatory protein essential for the formation of pre-fusion complexes called SNARE complexes (Xu et al. Cell 99(7):713–722 (1999)), which include the synaptic vesicle-associated VAMP/synaptobrevin and the plasma membrane proteins syntaxin and SNAP-25. Upon $Ca^{2+}$ accumulation in the synapse the binding of synaptotagmin to SV2A is inhibited and the dimerization of two synaptotagmin $Ca^{2+}$ binding domains is stimulated (Bajjalieh, Curr. Opin. Neurobiol. 9(3):321–328. (1999)). This dimerization may play a role in organizing the SNARE complex and promoting vesicle fusion, as at low $Ca^{2+}$ concentrations, SV2A remains bound to synaptotagmin and fusion will not occur.

The affinity of SV2A for synaptotagmin is regulated by the phosphorylation of the amino terminus of SV2 (Pyle et al., J. Biol. Chem. 275(22):17195–17200. (2000)). The possibility that SV2 proteins play a role in either $Ca^{2+}$ transport, or regulation in the synaptic vesicle has been supported by studies of SV2A and SV2B knockout animals (Janz et al., Neuron 24:1003–1016. (1999)). An alternative hypothesis is that the SV2 proteins, while derived from transport proteins, now serve a different function in the vesicle, whether a structural role or a role in regulation of vesicle fusion or recycling and the exocytotic release of their contents (Janz and Sudhof, Neuroscience 94(4): 1279–1290. (1999)).

There have been two reports of SV2 protein knockout mice: one that examines only SV2A knockouts (Crowder et al., Proc. Nat. Acad. Sci. USA 96(26):15268–15273. (1999)) and the other which looks at both SV2A and SV2B knockout animals, as well as the SV2A/SV2B double knockout (Janz et al., Neuron 24:1003–1016. (1999)).

Animals homozygous for SV2A gene disruption appear normal at birth, but fail to grow, experience severe seizures, and die within the first few weeks postnatal. SV2A homozygous knockout mice experience seizures that are longer lasting, stronger, and more debilitating than any other mouse strain (Janz et al., Neuron 24:1003–1016. (1999)). Despite the appearance of postnatal seizures, all SV2A knockout animals have completely normal gross brain morphology, including normal levels of the tested synaptic proteins. Furthermore, the hippocampal neuronal cultures from both SV2A and SV2A/SV2B double knockout mice formed synapses that were ultrastructurally normal, and had unchanged size, number and location of synaptic vesicles (Janz et al., Neuron 24:1003–1016. (1999); Crowder et al., Proc. Nat. Acad. Sci. USA 96(26):15268–15273. (1999)). It is interesting to note that, unlike the frequently observed seizures caused by structural and developmental abnormalities easily detected in many other type of knockouts, the SV2A knockout mice show a strong seizure phenotype with no associated macro or micro scale abnormalities of the brain or synapse. This observation suggests a direct and specific role for SV2A and the observed phenotype. As another marker of brain function, studies of synaptic transmission in primary neuronal cultures from SV2A, SV2B, and SV2A/SV2B knockout mice indicate that the sizes and frequencies of sIPSCs and of spontaneous excitatory postsynaptic currents (sEPSCs), are normal. Electrical stimulation induced robust EPSCs and IPSCs in the cultured neurons from all genotypes.

In contrast to SV2A, SV2B knockout mice reveal no overt pathology (Janz et al., 1999). It is suggested that one possible reason for this lack of consequence of loss of SV2B is that can be functionally replaced by SV2A, which appears to be co-expressed everywhere SV2B is normally expressed.

While the function of SV2A and other family members still remains unknown, the favored hypothesis is that this transporter homologue is a functional transporter for some common synaptic vesicle molecule. More specifically, there is evidence linking SV2A to the regulation of calcium-mediated vesicle exocytosis, and as a result, it is thought that it may be a $Ca^{2+}$ transporter. SV2A and other family members may also have roles in the function of synaptic vesicles. Such roles may include modulating aspects of their formation, loading with neurotransmitter, fusion with the plasma membrane, re-cycling, and interactions with other proteins and cellular compartments and organelles. For instance it has been shown that SV2 proteins can interact with the synaptic vesicle protein synaptotagmin and the extracellular matrix protein laminin-1 (Carlson, Perspect. Dev. Neurobiol. 3(4):373–386 (1996)). The SV2 proteins may play important roles in regulating cytoplasmic or organellar calcium levels at the presynaptic terminal, and may also interact with N-type calcium channels on the plasma membrane, either directly or indirectly.

SUMMARY OF THE INVENTION

The present inventors have discovered that SV2A is the binding site for the anti-seizure drug LEV and its analogs. The high degree of correlation between relative binding affinities of a series of levetiracetam analogues and their anti-convulsant potencies in certain animal models of epilepsy provides strong evidence that binding of these analogues to SV2 proteins modifies their function to provide anticonvulsant effects.

In a preferred embodiment, the invention includes a method of identifying a binding partner for a SV2 protein. The method comprises incubating a SV2 protein or fragment with levetiracetam or an analog or derivative thereof and a potential binding partner the method further comprises determining if the potential binding partner modulates the binding of levetiracetam or an analog or derivative thereof to the SV2 protein or fragment, thereby identifying a binding partner for the SV2 protein.

In another preferred embodiment, the invention includes a method of identifying a binding partner for a SV2 protein. The method comprises exposing a SV2 protein or fragment to a potential binding partner and incubating the protein or fragment and potential binding partner with (2S)-2-[4-(3-azidophenyl)-2-oxopyrrolidin-1-yl]butanamide. The method further comprises determining if the binding of (2S)-2-[4-(3-azidophenyl)-2-oxopyrrolidin-1-yl]butanamide to the protein is inhibited by the potential binding partner, thereby identifying binding partner for the protein.

In still another preferred embodiment, the invention includes a method of identifying an agent useful for the treatment of a neurological or endocrinological disorder. The method comprises exposing a SV2 protein or fragment to the agent and levetiracetam or an analog or derivative thereof. The method further comprises determining if the binding of levetiracetam or an analog or derivative thereof to the protein is modulated by the agent, thereby identifying an agent useful for the treatment of a neurological or endocrinological disorder.

In yet another preferred embodiment, the invention includes a method of identifying an agent useful for the treatment of a neurological or endocrinological disorder. The method comprises exposing a SV2 protein or fragment to the agent and incubating the protein or fragment and agent with (2S)-2-[4-(3-azidophenyl)-2-oxopyrrolidin-1-yl]butanamide. The method further comprises determining if the binding of (2S)-2-[4-(3-azidophenyl)-2-oxopyrrolidin-1-yl] butanamide to the protein is inhibited by the agent, thereby identifying binding partners for the protein.

DETAILED DESCRIPTION

Figure 1:
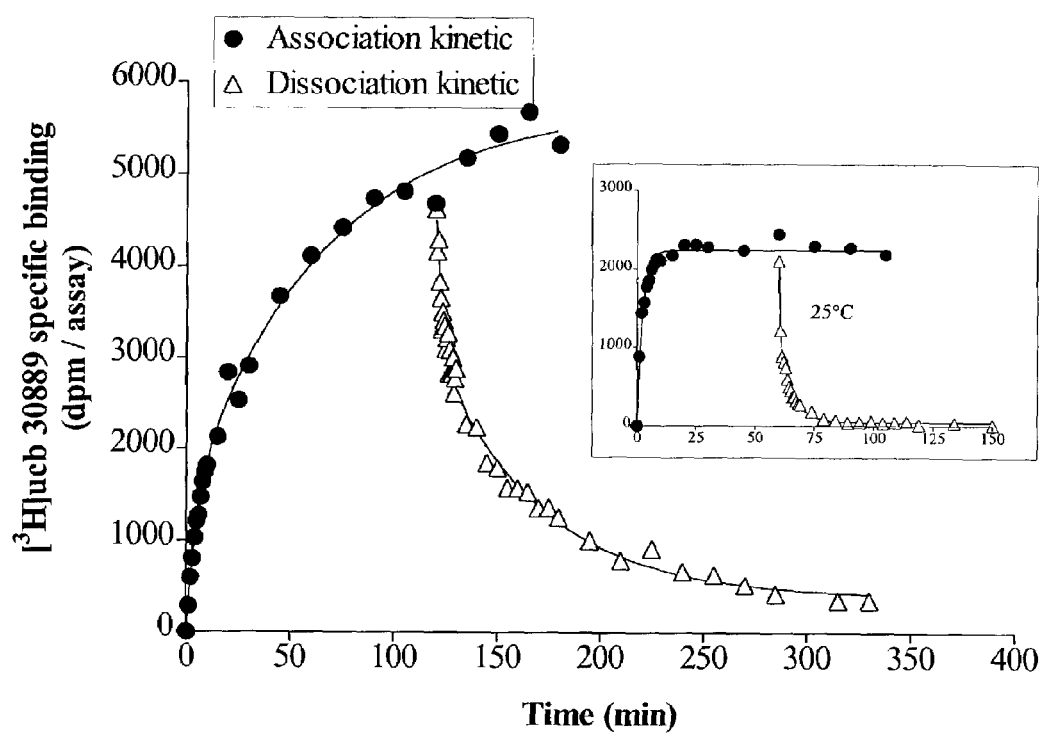
FIG. 1 depicts the reversible binding of the LEV analog ucb 30889 to LBS in rat brain cortex.

I. Synaptic Vesicle Protein 2 (SV2) Family of Proteins

Any SV2 protein that binds LEV or a derivative or analog thereof may be used in the assays herein described.

As used herein, SV2 proteins include isolated proteins, allelic variants of the proteins, and conservative amino acid substitutions of the proteins. As used herein, the "protein" or "polypeptide" refers, in part, to SV2A, a protein encoded by the nucleic acid sequence of SEQ ID NO: 1 or that has the human amino acid sequence depicted in SEQ ID NO: 2 or fragments thereof; to SV2B, which includes the human protein encoded by the nucleic acid sequence of SEQ ID NO: 3 or the amino acid sequence depicted in SEQ ID NO: 4 or fragments thereof; to SV2C, which includes the human protein encoded by the nucleic acid sequence of SEQ ID NO: 5 or the amino acid sequence depicted in SEQ ID NO: 6 or fragments thereof; and to SVOP, which includes the human protein encoded by the nucleic acid sequence of SEQ ID NO: 7 or the amino acid sequence depicted in SEQ ID NO: 8 or fragments thereof. The terms also refer to naturally occurring allelic variants and proteins that have a slightly different amino acid sequence than that specifically recited above. Allelic variants, though possessing a slightly different amino acid sequence than those recited above, will still have the same or similar biological functions associated with these proteins.

As used herein, the family of SV2 proteins related to the human amino acid sequence of SEQ ID NO: 2, 4, 6 or 8 refers in part, to proteins that have been isolated from organisms in addition to humans. For example, rat homologues of SV2A nucleic acid (SEQ ID NO: 9) and protein (SEQ ID NO: 10), SV2B nucleic acid (SEQ ID NO: 11) and protein (SEQ ID NO: 12), SV2C nucleic acid (SEQ ID NO: 13) and protein (SEQ ID NO: 14) and SVOP nucleic acid (SEQ ID NO: 15) and protein (SEQ ID NO: 16) have been identified and are included herein. The methods used to identify and isolate other members of the family of proteins related to these proteins are described below.

The SV2 proteins used in the present invention are preferably in isolated form in part of a cellular or vesicle membrane fragment, expressed in a transformed host cell, or naturally expressed in a given cell or tissue type. As used herein, a protein is said to be isolated when physical, mechanical or chemical methods are employed to remove the protein from cellular constituents that are normally associated with the protein. A skilled artisan can readily employ standard purification methods to obtain an isolated protein.

The SV2 proteins that may be used in the methods of the invention further include insertion, deletion, conservative amino acid substitution or splice variants of SEQ ID NO: 2, 4, 6, 8, 10, 12, 14 or 16. As used herein, a "conservative" variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein. As used herein, a "deletion" is defined as a change in either nucleotide or amino acid sequence in which one or more nucleotides or amino acid residues, respectively, are absent; an "insertion" or "addition" is that change in a nucleotide or amino acid sequence which has resulted in the addition of one or more nucleotides or amino acid residues, respectively, as compared to the naturally occurring SV2 and a "substitution" results from the replacement of one or more nucleotides or amino acids by different nucleotides or amino acids, respectively.

SV2 proteins of the present invention further include fusion proteins, wherein a SV2 protein, or fragment thereof, is N- or C- terminally fused to another SV2 protein or fragment thereof, which may be the same as or different from the first SV2 protein or fragment thereof, and/or to a heterologous peptide fusion partner. The heterologous peptide may be a polypeptide sequence useful for the expression, purification, solubility, identification, antigenicity, or extension of the stability of the SV2 protein or fragment thereof. Heterologous fusion partners useful in the present invention include, but are not limited to, glutathione-S-transferase (GST), poly-histidine tags, green fluorescent protein (GFP), albumin, and ovalbumin or fragments thereof.

Ordinarily, the allelic variants, the conservative substitution variants, and the members of the SV2 protein family, will have an amino acid sequence having at least about 35%, 40%, 50%, 60%, 65%, 70% or 75% amino acid sequence identity with the full length sequence set forth in SEQ ID NO: 2, 4, 6, 8, 10, 12, 14 or 16 more preferably at least about 80%, even more preferably at least about 90%, and most preferably at least about 95%, 97% or 99% sequence identity. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

Fragments of the SV2 proteins may also be used in the methods of the invention. In particular, fragments comprising the LEV binding site may be used. Such fragments may have at least about 6 or 10, 15 or 20, or 25 or 30 amino acid residues, more preferably 35 or 40 amino acid residues, even more preferably 45 or 50 amino acid residues, yet more preferably 55 or 60, still more preferably 65 or 70 amino acid residues and most preferably at least 75 or more amino acid residues The methods of the present invention may also utilize nucleic acid molecules that encode members of the SV2 protein family, including, but not limited to, both the rat and human proteins known as SV2A, SV2B, SV2C and the related synaptic vesicle protein SVOP, such as those consisting of or comprising SEQ ID NO: 2, 4, 6, 8, 10, 12, 14 or 16 and the related proteins herein described, preferably in isolated form. Vectors, plasmids and transformed host cells may also be used to produce an SV2 protein. As used herein, "nucleic acid" is defined as RNA or DNA or related molecules that encodes a protein or peptide as defined above, is complementary to a nucleic acid sequence encoding such peptides, hybridizes to such a nucleic acid and remains stably bound to it under appropriate stringency conditions, or encodes a polypeptide sharing at least about 35%, 40%, 50%, 60%, 65%, 70% or 75% sequence identity, preferably at least about 80%, more preferably at least about 85%, and even more preferably at least about 90%, 95%, 97% or 99% or more identity with the full-length peptide sequence of SEQ ID NO: 2, 4, 6, 8, or 10. The "nucleic acid molecules" useful in the invention further include nucleic acid molecules that share at least about 70% or 75% sequence identity, preferably at least about 80%, more preferably at least about 85%, and even more preferably at least about 90% and most preferably 95%, 97%, 99% or more identity with the nucleotide sequence of SEQ ID NO: 1, 3, 5, 7, or 9. Nucleic acids of the present invention also include those which encode fusion proteins comprising a SV2 protein either N- or C- terminally fused to a heterologous protein sequence or to another SV2 protein sequence.

Homology or identity at the nucleotide or amino acid sequence level is determined by BLAST (Basic Local Alignment Search Tool) analysis using the algorithm employed by the programs blastp, blastn, blastx, tblastn and tblastx (Altschul, et al., Nucleic Acids Res. 25: 3389–3402 (1997); Karlin et al., Proc. Natl. Acad. Sci. USA 87:2264–2268 (1990)) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a pre-selected threshold of significance. For a discussion of basic issues in similarity searching of sequence databases, see Altschul et al. (Nature Genetics 6, 119–129 (1994)). The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al., Proc. Natl. Acad. Sci. USA 89:10915–10919 (1992)), recommended for query sequences over 85 in length (nucleotide bases or amino acids).

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Gap comparison between sequences, available in the Accelrys' Wisconsin Package version 10.2, uses DNA parameters GAP=50 (gap creation penalty) and LEN=3 (gap extension penalty) and the equivalent settings in protein comparisons are GAP=8 and LEN=2.

"Stringent conditions" include those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1, 3, 5, 7, 9, 11, 13 or 15 and which encode a functional protein. Even more preferred hybridizing molecules are those that hybridize under the above conditions to the complement strand of the open reading frame of SEQ ID NO: 1, 3, 5, 7, 9, 11, 13 or 15. As used herein, a nucleic acid molecule is said to be "isolated" when the nucleic acid molecule is substantially separated from contaminant nucleic acid molecules encoding other polypeptides.

A. SV2A and the Levetiracetam Binding Site (LBS)

The invention includes the characterization and use of the LBS located on the SV2A protein.

As described above, "SV2A" includes the human protein as described in SEQ ID NO: 2, the human protein encoded by SEQ ID NO: 1, species homologues of human SV2A, variants of SEQ ID NO: 2 as herein described, and fragments of SV2A comprising the LBS.

II. Levetiracetam and Analogs

The methods of the invention include the use of LEV and LEV analogs or derivatives thereof in assays to identify new pharmacological agents. In a preferred embodiment, the methods of the present invention identify compounds or agents that compete with LEV and LEV analogs or derivatives thereof for binding to the LBS of SV2. As used herein, the terms "compete" and "competitive binding" refer to agents or compounds which occupy the same binding site on the LBS as LEV or analogs or derivatives thereof; displace, or are displaced by, LEV or analogs or derivatives thereof in binding to the LBS; or inhibit, or are inhibited by, LEV or analogs or derivatives thereof in binding to the LBS. In another preferred embodiment, the invention includes the identification of compounds or agents that modulate the activity of SV2A. In another preferred embodiment the methods of the present invention identify compounds or agents which have less, about the same, or greater affinity for the LBS than LEV. In yet another preferred embodiment the methods of the present invention identify compounds or agents which have less, about the same, or greater affinity for the LBS than ucb 30889. In still another preferred embodiment the methods of the present invention identify compounds or agents which in an effective amount modulate the activity of SV2A for a longer period of time than an effective amount of LEV. In even another preferred embodiment the methods of the present invention identify compounds or agents which in an effective amount modulate the activity of SV2A for a shorter period of time than an effective amount of LEV.

Figure 15:
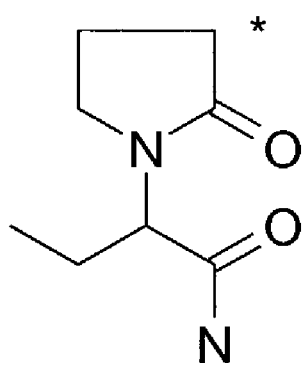
FIG. 15 (A and B) depicts the structure of (A) levetiracetam and (B) ucb30889.
Figure 15:
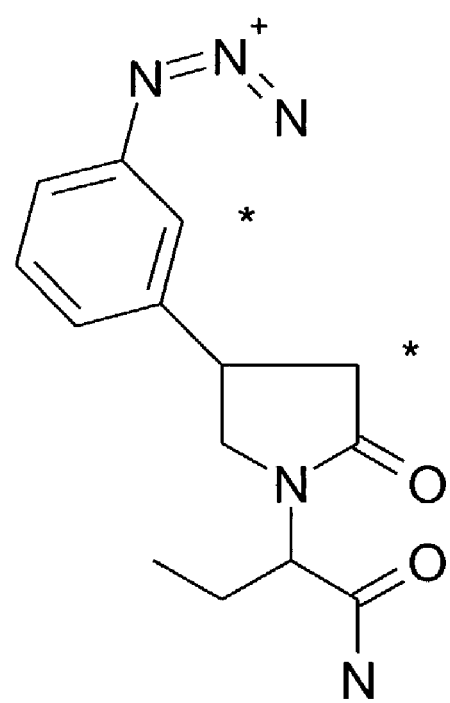

As used herein, "levetiracetam" (FIG. 15A; LEV), refers to the International Non-proprietary name of the compound (S)-α-ethyl-2-oxo-1-pyrrolidine acetamide as disclosed in European Patent No. 0 162 036 B1, herein incorporated by reference in its entirety. LEV is a laevorotary compound which is a protective agent for the treatment and prevention of hypoxic and ischemic type aggressions of the central nervous system. This compound is also effective in the treatment of epilepsy. Racemic α-ethyl-2-oxo-1-pyrrolidine acetamide and analogs thereof are known from British Patent No. 1 309 692. U.S. Pat. No. 3,459,738 discloses derivatives of 2-oxo-1-pyrrolidine acetamide.

As used herein, the term "LEV analogs or derivatives thereof" includes optionally substituted N-alkylated 2-oxo-pyrrolidine derivatives. Preferably, those compounds are alkyl amides derivatives substituted on the positions 4 and/or 5 of the pyrrolidone ring. Examples of optionally substituted N-alkylated 2-oxo-pyrrolidine derivatives include, but are not limited to, compounds such as those disclosed in international patent application PCT/EP01/01992 such as (2S)-2-[(4S)-4-(2,2-difluorovinyl)-2-oxopyrrolidinyl]butanamide, (2S)-2-[(4R)-2-oxo-4-propylpyrrolidinyl]butanamide, (2S)-2-[(4S)-2-oxo-4-propylpyrrolidinyl]butanamide, and (2S)-2- [4-(3-azidophenyl)-2-oxopyrrolidin-1-yl]butanamide.

As used herein, the term "LEV analogs or derivatives thereof" further include optionally substituted N-alkylated 2-oxo-piperidinyl derivatives. Preferably, those compounds are alkyl amides derivatives substituted on the position 4 and/or 5 and/or 6 of the 2-oxo-piperidinyl ring. Examples of optionally substituted N-alkylated 2-oxo-pyrrolidine derivatives include, but are not limited to, compounds such as those disclosed in international patent application PCT/EP02/05503 such as (2S)-2-[5-(iodomethyl)-2-oxo-1-piperidinyl]butanamide, (2S)-2-[5-(azidomethyl)-2-oxo-1-piperidinyl]butanamide, 2-(2-oxo-5-phenyl-1-piperidinyl] butanamide, (2S)-2-[4-(iodomethyl)-2-oxo-1-piperidinyl] butanamide, and (2S)-2-[4-(2-fluoro-2-methylpropyl)-2-oxo-1-pyrrolidinyl]butanamide.

As used herein, the term "LEV analogs or derivatives thereof" includes any acetam compound of formula I, in racemic or isomeric form, or a pharmaceutically acceptable salts thereof,

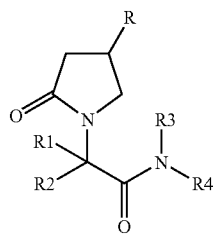

(I)

wherein
R represents hydrogen or hydroxy;
$R^1$ and $R^2$ represent independently hydrogen or an alkyl group of 1–4 carbon atoms; and
$R^3$ and $R^4$ represent independently hydrogen, an alkyl group of 1–4 carbon atoms or $-(CH_2)_n-NR^5R^6$ wherein n is 1, 2 or 3 and $R^5$ and $R^6$ represent independently hydrogen or an alkyl group of 1–4 carbon atoms.

An example of such an acetam compound includes, but is not limited to, a compound of formula I wherein R, $R^1$, $R^2$, $R^3$ and $R^4$ are hydrogen, 2-oxo-pyrrolidineacetamide, known by the generic name piracetam as described in UK Patents Nos. 1,039,113 and 1,309,692.

As used herein, the term "LEV analogs or derivatives thereof" also include optionally substituted N-alkylated 2-oxo-azepanyl derivatives. Preferably, those compounds are alkyl amides derivatives substituted on the positions 4 and/or 5 and/or 6 and/or 7 of the 2-oxo-azepanyl ring. Examples of optionally substituted N-alkylated 2-oxo-azepanyl derivatives include, but are not limited to, compounds such as those disclosed in international patent application PCT/EP02/05503 such as 2-[5-(iodomethyl)-2-oxo-1-azepanyl]butanamide.

In another embodiment the present invention includes compounds or agents which are derivatives or analogs of piracetam which bind to the LBS. Such compounds would also include molecules such as aniracetam and nefiracetam. In a preferred embodiment, the derivatives or analogs of piracetam are those which modulate the activity of SV2A or other SV2 family members.

III. Assay Formats

Assays of the present invention include methods of identifying agents or compounds which are useful for the treatment of neurological disorders, such as seizures, epilepsy, Parkinson's disease, Parkinson's dyskinesias, migraine, Alzheimer's disease, neuropathic pain, essential tremor, cognitive disorders, movement disorders, endocrinopathy and adrenal-medulla-related disease, such as hypoglycemia and circulation shock. Assays of the present invention also include methods of identifying agents or compounds which have cognitive enhancing effects, such as for example might be measured in animal models of cognition. In particular, the assays of the present invention include methods of identifying agents or compounds that compete with LEV or analogs or derivatives thereof for binding to the LBS of SV2A, displace, or are displaced by, LEV or analogs or derivatives thereof in binding to the LBS; or inhibit, or are inhibited by, LEV or analogs or derivatives thereof in binding to the LBS.

LEV, ucb 30889 (FIG. 15B) and other derivatives or analogs of LEV as described above are useful in the methods of the invention as binders in assays to screen for new compounds or agents that bind to the LBS of SV2A. In such assay embodiments, LEV, ucb 30889 and derivatives or analogs can be used without modification or can be modified in a variety of ways; for example, by labeling, such as covalently or non-covalently joining a moiety which directly or indirectly provides a detectable signal. In any of these assays, the materials can be labeled either directly or indirectly. Possibilities for direct labeling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. In addition, FRET techniques could be used to analyze interactions between ligands and the LBS of SV2A. Possibilities for indirect labeling include biotinylation of one constituent followed by binding to avidin coupled to one of the above label groups or the use of anti-ligand antibodies. The compounds may also include spacers or linkers in cases where the compounds are to be attached to a solid support.

To identify agents or compounds which compete or interact with LEV and ucb 30889 and derivatives for binding to the LBS of SV2A, intact cells, cellular or membrane fragments containing SV2A or the entire SV2A protein or a fragment comprising the LBS of the SV2A protein can be used. The agent or compound may be incubated with the cells, membranes, SV2 protein or fragment prior to, at the same time as, or after incubation with LEV or an analog or derivative thereof. Assays of the present invention can measure any property or function known for SV2 proteins, synaptic vesicles, neural transmission and/or endocrine cell function, as well as presynaptic accumulation of divalent cations, including $Ca^{2+}$. Examples of properties or functions of an SV2 protein which may be measured as an assay endpoint include, but are not limited to, phosphorylation state, binding of divalent cations, including $Ca^{2+}$; membrane transport; transport of divalent cations (including $Ca^{2+}$) into and/or out of synaptic vesicles; transport of neurotransmitters (including, but not limited to amines, acetylcholine, excitatory neurotransmitters, GABA, serotonin, and glycine) into and/or out of synaptic vesicles; interaction with other proteins (including, but not limited to laminins and synaptotagmin); conformational changes, as measured by sensitivity to proteolysis or other changes in biochemical or biophysical properties; divalent cation channel formation; formation or dissociation of protein complexes; synaptic vesicle function; fusion; exocytosis; and synaptic vesicle recycling.

Assays of the invention may be modified or prepared in any available format, including high-throughput assays that monitor the binding of LEV or the binding of derivatives or analogs thereof to SV2A or to the LBS of the SV2A protein. In many drug screening programs which test libraries of compounds, high throughput assays are desirable in order to maximize the number of compounds surveyed in a given period of time. Such screening assays may use intact cells, cellular or membrane fragments containing SV2A as well as cell-free or membrane-free systems, such as may be derived with purified or semi-purified proteins. The advantage of the assay with membrane fragment containing SV2A or purified SV2A proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules.

In one embodiment of a competitive screening assay, the assay can be formulated to detect the ability of a test agent or compound to inhibit binding of ucb 30889 to SV2A or a fragment of SV2A comprising the LBS or of LEV, or derivatives or analogs thereof, to SV2A or a fragment of SV2A comprising the LBS. In another embodiment of a competitive screening assay, the assay can be formulated to detect the ability of ucb 30889 or of LEV, or derivatives or analogs thereof, to inhibit binding of a test agent or compound to SV2A or a fragment of SV2A comprising the LBS. The inhibition of complex formation may be detected by a variety of techniques. For instance, modulation of the formation of complexes can be quantitated using, for example, detectably labeled ucb 30889, LEV, or derivatives or analogs of LEV. The inhibition of complex formation may be detected by using a detectably labeled version of the agent or compound being assayed for competitive binding to the LBS of SV2A. Alternatively, the binding between the SV2A protein and a ligand may be detected with no need of a labeled probe. For instance surface plasmon resonance, nuclear magnetic resonance or mass spectrometry are the instruments of choice for such binding assays. Another method is to measure changes in the sensitivity of SV2 proteins to proteases induced by binding of a ligand.

In certain instances, it will be desirable to immobilize one of the LBS (SV2A or a fragment of SV2A comprising the LBS) or the ligand (LEV, ucb 30889 or the test agent or compound) to facilitate separation of complexes from uncomplexed forms, as well as to accommodate automation of the assay. Binding of a ligand to the LBS, for instance binding of a candidate agent or compound to SV2A, in the presence and absence of LEV or ucb 30889, can be accomplished in any vessel suitable for containing the reactants. Examples include microtiter plates, test tubes, and microcentrifuge tubes. In one embodiment, a fusion protein can be provided which adds a domain that allows the LBS to be bound to a matrix. For example, glutathione-S-transferase (GST) fusion proteins can be adsorbed onto glutathione sepharose beads (Sigma Chemical, St. Louis, Mo.) or glutathione derivatized microtiter plates, which are then combined with the labeled LEV, ucb 30889, or derivatives or analogs of LEV and the unlabeled test agent or compound; or alternatively, with the unlabeled LEV, ucb 30889, or derivatives or analogs of LEV and the labeled test agent or compound. The mixture is then incubated under conditions conducive to complex formation. Following incubation, the beads are washed to remove any unbound reactants, and the matrix immobilized label determined directly, or in the supernatant after the LBS/ligand complexes are subsequently dissociated. When amenable, the complexes can be dissociated from the matrix, separated by SDS-PAGE, and the level of ligand found in the bead fraction quantitated from the gel using standard electrophoretic techniques.

Other techniques for immobilizing proteins on matrices are also available for use in the subject assay. For instance, the LBS can be immobilized utilizing conjugation of biotin and streptavidin. Biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the LBS but which do not interfere with ligand binding can be derivatized to the wells of the plate, and LBS binding trapped in the wells by antibody conjugation. As above, preparations of a ligand and a test compound are incubated in the protein-presenting wells of the plate, and the amount of protein/ligand complex trapped in the well can be quantitated. Exemplary methods for detecting such complexes, in addition to those described above, include immunodetection of complexes using antibodies reactive with the ligand, or which are reactive with the protein and compete for binding with the ligand.

In another embodiment of the invention, competitive binding assays can be carried out using cellular extracts of cells or tissues that comprise the LBS to identify SV2 binding partners. As used herein, a cellular extract refers to a preparation or fraction that is made from a lysed or disrupted cell. The preferred source of cellular extracts will be cells derived from human central nervous tissue or endocrine tissues. In particular, cellular extracts may be prepared from a particular region, including, but not limited to, the hippocampus, the cerebellum, the cerebrum, the cerebral cortex, the pituitary, the medulla and the adrenal gland. Further, cellular extracts may be prepared from a particular primary cell isolate of central nervous system origin or the endocrine systems including, but not limited to, neurons, astrocytes, and endocrine cells of the medulla. Alternatively, cellular extracts may be prepared from available cell lines, particularly cell lines of a neurological or endocrine origin. Cell lines contemplated herein include, but are not limited to, rat PC12 pheochromocytoma cells, AtT-20, GH3 and HIT cells.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with SV2 protein or fragment and other components of the assay under conditions in which association of the protein with the binding partner can occur, followed by the addition of LEV or an analog or derivative thereof. Alternatively, the LEV or an analog or derivative thereof may be added to the cellular extract before or at even time with the test agent or compound. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to SV2A can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the LBS can be immobilized on a solid support. For example, the LBS can be attached to a nitrocellulose matrix or acrylic beads. Attachment of the LBS to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al., Methods Mol. Biol. 69:171–184 (1997) or Sauder et al., J. Gen. Virol. 77:991–996 (1996) or identified through the use of epitope tagged proteins or GST fusion proteins.

Alternatively, the yeast two-hybrid system may be a tool for the identification of protein-protein interactions.

IV. Uses for Agents on the Invention

The invention includes the use of compounds or agents identified by the methods of the invention for the treatment of neurological and endocrinological disorders. In a preferred embodiment, agents identified by the methods of the present invention are used for the treatment of epilepsy, epileptogenesis, seizure disorders, convulsions and withdrawal seizures. In other preferred embodiments, agents identified by the methods of the present invention are used for the treatment of neurological disorders including bipolar disorders, mania, depression, anxiety, migraine, trigeminal and other neuralgia chronic pain conditions, neuropathic pain, anaesthesia-related hyperexcitability, cerebral ischemia, head trauma, myotonia, cocaine and alcohol abuse, stroke, myoclonus, essential tremor, tics, Tourette's syndrome, dyskinesia, spasticity and other movement disorders, neonatal cerebral haemorrhage, amyotrophic lateral sclerosis, Parkinson's and Alzheimer's disease, other neurodegenerative diseases including dementia. In still other preferred embodiments, agents identified by the methods of the present invention are used for the treatment of endocrinological disorders including endocrinopathies involving either hyper- or hyposecretion of one or several hormones and adrenal-medulla-related diseases, such as hypoglycemia and circulation shock. In further preferred embodiments, the invention includes the use of compounds or agents identified by the methods of the invention for the treatment of exitatory states caused by conditions including, but not limited to; drug and alcohol abuse, dependence and/or withdrawal; and emergence from general anesthesia.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Development of a Levetiracetam Analog for Binding Studies

LEV has been shown to bind to a specific binding site located preferentially in the brain (levetiracetam binding site or LBS : Noyer et al., Euro. J. Pharmacol. 286:137–146. (1995)). However, $[^{3H}]$LEV displayed only micromolar affinity for this site, making it unsuitable for in depth characterization. This example describes the binding properties of $[^{3H}]$ucb 30889, (2S)-2-[4-(3-azidophenyl)-2-oxopyrrolidin-1-yl]butanamide, an analogue of levetiracetam. Binding experiments were conducted on crude rat brain membranes at 4° C. as described in Noyer et al. (Euro. J. Pharmacol. 286:137–146. (1995)). Incubation time for equilibrium studies was 120 min. For kinetic and competition studies, $[^{3H}]$ucb 30889 (30 Ci/mmol) was used at a concentration of 1.3 nM in 0.5 ml of a Tris-HCl (pH 7.4) buffer containing 2 mM $Mg^{2+}$. Localization of the LBS in brain substructures was assessed by autoradiography on 25 μm thick slices incubated under similar conditions. Slides were then washed twice for 10 min at 4° C. in 50 mM Tris-HCl (pH 7.4) containing 0.5% BSA, dried and exposed for 3 weeks to $[^{3H}]$Hyperfilm at –20° C. Non-specific binding (NSB) was determined by the inclusion of 1 mM LEV during the incubation period.

FIG. 1 shows that $[^{3H}]$ucb 30889 binds reversibly to LBS in rat brain cortex. Binding kinetics were biphasic: half-times for association and dissociation were respectively, 3±2 min and 4±1 min for the fast component (25 to 50% of the sites), and 47±13 min and 61±15 min for the slow component. At 25° C., kinetics increased dramatically and only one component remained.

Figure 2:
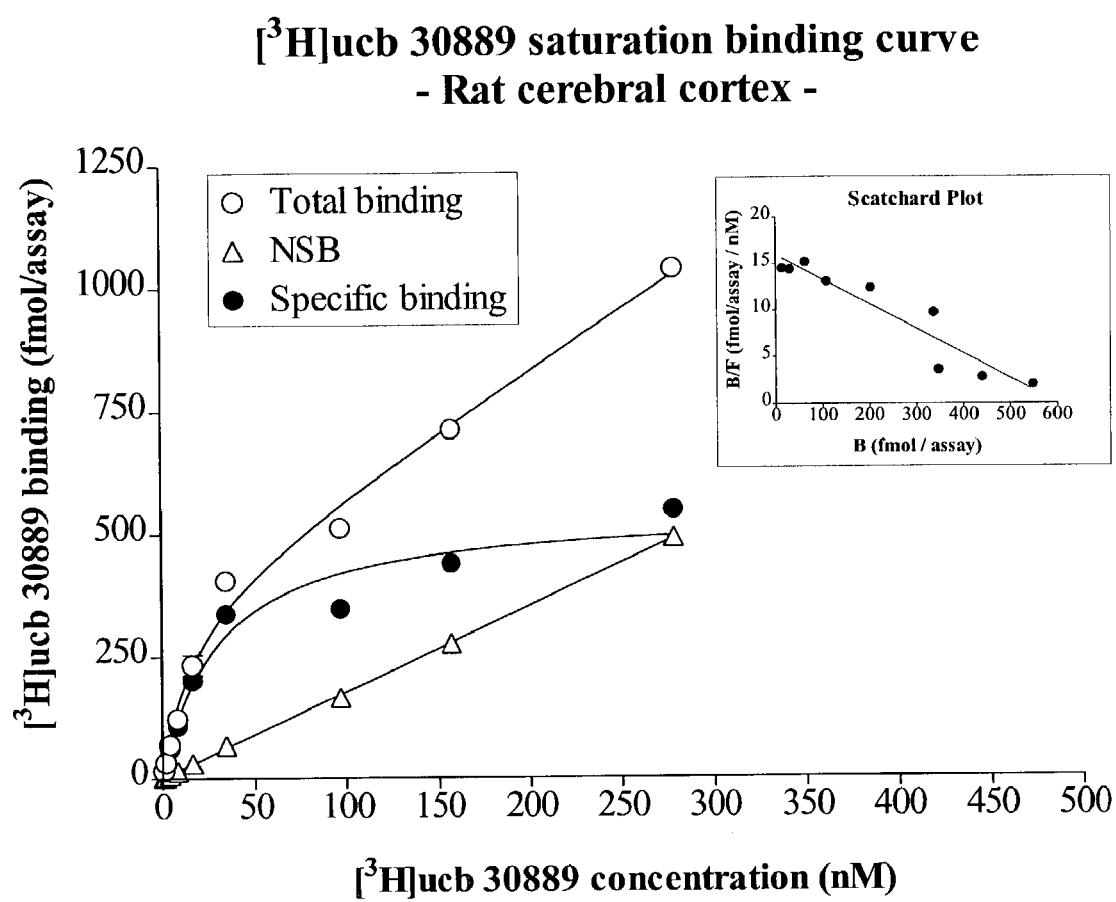
FIG. 2 depicts the saturation binding curves of ucb 30889.

FIG. 2 shows that the saturation binding curves of $[^{3H}]$ucb 30889 were compatible with the labeling of a homogeneous population of binding sites. $K_D$ and $B_{max}$ were respectively 42±10 mM and 5054±704 fmol/mg protein. The $B_{max}$ being similar to the value estimated using $[^{3H}]$levetiracetam as radioligand in similar membrane preparations (4718±413 fmol/mg protein).

Figure 3:
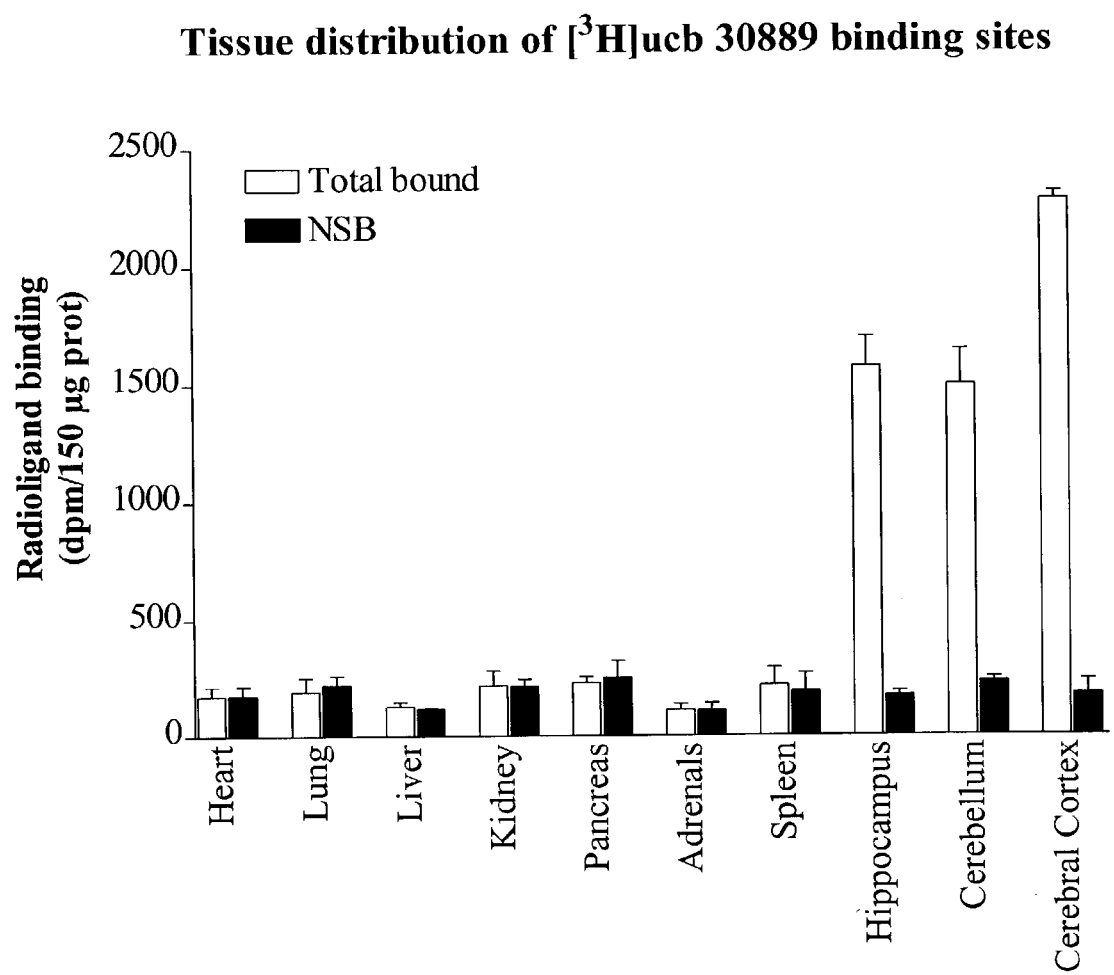
FIG. 3 shows that specific binding could not be detected in the peripheral tissues.

Specific binding could not be detected in the peripheral tissues examined (FIG. 3). The limit of detection under the experimental conditions (150 μg of protein/assay and 1.3 nM of radioligand) was a $B_{max}$ of 200 fmol/mg protein. This suggests that there are at least 25 times more binding sites in the cerebral cortex compared to the periphery.

Figure 4:
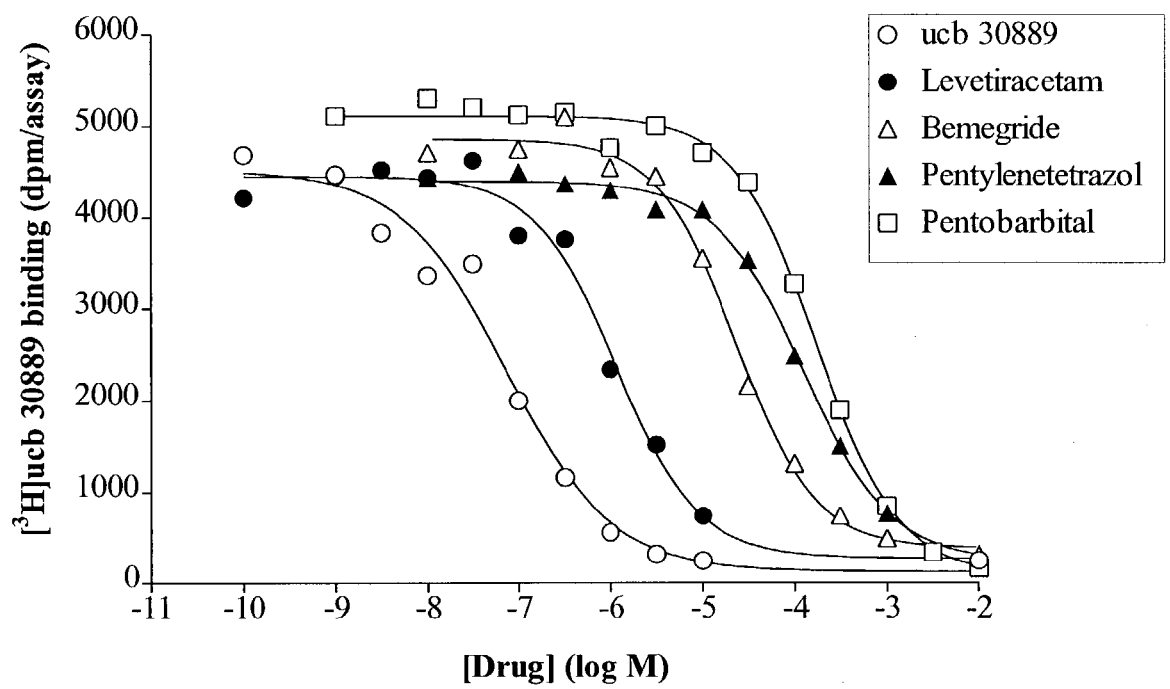
FIG. 4 depicts competition binding curves showing that ucb 30889 binds to LBS with about 10 fold higher affinity than LEV.
Figure 5:
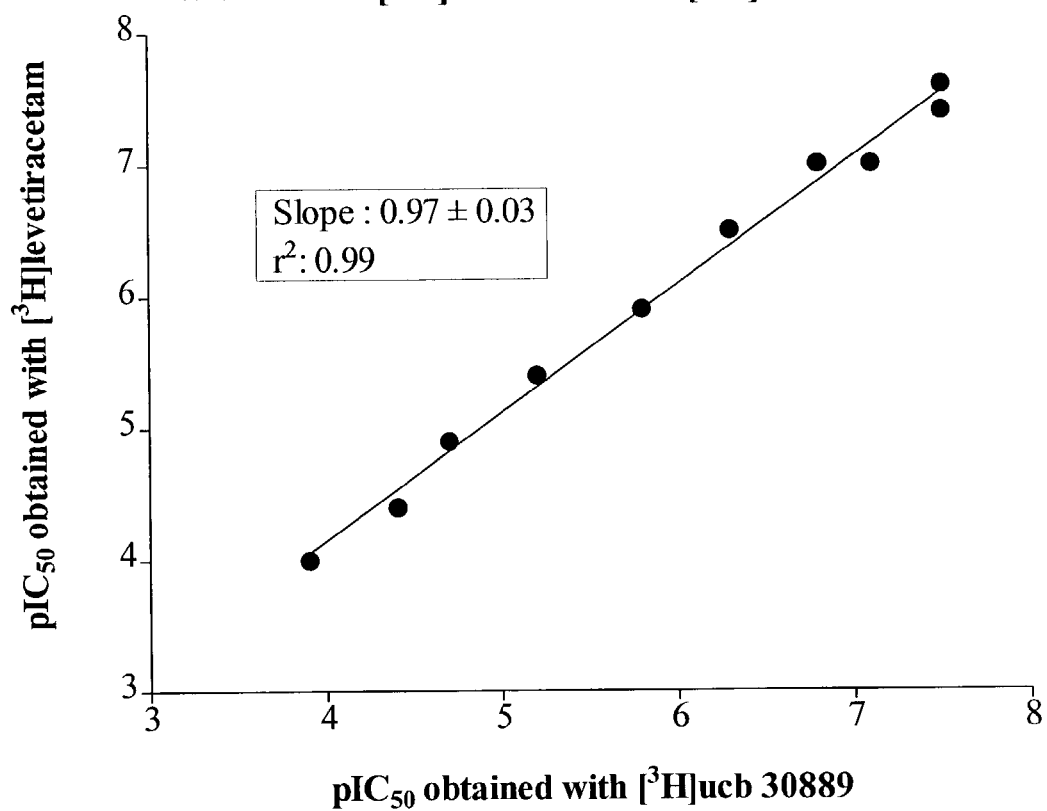
FIG. 5 depicts $pIC_{50}$ values for ucb 30889 versus levetiracetam.

Competition binding curves showed that ucb 30889 binds to LBS with about 10 fold higher affinity than LEV (FIG. 4). The pKi of ucb 30889 (7.1±0.2) agrees well with the $K_D$ of $[^{3H}]$ucb 30889 as determined by the saturation binding curve (FIG. 2). $pIC_{50}$ values for a variety of levetiracetam analogues and other compounds known to interact with the LBS, such as pentylenetetrazol or bemegride (Noyer et al., 1995), were identical whether obtained with $[^{3H}]$ucb 30889 or $[^{3H}]$levetiracetam (FIG. 5).

Figure 6:
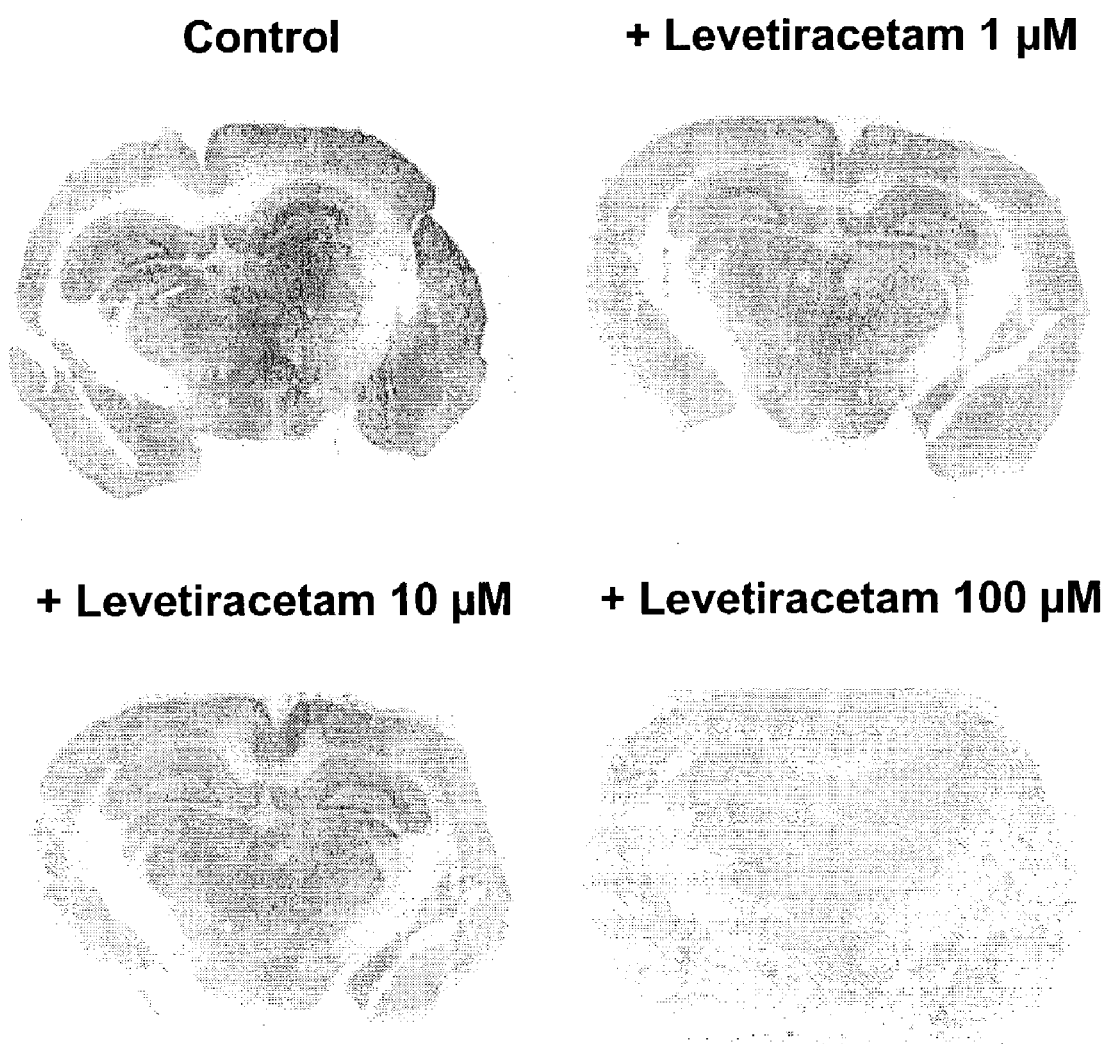
FIG. 6 depicts the concentration dependent inhibition of $[^{3H}]$ucb 30889 binding by unlabeled levetiracetam in autoradiography of rat brain.

Rat brain sections incubated with $[^{3H}]$ucb 30889 (FIG. 6) show that LBS labeled by $[^{3H}]$ucb 30889 are diffusely localized throughout the brain and that this binding can be inhibited by levetiracetam at concentrations equivalent to those observed in in vitro binding (FIG. 4).

This example demonstrates through competition binding studies and tissue distribution that ucb 30889 and LEV are both labeling the same sites, namely the LBS which is localized throughout the central nervous system. Compared to LEV, ucb 30889 binds to the LBS with 10 fold higher affinity and with a very low non specific binding. These criteria along with suitable binding kinetics at 4° C. made it possible to use this radioligand to perform autoradiography binding studies on brain slices (FIG. 6) and to show the anatomical distribution of LBS in rat brain.

Example 2

Cellular and Subcellular Distribution of the LBS

To identify and characterize the LBS in situ, $[^{3H}]$ucb 30889 was used to map the LBS within the brain and to study both its cellular and subcellular distribution. For rat brain autoradiography, 25 µm slices were incubated with 1.3 nM $[^{3H}]$ucb 30889 for 120 min at 4° C. in 50 mM Tris-HCl buffer (pH 7.4). Binding assays with rat brain membranes and various neuronal cell lines were performed under similar conditions. Non-specific binding was determined by the inclusion of 1 mM levetiracetam in the assay. For photolabeling, membranes were incubated with 40 mM $[^{3H}]$ucb 30889 for 120 min at 4° C. in the same buffer, followed by irradiation with UV-light for 30 min.

Figure 7:
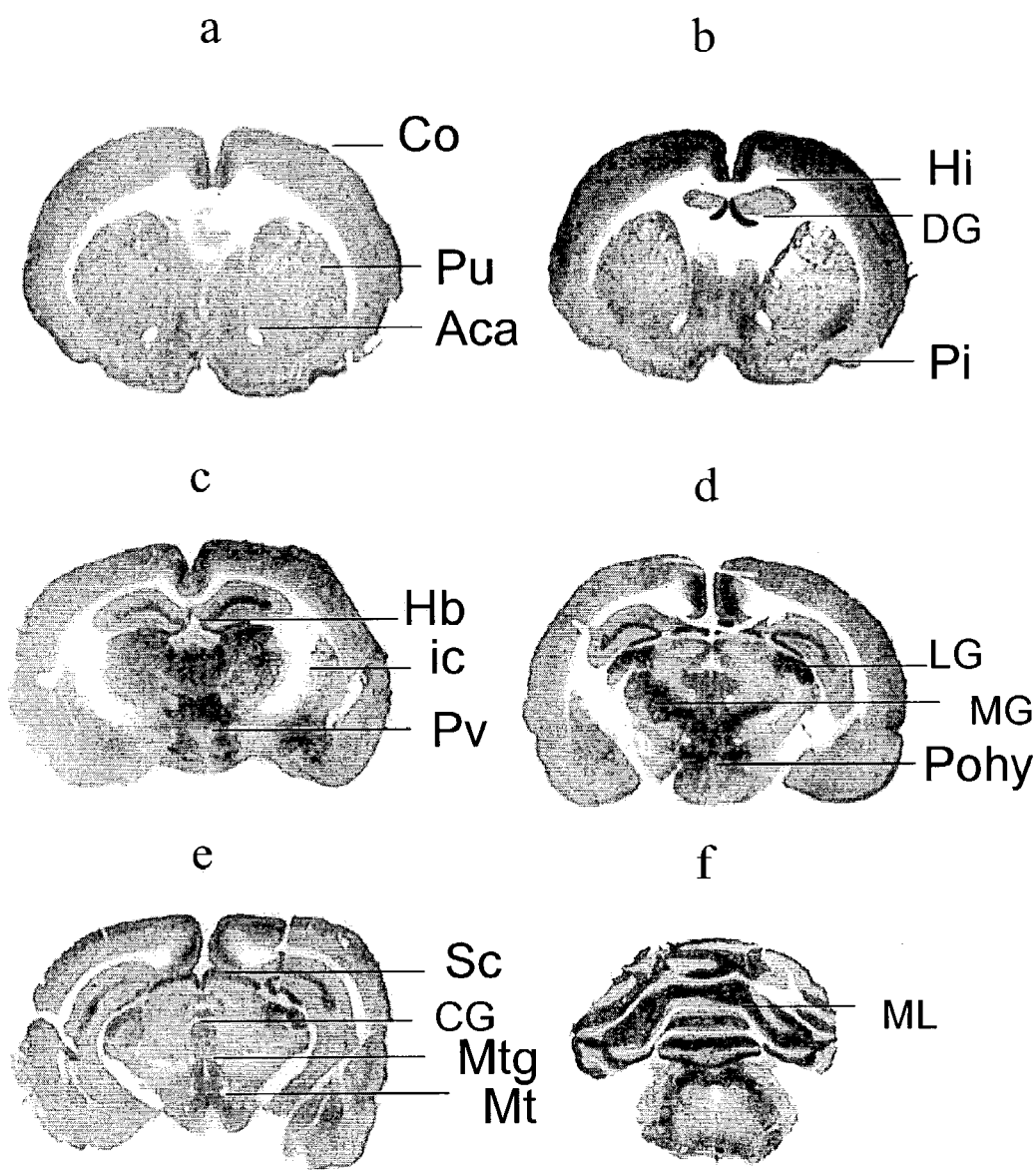
FIG. 7 depicts autoradiography of $[^{3H}]$ucb 30889 binding to coronal sections of rat brain.

For rat brain autoradiography, 25 µm slices were incubated with 1.3 nM $[^{3H}]$ucb 30889 for 120 min at 4° C. in 50 mM Tris-HCl buffer (pH 7.4). FIG. 7 shows that ucb 30889 binding sites are heterogeneously distributed in the rat brain. While there is no apparent binding in the white matter there is a high level of binding in the dentate gyrus, the superior colliculus, several thalamic nuclei and in the molecular layer of the cerebellum. Binding is less pronounced in the cerebral cortex, the hypothalamus and the striatum. Abbreviations: cc, corpus callosum; Aca, anteria commissure; ic, internal capsule; Mtg, mamillotegmental tractus; Mt, mammillothalamic tractus; ML, molecular layer; Hi, hippocampus; DG, dentate gyrus; sc, superior colliculus; CG, central grey; Pu, caudate putamen; Pv, paraventricular nucleus; MG, geniculate nuclei; Po hy, posterior hippothalamic areas; Hb, habenula; Pi, piriform cortex.

$[^{3H}]$ucb 30889 binding in cerebellar granule neurons and PC12 cells showed high levels of specific binding (Table 1). The Kd being similar to the value measured in rat cerebral cortex (42 nM; see Example 1). The same specific binding site could not be detected in primary astrocytes and in a range of CNS-related cell lines and non neuronal cell lines. Abbreviation: nd, not detected.

TABLE 1

Density and affinity of $[^{3H}]$ucb 30889 binding in various cell types

| Cell type | $B_{max}$ | Kd |
|---|---|---|
| Rat cerebellar granule neurons | 0.7 pmol/mg protein | 59 nM |
| Mouse cortical neurons | 1.4 pmol/mg protein | 34 nM |
| Mouse cortical astrocytes | nd | nd |
| PC12 | 79000 sites/cell | 50 nM |
| SK-N-SFI | nd | nd |
| NG108-15 | nd | nd |
| N1E-115 | nd | nd |
| HCN-1a | nd | nd |
| CHO-K1 | nd | nd |
| COS-7 | nd | nd |

Figure 8:
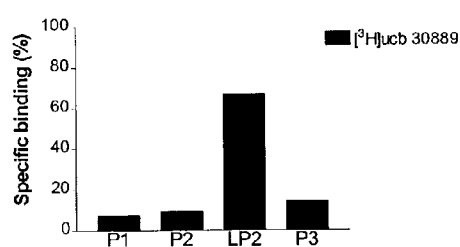
FIG. 8 depicts the subcellular distribution of $[^{3H}]$ucb 30889 binding within rat brain.
Figure 8:
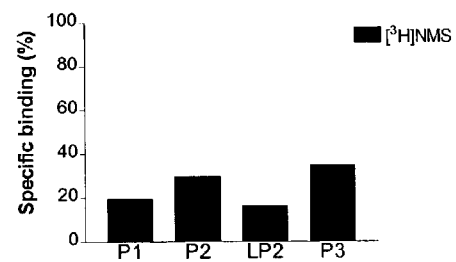
Figure 8:
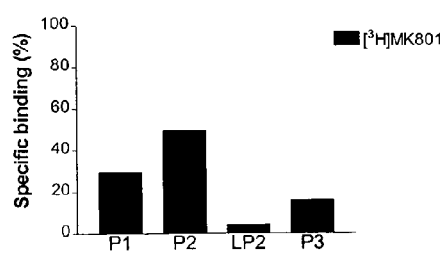
Figure 8:
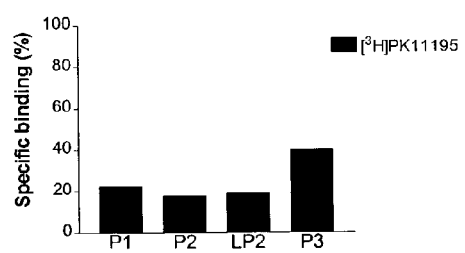

Rat brain membranes were separated by differential centrifugation (FIG. 8). Binding to LBS (8A), muscarinic (8B), NMDA (8C) and peripheral benzodiazepine (8D) receptors was determined using $[^{3H}]$ucb 30889,$[^{3H}]$NMS, $[^{3H}]$MK801 or $[^{3H}]$PK11195, respectively. This study shows that the levetiracetam binding site is present in crude synaptosomes (P2), microsomal membranes (P3) and is enriched in synaptic vesicles (LP2). In contrast, the other studied receptors are not more abundant in LP2 compared to P2 or P3. P1 is a low speed pellet containing nuclei and large debris.

Figure 9:
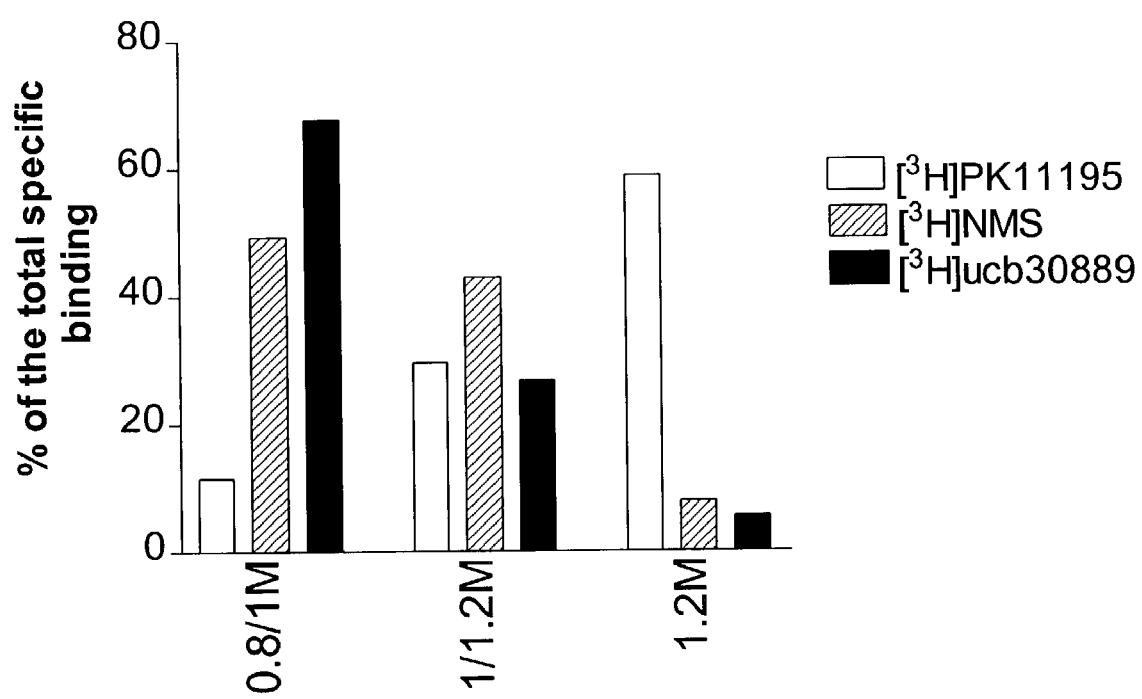
FIG. 9 depicts the subfractionation of the synaptosomal fraction by centrifugation in sucrose gradient.

A fractionation onto a sucrose gradient was used to isolate the subcellular compartments from crude synaptosomes. The LBS was found in purified synaptic membranes but was not present in the 1.2 M sucrose pellet containing the purified mitochondrial fraction (FIG. 9). As a control for the purity of the subcellular fractions, the distribution of the muscarinic and the peripheral benzodiazepine receptors was also analyzed. Data are expressed as percentage of the total specific binding.

Figure 10:
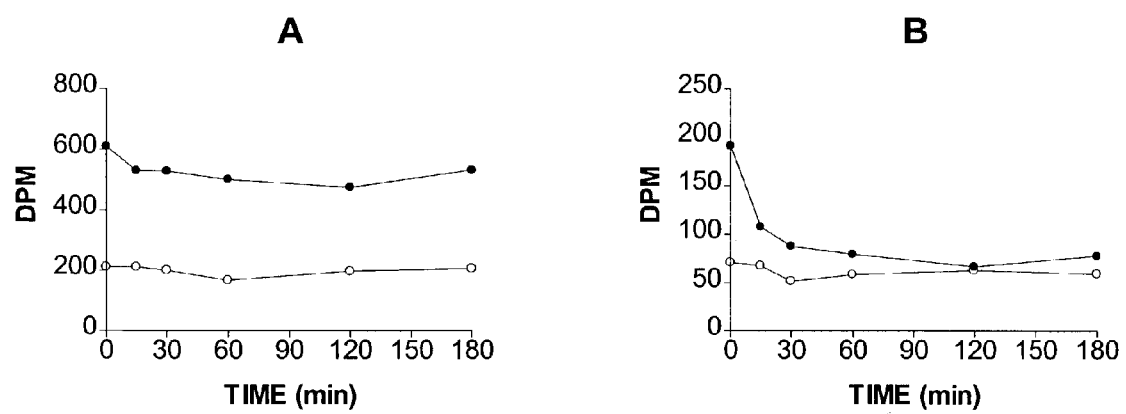
FIG. 10 depicts the photolabelling of the LBS by $[^{3H}]$ucb 30889 and irreversibility of the complex.

Crude synaptosomes (P2 fraction) were preincubated with 40 nM $[^{3H}]$ucb 30889, then irradiated with UV light and washed. At 0 min 1 mM levetiracetam was added and aliquots were counted at the indicated times (FIG. 10A). Nonspecific binding (open symbol) was determined using 1 mM levetiracetam. FIG. 10B shows the same experiment, but performed in the absence of UV light irradiation. These results indicate that during UV irradiation the radioligand inserts covalently in the binding domain of the LBS.

Figure 11:
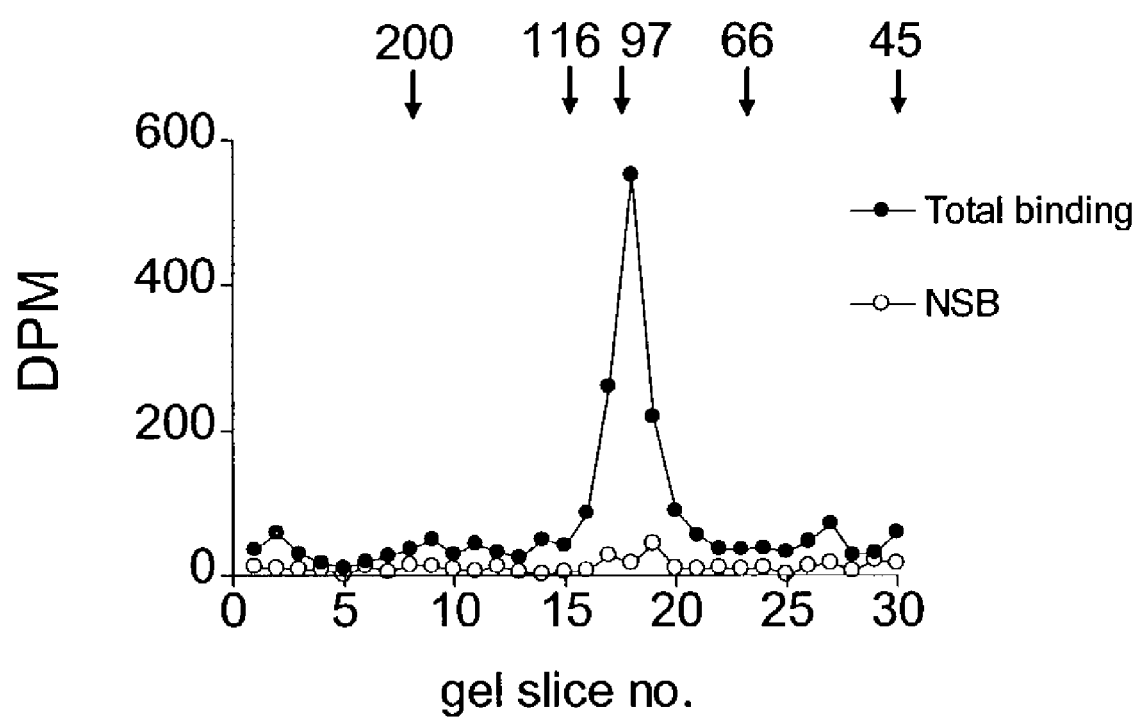
FIG. 11 depicts gel electrophoresis of membrane proteins labeled by $[^{3H}]$ucb 30889.

Photoaffinity labeling was performed in the absence or in the presence of 1 mM levetiracetam. The proteins were resolved by SDS-PAGE using an acrylamide concentration of 7.5% (w/w) and the radioactivity was assessed in each slice of the gel. The major site of incorporation occurs at a molecular weight of 97,000 (FIG. 11).

In this example it is shown that the $[^{3H}]$ucb 30889 binding site in rat brain has a unique profile of distribution and does not appear to correlate with any specific neurotransmitter system that is typically associated with epilepsy. This novel binding site is restricted to neuronal cell types and several brain areas. This novel radioligand can be used as a photoaffinity label and binds covalently to a membrane protein of high molecular weight which is mainly located in synaptic vesicles.

Example 3

The LBS is on SV2A

The biochemical characterization of LBS in rat brain led to studies to identify potential candidate LBS proteins for cloning and binding characterization. Based on the integral membrane nature of the protein, brain specific expression, apparent size, and synaptic vesicle localization, the SV2 protein family was analyzed as a candidate for localization of the LBS. Accordingly, SV2 proteins were cloned and assayed for binding of LBS ligands.

Human SV2A was cloned from a human fetal brain cDNA library as a 3609 bp PCR product comprising the coding region and significant flanking regions from the transcript. Using a vector containing the SV2A coding region plus significant flanking DNA as a source, the coding region was PCR amplified without the flanking regions. This product was cloned into a GATEWAY (Invitrogen) donor vector for ease of subcloning. Only the use of a cloning vector with strong transcription stop sites directly upstream of the cloning site resulted in successful cloning of coding-region only SV2A cDNA. This suggests that this product may be toxic to *E coli*, even in small amounts. Sequencing of the final pDONR GATEWAY SV2A clone showed that it had 2 mutations: one silent, and one a Leu-to-Pro mutation. The non-silent mutation was corrected and sequencing confirmed that the correct, full length human SV2A coding sequence was cloned.

The human SV2A coding region was transferred from the pDONR GATEWAY cloning vector to a pDEST 12.2 Gateway expression vector. This vector has a CMV promoter driving the introduced gene, and an SV40 ori, which allows very high levels of replication in the COS-7 cell line, which contains the large T antigen. In addition, the human SV2A coding region was transferred into a pDEST 40 Gateway expression vector. This vector is very similar to the 12.2 vector above, with a CMV promoter driving expression of hSV2A, and an SV40 ori, and a Neomycin resistance gene.

Initial tests of SV2A expression using the pDEST 12.2 vector was performed in the COS-7 cell line, which had previously been demonstrated successful expression of SV2 proteins. The COS-7 cell line was tested for $^3$H-30889 binding, with no binding above background observed, and thus no significant, measurable presence of the Levetiracetam binding site (LBS). In addition, a PC12 cell line subclone, PC12a, which is low in LBS, was used to establish a pool of PC12 cells expressing hSV2A under stable antibiotic selection.

Figure 12:
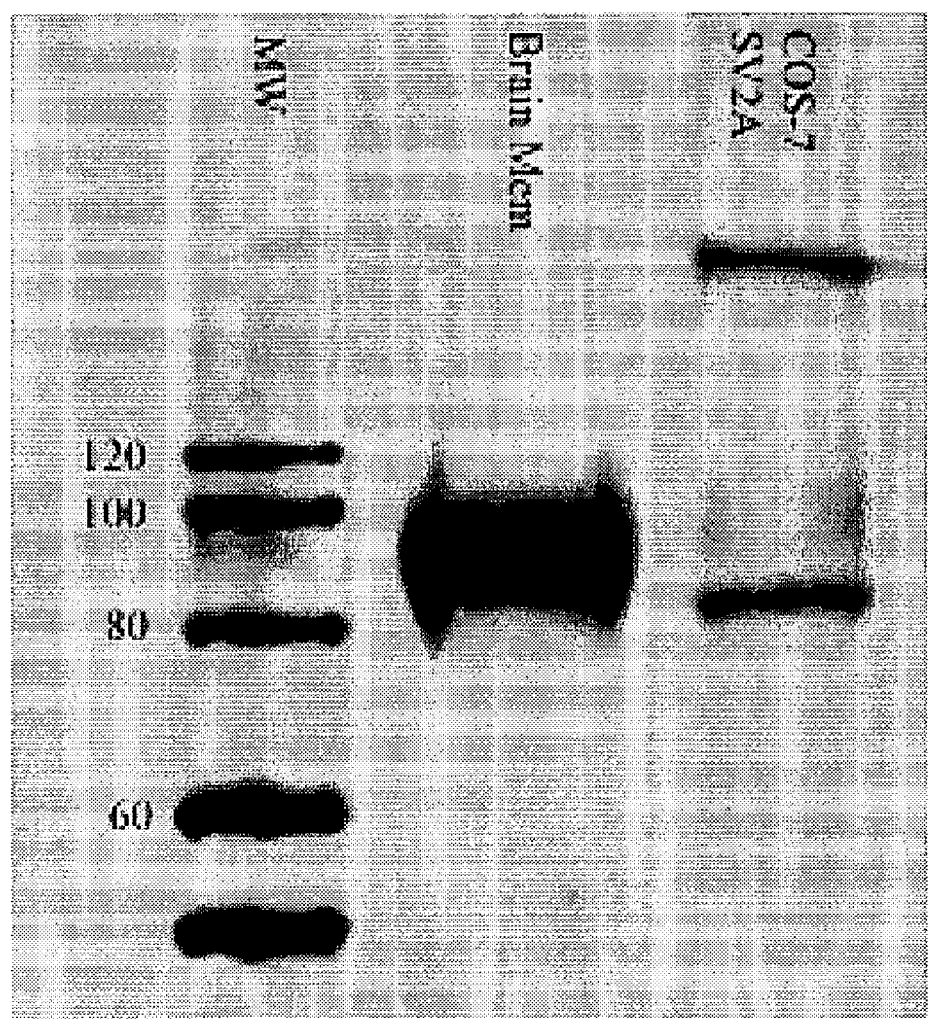
FIG. 12 (A and B) depicts immunostained lysates of the COS-7 cells transfected with SV2A, crude rat brain membranes, and several different PC12 lysates with different levels of LBS.
Figure 12:
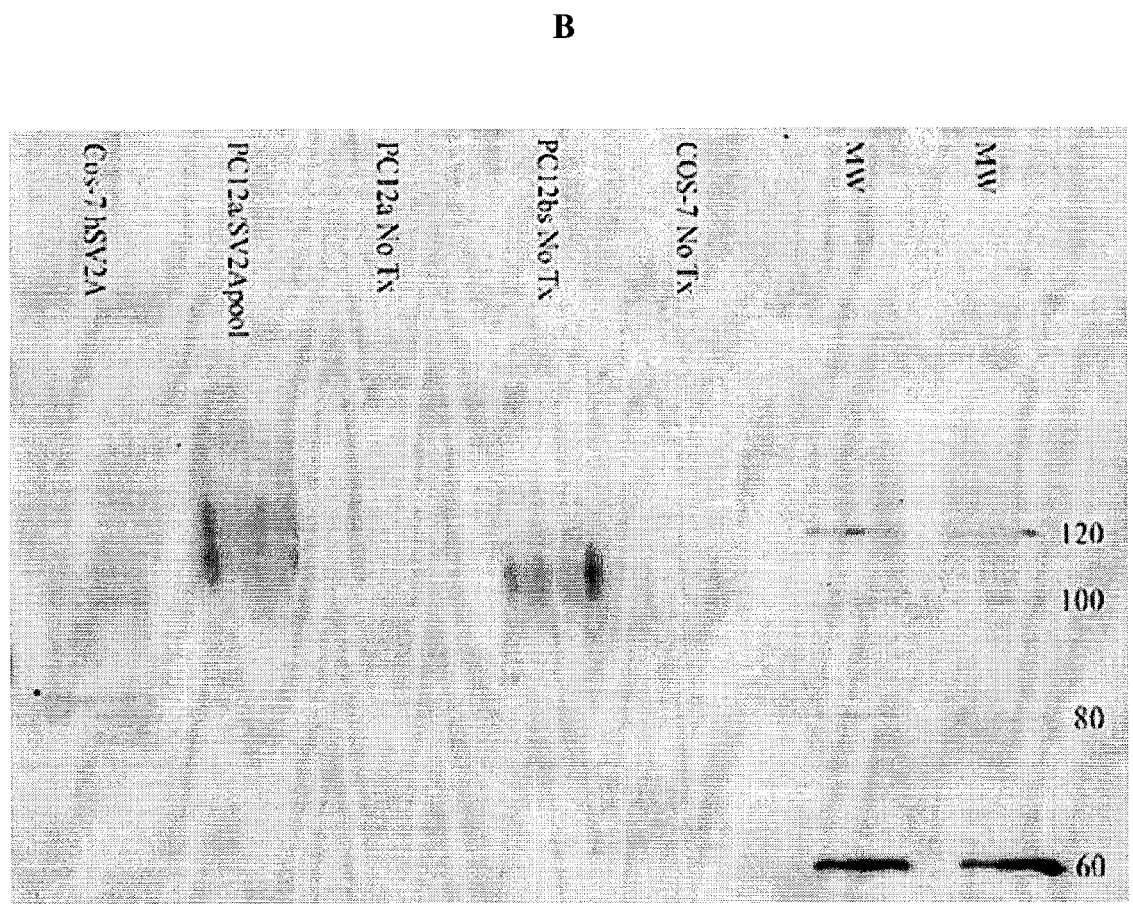

Lipofectamine 2000 (Invitrogen) transfection reagent was used to transfect DNA into 90% confluent COS-7 cells. Also, the same reagent was used to transfect the hSV2A containing vector into the PC12a cell line, and selecting for antibiotic resistance. Anti-SV2 polyclonal antibody (CalBiochem) was used to test for expression in either transfected COS-7 cells, or transfected PC 12a cells, of the SV2A product. Lysates of the COS-7 cells were collected at 18 hrs after transfection on an SDS-PAGE gel, transferred to a membrane, and probed with a polyclonal antibody against SV2A, in comparison to crude rat brain membranes (FIG. 12A). Also shown are lysates from a non-transfected COS-7 cells, non-transfected PC12a cells (low in LBS), PC12bs cells (high in LBS), or PC 12a cells transfected with hSV2A (FIG. 12B). No labeling of protein bands is observed in the untransfected COS-7 control, while the transfected COS-7 cells show multiple bands, with most density in the range of 80–120 kD, perhaps due to multiple glycosylation states of the expressed protein. In addition, SV2A immunoreactivity is present in the PC12bs and PC12a/hSV2A samples, but largely absent in the low LBS PC12a cells (FIG. 12B).

Figure 13:
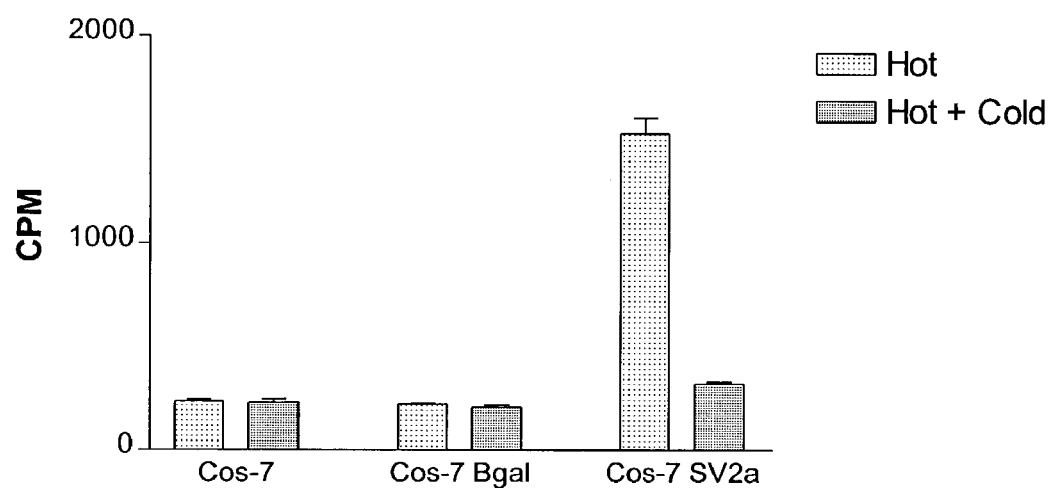
FIG. 13 depicts specific binding of $[^{3H}]$ucb30889 to COS-7 transfected with SV2A-12.2, transfected with control β-gal expressing vector, or cells that have not been transfected.

In a binding experiment, specific binding was measured of $^3$H-30889 to COS-7 cells that have either been transfected with SV2A-12.2, or as controls, a β-gal expressing vector, or cells that have not been transfected (FIG. 13). Triplicate wells of a 24-well plate were incubated with either 1 nM $^3$H-30889 (labeled "Hot"), or $^3$H-30889 plus an excess of cold Levetiracetam (50 μM) (labeled "Hot+Cold"). The cells were incubated at 4° C. for 2 hours, and then washed rapidly with ice-cold PBS. The cells were lysed on the plate, transferred to scintillation vials with scintillation fluid and counted for $^3$H decay emission. These results show that COS-7 cells transfected with SV2A have acquired the capability to specifically bind $^3$H-30889. In identical intact cell binding experiments using PC12bs cells, known to express the LBS, a 1.5 to 2-fold difference in CPM between the 'hot' and 'hot+cold' samples is typically seen, as compared to the 5-fold difference seen here.

Figure 14:
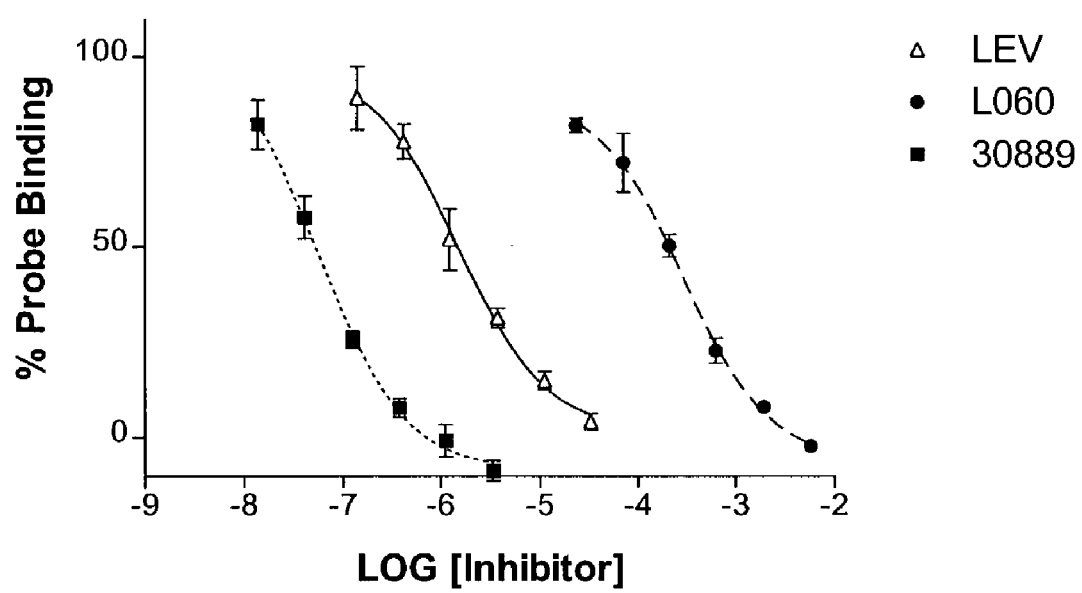
FIG. 14 depicts an IC50 plot comparing three different ligands binding to SV2A in the presence of 3H-30889.

Further studies characterized the binding of $^3$H-30889 to SV2A expressed in COS-7 cells in more detail. COS-7 cells were transfected in a 24-well plate and assayed for binding as above. A series of concentrations of either Levetiracetam, it's stereoisomer L060, or cold 30889 were added in order to generate IC50s for these compounds against SV2A expressed in COS-7 cells (FIG. 14). The measured IC50s are of the same rank order as seen in studies of LBS in rat brain, and with very similar measured IC50s of the three compounds. These results indicate that SV2A is functionally equivalent with the brain binding site for Levetiracetam that has been observed in rat brain and PC12 subclones, providing support that the synaptic vesicle protein SV2A is the native binding site for the anti-epileptic compound Levetiracetam, further suggesting a link between function and modulation of the synaptic vesicle and neurological disorders. Because of the correlation between LBS binding affinity and anti-seizure properties of Levetiracetam and its analogues, the binding of these compounds to SV2 family member proteins are likely to play an important role in their anticonvulsant properties.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A method of identifying a binding partner for a SV2A protein, comprising:
   a) providing a recombinant host cell expressing the SV2A protein or fragment thereof comprising a levetiracetam binding site (LBS), wherein the host cell is transfected or transformed with a nucleic acid encoding the SV2A protein or the fragment thereof to express the SV2A protein or the fragment thereof;
   b) incubating the host cell, levetiracetam or an analog or derivative thereof that binds the LBS of the SV2A protein, and a potential binding partner; and
   c) determining if the potential binding partner modulates the binding of levetiracetam or an analog or derivative thereof to the SV2A protein or the fragment thereof on the host cell, thereby identifying a binding partner for the SV2A protein.

2. A method of claim 1, wherein the step of determining if the potential binding partner modulates the binding of levetiracetam or an analog or derivative thereof to the host cell comprises comparing the binding to the host cell with that of a control.

3. A method of claim 2, wherein the control is a host cell that does not express the SV2A protein or the fragment thereof.

4. A method of claim 1, wherein the analog of levetiracetam is (2S)-2-[4-(3-azidophenyl)-2-oxopyrrolidin-1-yl]butanamide (ucb 30889).

5. A method of claim 1, wherein the SV2A protein is a mammalian SV2A.

6. A method of claim 5, wherein the mammalian SV2A protein is rat SV2A protein, mouse SV2A protein or human SV2A protein.

7. A method of claim 6, wherein the human SV2A protein comprises SEQ ID NO: 2.

8. A method of claim 1, wherein the host cell is incubated with the levetiracetam or an analog or derivative thereof prior to incubation with the potential binding partner.

9. A method of claim 1, wherein the host cell is incubated with the levetiracetam or an analog or derivative thereof after incubation with the potential binding partner.

10. A method of claim 1, wherein the host cell is incubated with the levetiracetam or an analog or derivative thereof concurrently with the potential binding partner.

11. A method of claim 1, wherein the host cell is incubated with levetiracetam or (2S)-2-[4-(3-azidophenyl)-2-oxopyrrolidin-1-yl]butanamide (ucb 30889).

12. A method of identifying a binding partner for a SV2A protein, comprising:
   a) providing a recombinant host cell expressing the SV2A protein or fragment thereof comprising a levetiracetam bindingsite (LBS), wherein the host cell is transfected or transformed with a nucleic acid encoding the SV2A protein or the fragment thereof to express the SV2A protein or the fragment thereof;
   b) obtaining a cellular preparation from the recombinant host cell;
   c) incubating the cellular preparation, with levetiracetam or an analog or derivative thereof that binds the LBS of the SV2A protein, and a potential binding partner; and
   d) determining if the potential binding partner modulates the binding of levetiracetam or an analog or derivative thereof to the SV2A protein or the fragment thereof in the cellular preparation, thereby identifying a binding partner for the SV2A protein.

13. A method of claim 12, wherein the cellular preparation comprises cell membranes.

14. A method of claim 12, wherein the step of determining if the potential binding partner modulates the binding of levetiracetam or an analog or derivative thereof to the cellular preparation comprises comparing the binding to the cellular preparation with that of a control.

15. A method of claim 14, wherein the control is a cellular preparation obtained from cell that does not express a the SV2A protein or the fragment thereof.

16. A method of claim 12, wherein the analog of levetiracetam is (2S)-2-[4-(3-azidophenyl)-2-oxopyrrolidin-1-yl]butanamide (ucb 30889).

17. A method of claim 12, wherein the SV2A protein is a mammalian SV2A.

18. A method of claim 17, wherein the mammalian SV2A protein is rat SV2A protein, mouse SV2A protein or human SV2A protein.

19. A method of claim 18, wherein the human SV2A protein comprises SEQ ID NO: 2.

20. A method of claim 12, wherein cellular preparation is incubated with the levetiracetam or an analog or derivative thereof prior to incubation with the potential binding partner.

21. A method of claim 12, wherein the cellular preparation is incubated with the levetiracetam or an analog or derivative thereof after incubation with the agent or potential binding partner.

22. A method of claim 12, wherein the cellular preparation is incubated with the levetiracetam or an analog or derivative thereof concurrently with the agent or potential binding partner.

23. A method of claim 12, wherein the cellular preparation is incubated with levetiracetam or (2S)-2-[4-(3-azidophenyl)-2-oxopyrrolidin-1-yl]butanamide (ucb 30889).

24. A method of claim 12, wherein the potential binding partner is an agent or a compound.

* * * * *